US011666343B2

(12) United States Patent
Philipp et al.

(10) Patent No.: US 11,666,343 B2
(45) Date of Patent: Jun. 6, 2023

(54) NAVIGATED SURGICAL SYSTEM

(71) Applicant: Stryker Corporation, Kalamazoo, MI (US)

(72) Inventors: Christopher Philipp, Portage, MI (US); Donald W. Malackowski, Schoolcraft, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

(21) Appl. No.: 17/375,646

(22) Filed: Jul. 14, 2021

(65) Prior Publication Data
US 2021/0338253 A1 Nov. 4, 2021

Related U.S. Application Data

(60) Continuation of application No. 16/713,932, filed on Dec. 13, 2019, now Pat. No. 11,076,866, which is a (Continued)

(51) Int. Cl.
A61B 17/16 (2006.01)
A61B 17/15 (2006.01)
(Continued)

(52) U.S. Cl.
CPC .......... A61B 17/1622 (2013.01); A61B 17/15 (2013.01); A61B 17/151 (2013.01);
(Continued)

(58) Field of Classification Search
CPC ... A61B 17/1622; A61B 17/15; A61B 17/151; A61B 17/1626; A61B 17/32002
(Continued)

(56) References Cited

U.S. PATENT DOCUMENTS 3,593,966 A 7/1971 Munroe
4,002,891 A 1/1977 Porter
(Continued)

FOREIGN PATENT DOCUMENTS

| EP | 1093210 A2 | 4/2001 |
| WO | 2014114905 A1 | 7/2014 |
| WO | 2019046561 A1 | 3/2019 |

OTHER PUBLICATIONS

EPO, International Search Report and ISA Written Opinion for PCT App. No. PCT/US2006/024120, dated Jul. 2007.
(Continued)

Primary Examiner — David Luo
(74) Attorney, Agent, or Firm — Howard & Howard Attorneys PLLC

(57) ABSTRACT

A surgical system including a surgical tool and a navigation system for tracking the position of the surgical tool. The surgical tool comprising a housing including a variable speed motor and control module disposed within the housing. The navigation system comprising a navigation console in communication with the control module of the surgical tool, the navigation console may be configured to communicate instructions to the control module of the surgical tool based on the position of the surgical tool relative to a defined zone. The navigation console may be configured to deactivate the surgical tool based on the position of the surgical tool relative to the defined zone. The navigation console may also be configured to provide a user-selectable override option to allow continued operation of the surgical tool within the defined zone.

19 Claims, 51 Drawing Sheets

Related U.S. Application Data continuation of application No. 15/978,364, filed on May 14, 2018, now Pat. No. 10,517,610, which is a continuation of application No. 15/405,462, filed on Jan. 13, 2017, now Pat. No. 10,004,517, which is a division of application No. 14/169,437, filed on Jan. 31, 2014, now Pat. No. 9,559,624, which is a division of application No. 12/617,052, filed on Nov. 12, 2009, now Pat. No. 8,657,482, which is a division of application No. 11/472,012, filed on Jun. 21, 2006, now Pat. No. 7,638,958.

(60) Provisional application No. 60/809,645, filed on May 31, 2006, provisional application No. 60/694,592, filed on Jun. 28, 2005.

(51) Int. Cl.
| | |
|---|---|
| *A61B 17/32* | (2006.01) |
| *H02P 6/16* | (2016.01) |
| *B01F 31/40* | (2022.01) |
| *B01F 33/501* | (2022.01) |
| *B01F 35/90* | (2022.01) |
| *B01F 35/22* | (2022.01) |
| *B01F 35/221* | (2022.01) |
| *H02P 7/06* | (2006.01) |
| *H02K 11/215* | (2016.01) |
| *H02K 11/33* | (2016.01) |
| *H02K 7/14* | (2006.01) |
| *A61B 34/20* | (2016.01) |
| *A61B 17/00* | (2006.01) |
| *B01F 35/33* | (2022.01) |

(52) U.S. Cl.
CPC .... *A61B 17/1626* (2013.01); *A61B 17/32002* (2013.01); *B01F 31/40* (2022.01); *B01F 33/50111* (2022.01); *B01F 33/50115* (2022.01); *B01F 35/2207* (2022.01); *B01F 35/2209* (2022.01); *B01F 35/22161* (2022.01); *B01F 35/221422* (2022.01); *B01F 35/90* (2022.01); *H02K 7/145* (2013.01); *H02K 11/215* (2016.01); *H02K 11/33* (2016.01); *H02P 6/16* (2013.01); *H02P 7/06* (2013.01); *A61B 17/1697* (2013.01); *A61B 34/20* (2016.02); *A61B 2017/00017* (2013.01); *A61B 2017/00367* (2013.01); *A61B 2017/00734* (2013.01); *A61B 2034/2048* (2016.02); *A61B 2034/2051* (2016.02); *A61B 2034/2055* (2016.02); *B01F 35/332* (2022.01)

(58) Field of Classification Search
USPC .......................................... 318/560, 3; 606/1
See application file for complete search history.

(56) References Cited

U.S. PATENT DOCUMENTS

| | | | |
|---|---|---|---|
| 4,266,180 A | 5/1981 | Juvan | |
| 4,361,404 A | 11/1982 | Colin et al. | |
| 5,071,040 A | 12/1991 | Laptewicz, Jr. | |
| 5,136,220 A | 8/1992 | Philipp | |
| 5,193,907 A | 3/1993 | Faccioli et al. | |
| 5,207,697 A | 5/1993 | Carusillo et al. | |
| 5,265,956 A | 11/1993 | Nelson et al. | |
| 5,435,645 A | 7/1995 | Faccioli et al. | |
| 5,472,273 A | 12/1995 | Fowler et al. | |
| 5,505,538 A | 4/1996 | Earle | |
| 5,531,519 A | 7/1996 | Earle | |
| 5,571,282 A | 11/1996 | Earle | |
| 5,672,945 A | 9/1997 | Krause | |
| 5,747,953 A | 5/1998 | Philipp | |
| 5,754,741 A * | 5/1998 | Wang ................. A61B 34/70 700/262 |
| 5,797,680 A | 8/1998 | Murray | |
| 5,951,160 A | 9/1999 | Ronk | |
| 5,961,211 A | 10/1999 | Barker et al. | |
| 5,975,751 A | 11/1999 | Earle | |
| 5,977,746 A | 11/1999 | Hershberger et al. | |
| 6,013,991 A | 1/2000 | Philipp | |
| 6,017,354 A | 1/2000 | Culp et al. | |
| 6,024,480 A | 2/2000 | Seaton et al. | |
| 6,025,683 A | 2/2000 | Philipp | |
| 6,033,105 A | 3/2000 | Barker et al. | |
| 6,037,724 A * | 3/2000 | Buss ................ A61B 17/1626 439/71 |
| 6,042,262 A | 3/2000 | Hajianpour | |
| 6,126,307 A | 10/2000 | Black et al. | |
| 6,176,607 B1 | 1/2001 | Hajianpour | |
| 6,296,635 B1 * | 10/2001 | Smith ................. A61B 34/76 606/1 |
| 6,436,107 B1 | 8/2002 | Wang et al. | |
| 6,656,515 B2 | 12/2003 | Lowry et al. | |
| 6,887,245 B2 | 5/2005 | Kienzle, III et al. | |
| 6,960,894 B2 * | 11/2005 | Carusillo ............ A61B 17/142 318/434 |
| 6,962,220 B2 | 11/2005 | Takenaka et al. | |
| 7,116,071 B2 | 10/2006 | Glasgow et al. | |
| 7,274,866 B2 | 9/2007 | Rudolf | |
| 7,422,582 B2 | 9/2008 | Malackowski et al. | |
| 7,441,943 B2 | 10/2008 | Barker et al. | |
| 7,638,958 B2 | 12/2009 | Philipp et al. | |
| 7,658,537 B2 | 2/2010 | Coffeen et al. | |
| 7,854,543 B2 | 12/2010 | Coffeen et al. | |
| 8,132,959 B2 | 3/2012 | Smit | |
| 8,172,456 B2 | 5/2012 | Coffeen et al. | |
| 8,657,482 B2 | 2/2014 | Malackowski et al. | |
| 9,559,624 B2 | 1/2017 | Philipp | |
| 9,707,026 B2 | 7/2017 | Malackowski et al. | |
| 10,004,517 B2 | 6/2018 | Phillip | |
| 10,517,610 B2 | 12/2019 | Philipp et al. | |
| 11,076,866 B2 | 8/2021 | Phillipp et al. | |
| 2001/0043806 A1 | 11/2001 | Gorti et al. | |
| 2002/0003045 A1 | 1/2002 | Bongers-Ambrosius | |
| 2002/0188259 A1 | 12/2002 | Hickle et al. | |
| 2003/0093103 A1 | 5/2003 | Malackowski et al. | |
| 2004/0022527 A1 | 2/2004 | Carusillo et al. | |
| 2004/0085041 A1 | 5/2004 | Prudham | |
| 2004/0267272 A1 | 12/2004 | Henniges et al. | |
| 2005/0020909 A1 | 1/2005 | Moctezuma de la Barrera et al. | |
| 2005/0141338 A1 | 6/2005 | Jarvinen et al. | |
| 2006/0074405 A1 | 4/2006 | Malackowski et al. | |
| 2006/0142656 A1 | 6/2006 | Malackowski et al. | |
| 2007/0085496 A1 | 4/2007 | Philipp et al. | |
| 2007/0090788 A1 | 4/2007 | Hansford et al. | |
| 2008/0223146 A1 | 9/2008 | Atkinson et al. | |
| 2009/0257306 A1 | 10/2009 | Coffeen et al. | |
| 2010/0061181 A1 | 3/2010 | Malackowski et al. | |
| 2010/0110820 A1 | 5/2010 | Coffeen et al. | |
| 2010/0130964 A1 | 5/2010 | Ware et al. | |
| 2010/0276482 A1 | 11/2010 | Raihi et al. | |
| 2012/0224452 A1 | 9/2012 | Melsheimer et al. | |
| 2020/0113583 A1 | 4/2020 | Philipp et al. | |

OTHER PUBLICATIONS

European Patent Office, "Search Report for EP App. No. EP 10 007 515.9, dated Jul. 2011".

* cited by examiner

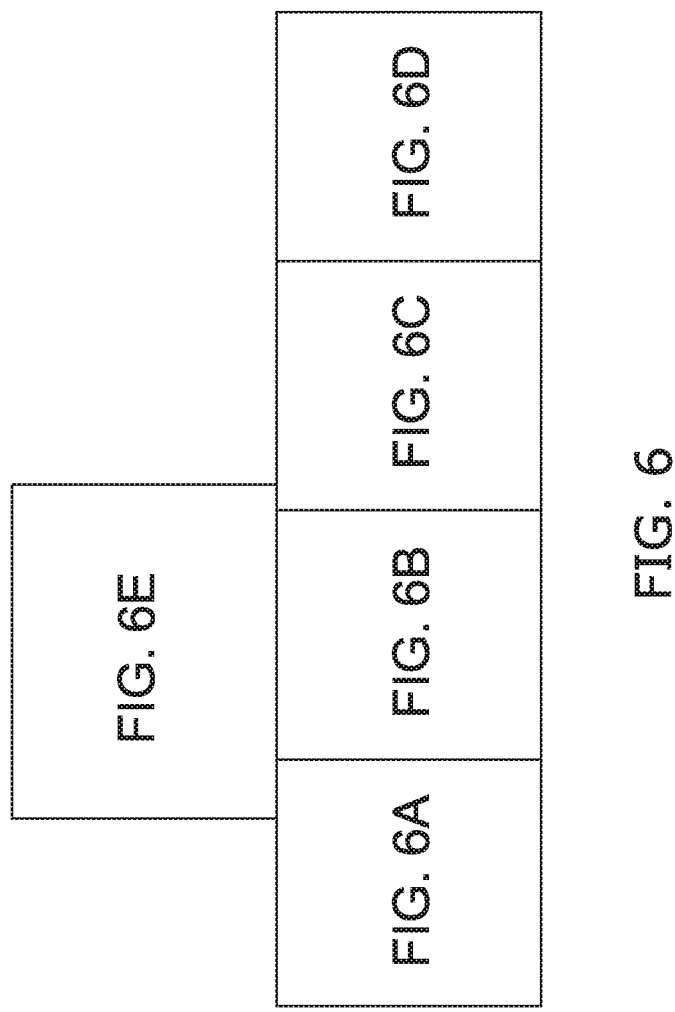

NAVIGATED SURGICAL SYSTEM

RELATIONSHIP TO EARLIER FILED APPLICATIONS

This application is a continuation of U.S. patent application Ser. No. 16/713,932 filed Dec. 13, 2019, which is a continuation of U.S. patent application Ser. No. 15/978,364 filed May 14, 2018, now U.S. Pat. No. 10,517,610. U.S. patent application Ser. No. 15/978,364 is a continuation of U.S. patent application Ser. No. 15/405,462 filed Jan. 13, 2017, now U.S. Pat. No. 10,004,517. U.S. patent application Ser. No. 15/405,462 is a divisional of U.S. patent application Ser. No. 14/169,437 filed Jan. 31, 2014, now U.S. Pat. No. 9,559,624. U.S. patent application Ser. No. 14/169,437 is a divisional of U.S. patent application Ser. No. 12/617,052 filed Nov. 12, 2009, now U.S. Pat. No. 8,657,482. U.S. patent application Ser. No. 12/617,052 is a divisional of U.S. patent application Ser. No. 11/472,012 filed Jun. 21, 2006, now U.S. Pat. No. 7,638,958. U.S. patent application Ser. No. 11/472,012 claims priority under 35 U.S.C. § 119 from U.S. Provisional Pat. App. No. 60/694,592 filed Jun. 28, 2005 and U.S. Provisional Pat. App. No. 60/809,645 filed May 31, 2006. The contents of the applications from which the present application claims priority are explicitly incorporated herein by reference.

FIELD OF THE INVENTION

This invention is generally related to electrically powered surgical tools. More particularly, this invention is related to a cordless, powered surgical tool with a sealed module in which the circuit that controls the activation of the tool is enclosed.

BACKGROUND OF THE INVENTION

In modern surgery, one of the most important instruments available to medical personnel is the powered surgical tool. Often this tool is in the form of a drill unit in which a motor is housed. Secured to the drill unit is a cutting attachment designed for application to a surgical site on to perform a specific medical procedure. For example, some powered surgical tools are provided with drills, burs or reamers for cutting bores into tissue or for selectively removing tissue such as bone. Other powered surgical tools are provided with saw heads. These tools separate large sections of hard and soft tissue. A wire driver is a power tool that, as its name implies, drives a wire into a patient, more particularly, a bone. Power tools are also used to perform other functions in the operating room. For example, it is known to use a power tool to mix the components that form a mass of surgical cement.

The ability to use powered surgical tools on a patient lessens the physical strain of surgeons when performing medical procedures on a patient. Moreover, most surgical procedures can be performed more quickly and more accurately with powered surgical tools than with the manual equivalents that preceded them.

One type of powered surgical tool that is especially popular with some physicians is the cordless, battery-operated powered surgical tool. As the name implies, this tool has a battery that serves as the power source for the motor. This eliminates the need to provide the tool with a power cord connected to an external-power source. Elimination of the power cord offers benefits over corded, powered surgical tools. Surgical personnel using this type of tool do not have to concern themselves with either sterilizing a cord so the cord can be introduced into the sterile surgical field or ensuring that, during a procedure, an unsterilized section cord is not inadvertently introduced into the surgical field. Elimination of the cord also results in the like elimination of the physical clutter and field-of-view blockage a cord brings to a surgical procedure.

One feature shared by both corded and cordless power surgical tools is the presence of a control switch or member on the tool. This member is often in the form of a biased switch, trigger or button. A number of corded and cordless surgical tools have handles similar to pistol handgrips. A tool of this shape is sometimes designed so the control member is trigger that is slidably mounted to the handle.

Powered surgical tools, unlike many other power tools, have to do more than deliver relatively large amounts of power. A powered surgical tool must be able to withstand repeated exposure to an environment both saturated with water vapor and very hot. This is because, prior to use, a powered surgical tool is autoclave sterilized. In this process, the tool is placed in a chamber where there is atmosphere is saturated with water vapor (steam), the temperature is approximately 270° F. and the atmospheric pressure is approximately 30 psi (Gage). Internal components of the tool, including the conductive components of its control circuit, if left unprotected in and repeatedly exposed to this environment, corrode.

The Applicant's U.S. Pat. No. 5,747,953, CORDLESS, BATTERY OPERATED SURGICAL TOOL, issued May 5, 1998, and incorporated herein by reference, discloses one means for protecting the internal components of a surgical tool from the effects of autoclave sterilization. The tool of this invention has a sealed module that houses the circuit that regulates tool actuation. Also internal to this module are contactless sensors that monitor the states of externally mounted triggers. Attached to each trigger and located inside the tool housing is a magnet. Internal to the module are magnetic field sensors. Each sensor generates a varying signal as a function of the proximity of an associated one of the trigger magnets. The manual displacement of the trigger results in a like displacement, inside the tool, of the magnet. When a trigger and magnet are so displaced, the complementary sensor generates a signal that indicates the movement has occurred. Upon receipt of this signal, the control circuit generates the signal needed to allow an energization current to be applied to the motor.

The electrically conductive components of the on/off control assembly of the above tool are shielded from the supersaturated heated air of the autoclave environment. When this tool is sterilized, these components are not adversely affected.

However, known cordless power tools have other sensitive components that remain exposed. These components typically include the sensors that monitor the operation of the power-producing units. Many motorized cordless power surgical tools, for example, employ brushless DC-motors as their power-producing units. Internal to this type of motor are sensors that monitor the position of the motor's rotor. The signals produced by the sensors are supplied to the control circuit. These signals function as feedback signals that, with the on/off signals, regulate the commutation of the motor.

These sensors are exposed to the corrosion fostering environment of the autoclave. Currently, these sensors are encased in a potting compound to shield them from the harsh effects of the sterilization process. Nevertheless, over time, pressurized water vapor can reach these sensors. Once this occurs, the water vapor has a tendency to corrode the sensors so as to cause their malfunction.

Even when these sensors remain shielded from the saturated water vapor, there are some disadvantages associated with their use. Often, these sensors operate best in low temperature environments. For example, the signals generated by Hall effect sensors start to vary at temperatures above 150° C. The motor integral with a powered surgical tool can generate enough heat to cause the temperature to rise above this level. Once this occurs, the variations in the signals output by the Hall sensors can cause the control circuit to generate control signals that foster tool malfunction.

Moreover, the accuracy of the motor rotor position signals generated by these sensors is naturally very dependent on sensor position relative to the rotor. Despite the best efforts of surgical personnel, it is not unheard of for surgical tools to drop to the floor. When a tool is exposed to this type of mechanical shock, the positions of the motor rotor sensors can shift. Such movement is still another reason why the sensors may to generate signals that do not accurately represent motor rotor position.

In theory, it should be possible to eliminate this problem by using the back EMF signals generated by the motor windings to obtain an indication of rotor position. This is how use of rotor position sensors in corded powered surgical tools is eliminated. In practice, it has proven difficult to implement this solution in a cordless powered tool. This is because, at zero speed, stall speed, there are no back EMF signals from which rotor position can be determined. Instead, other means are employed to energize the motor windings in order to start up the motor. These other means typically involve the application of significant currents to the windings. During a surgical procedure, a cordless power tool may be repeatedly cycled on and off. Therefore, if a cordless powered surgical tool were driven based on the state of back EMF signals, the power required to constantly restart the motor can result in relatively rapid depletion of the battery charge. This could require the battery to be changed in the middle of the procedure. Clearly, this is a task surgical personnel would like to avoid.

Moreover, many powered surgical tools, both of the corded and cordless variety, drive different cutting accessories. For example, many drill units are designed to drive both shavers and burs. Often, different accessories operate at different preferred speeds have different maximum operating speeds. A number of different assemblies are commercially available that provide feedback to the control console that energizes a corded power tool to indicate the type of attached cutting accessory. Based on this information, the control console regulates actuation of the tool so it operates at speeds appropriate to the attached accessory. However, a cordless power tool does not have a control console. Thus, it has proven difficult to provide a mechanism that can be used to custom regulate the operation of the tool based on the attached accessory.

Moreover, some corded powered surgical tools have control consoles able to provide custom speed or operation settings based on surgeon preference. Again, since a cordless tool is not connected to this type of console, it has proven difficult to provide surgeons with this type of control with this type of tool.

SUMMARY OF THE INVENTION

This invention is related to a new and useful powered surgical tool. The surgical tool of this invention does not rely on sensors integral with the tool power producing unit to determine the operating state of the unit. The surgical tool of this invention is also custom configurable based on the type of attached cutting accessory and/or surgeon preferences.

The powered surgical tool of this invention includes a handpiece that contains the power-producing component. Often this component is a DC motor. Also internal to the handpiece is a module that contains the control circuit that regulates the application of power to the motor. This control circuit is contained in a sealed module. Also internal to this housing are sensors that monitor the state of the actuation members attached to the handpiece and sensors that monitor the position of the motor rotor.

Since the handpiece of this invention does not have sensors integral with the motor, the problems associated with providing these sensors is eliminated.

The handpiece of this invention also has a processor that monitors the state of the signals generated by the actuation of the control members. The processor executes a specific set of operating instructions loaded each time the tool is set up for use in a procedure. Based on these instructions, the processor is directed to execute the received signals representative of control member actuation, the processor generates a specific set of control instructions.

The instructions selected for processor execution are loaded from a component remote to the tool. If the particular tool is a cordless tool, the instructions are transmitted by a wireless communications link. Thus, the powered surgical tool of this invention is custom configured for operation based on variables such as type of attached cutting accessory and surgeon preference.

In one embodiment, the powered surgical tool of this invention is a cordless tool. In other embodiments of this invention, the tool is corded.

BRIEF DESCRIPTION OF THE DRAWINGS

The invention is pointed out with particularity in the claims. The above and further features of this invention may be better understood by reference to the following detailed description taken in conjunction with the accompanying drawings in which:

FIG. 6 is an assembly diagram illustrating how

DETAILED DESCRIPTION

I. Surgical Power Tool

A. Overview

Figure 1:
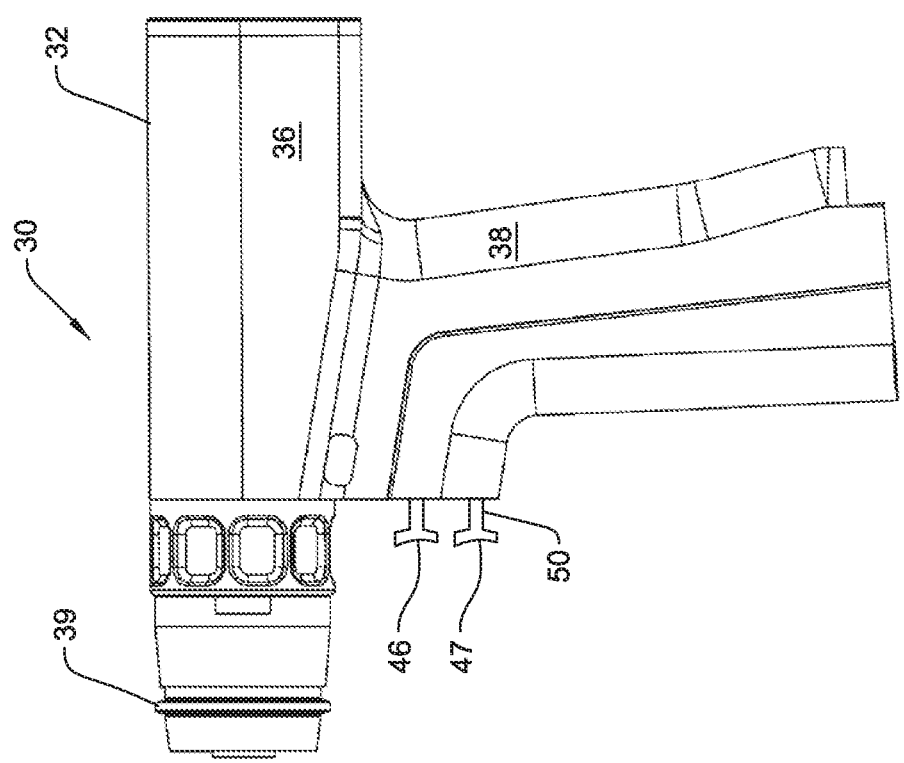
FIG. 1 is a side view of a powered tool incorporating the features of this invention.
Figure 1A:
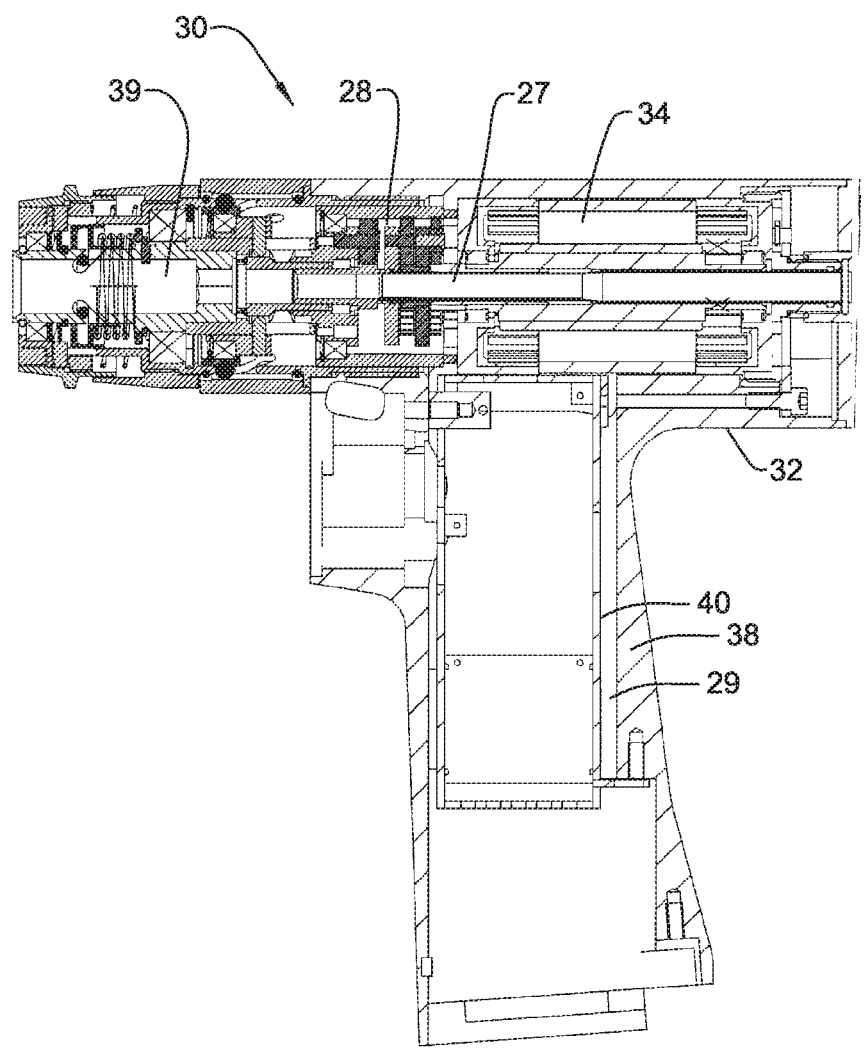
FIG. 1A is a cross sectional view of a powered tool of this invention.

FIGS. 1 and 1A illustrate a power tool 30, a surgical tool, constructed in accordance with this invention. Tool 30 has a housing 32 in which in electrically-actuated power-generating unit is located. In the specific tool 30, this power-generating unit is a brushless, Halless, DC motor 34. Tool housing 32 is shaped to have a generally cylindrical head 36 in which motor 34 is fitted. Extending downwardly from head 36, tool housing 32 is shaped to have a handle 38.

Also contained in the head 36 is a coupling assembly 39 represented by a ring moveably mounted to the front of housing 32. Coupling assembly 39 consists of the mechanical linkage that releasably attaches a surgical attachment 41 (FIG. 16) to the motor 34 so that the motor can actuate the attachment. In some tool systems of this invention, attachment 41 is referred to as a cutting accessory. The exact structure of the coupling assembly 39 is not relevant to the structure of this invention. If, as in the tool of FIGS. 1 and 1A, the power generating unit is motor 34, coupling assembly 39 consists of a locking arrangement that releasably holds the accessory to the motor shaft 27 so that accessory rotates with the rotation of the motor shaft. In some versions of the invention, a speed reduction gear assembly 28 is located between motor 34 and coupling assembly 39.

Disposed inside a void space 29 internal to the handle is a hermetically sealed control module 40 shown in phantom in FIG. 1. Control module 40, as discussed below, contains the components that regulate the application of energization current to the motor 34.

Figure 6A:
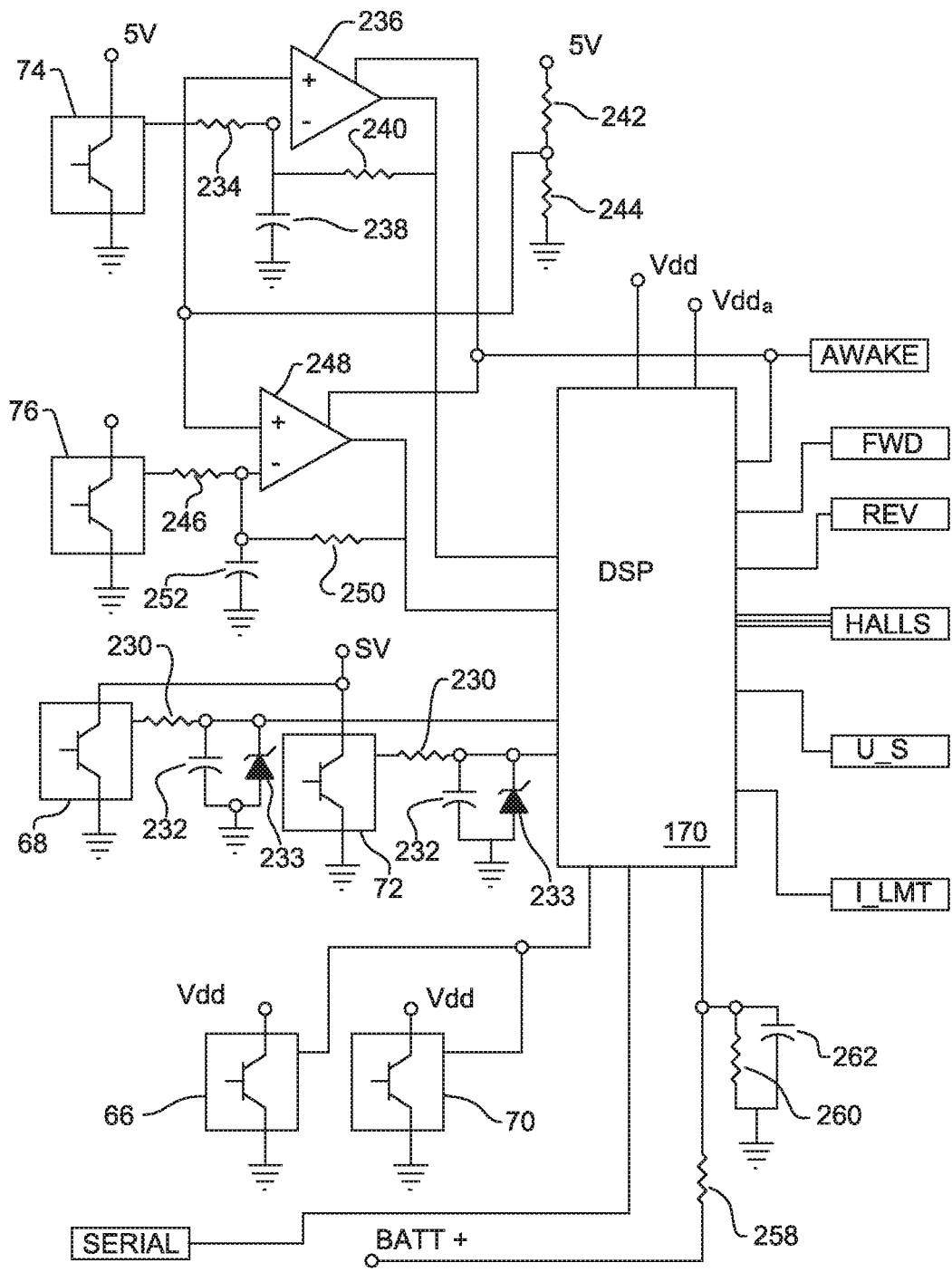
FIGS. 6A, 6B, 6C, 6D and 6E are assembled to from a schematic and block diagram of the control circuit of this invention.
Figure 6B:
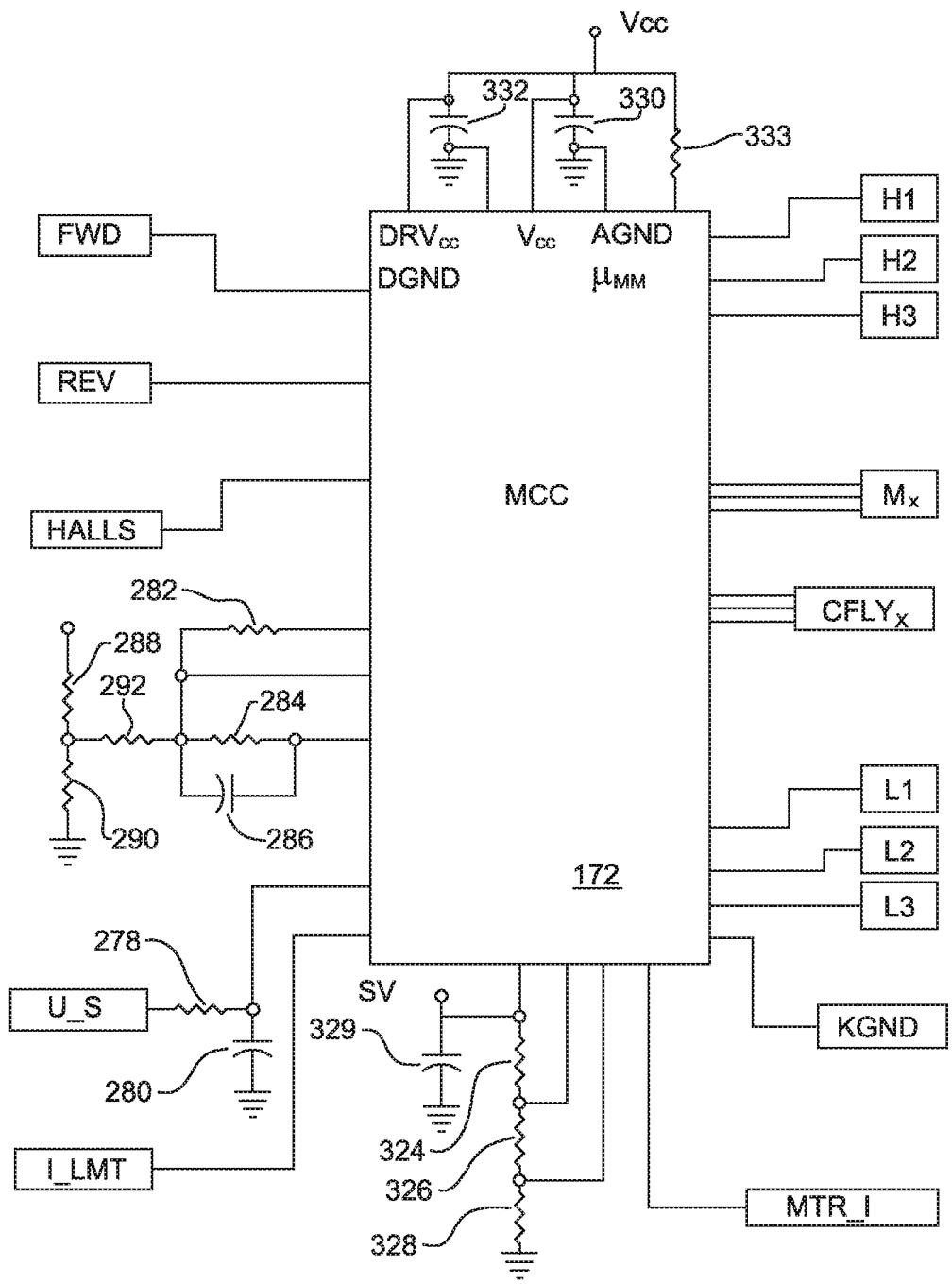
Figure 6C:
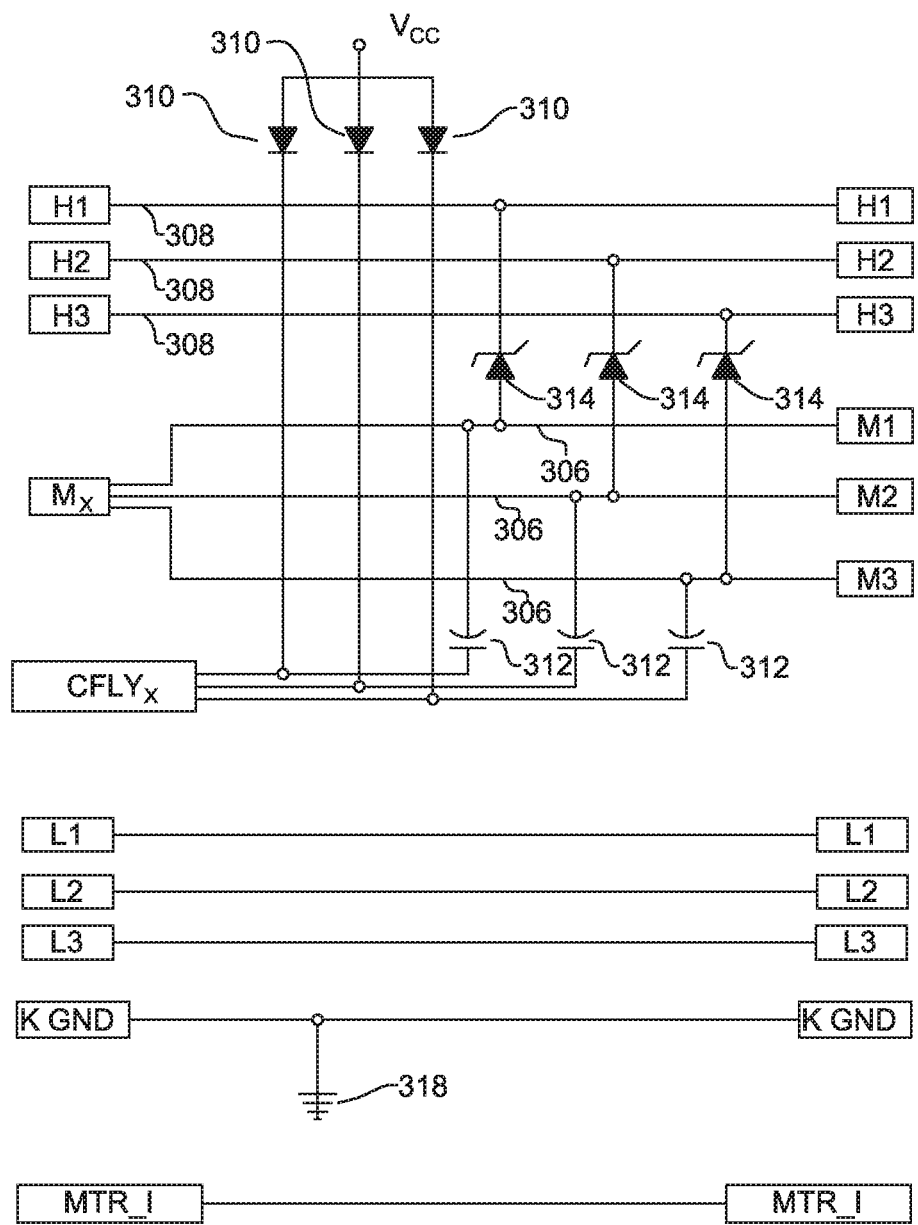
Figure 6D:
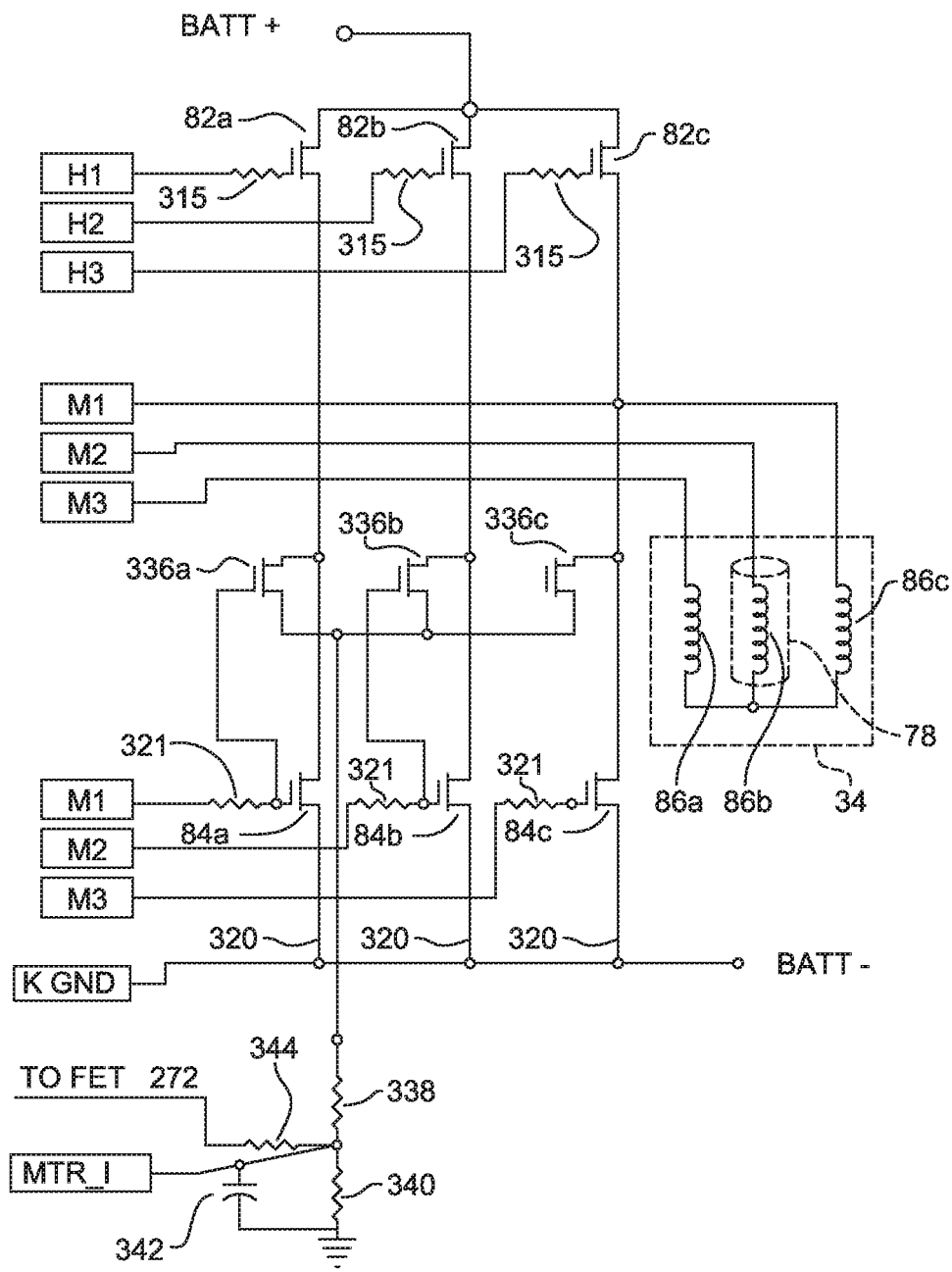
Figure 6E:
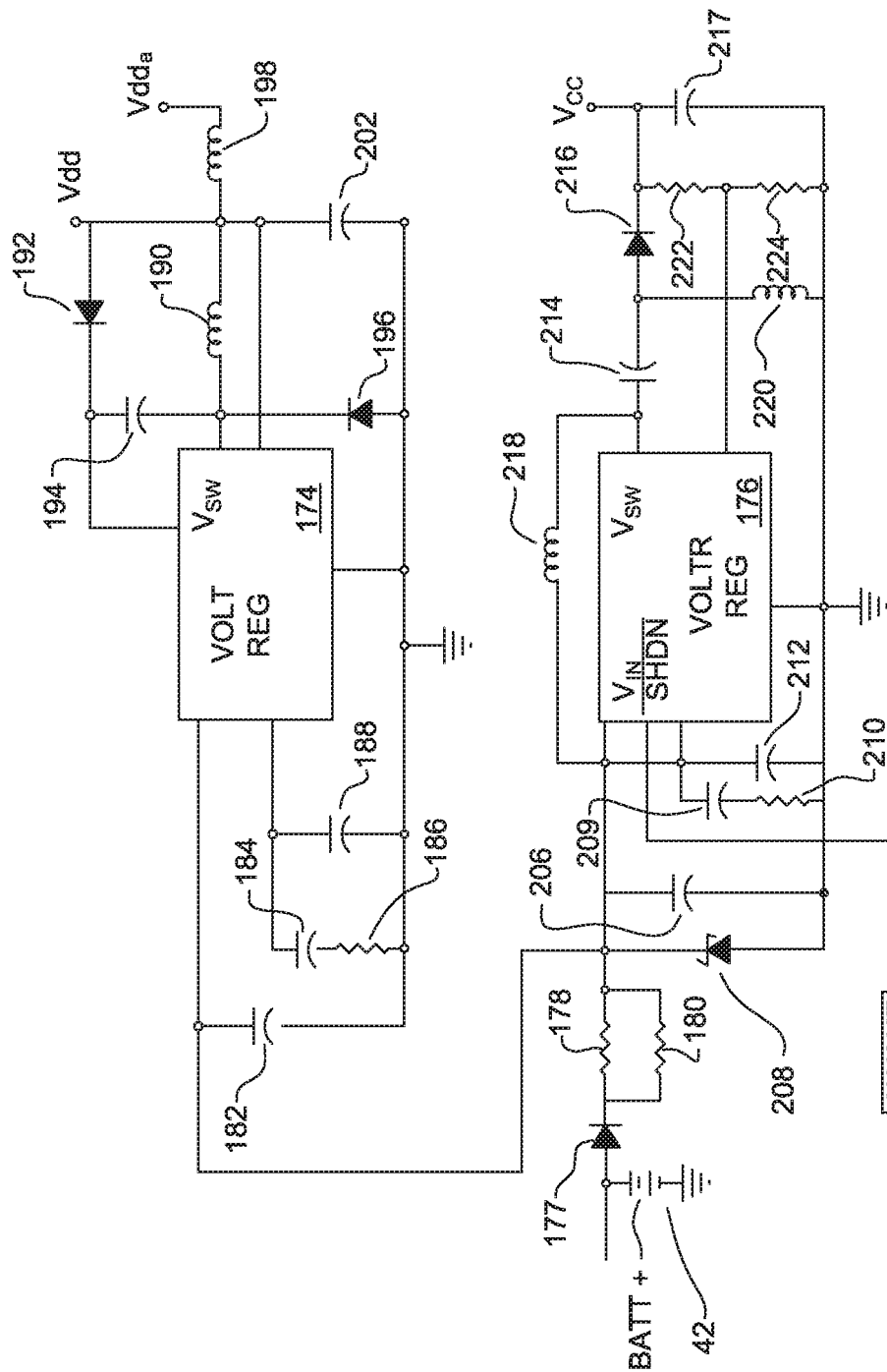

Power for energizing the motor 34 is from a battery 42, shown schematically in FIG. 6E. In practice, the battery 42 is removably attached to the butt end of the handle 38. One battery 42 that can be employed with this version of the invention is described in the Applicant's Assignee's U.S. Pat. No. 5,977,746, entitled RECHARGEABLE BATTERY PACK AND METHOD FOR MANUFACTURING SAME issued 2 Nov. 1999 and incorporated herein by reference.

Two trigger switches 46 and 47 arranged in tandem extend forward from the front face of the handle 38. Each trigger switch 46 and 47 is slidably mounted to the tool housing 32. Each trigger switch 46 and 47 includes a generally cylindrical barrel 50. The barrel 50 is the portion of the trigger switch 46 or 47 that extends forward of the housing handle 38. A head 52, shaped as a fingerhold, is disposed over the distal free end of the barrel 50. ("Distal", it shall be understood means toward the surgical site to which the tool 30 is directed. "Proximal", means away from the surgical site.) Trigger switches 46 and 47 are mounted to tool housing 32 so that the barrels 50 are located in front and are aligned with the control module 40.

B. Mechanical Features

Figure 2A:
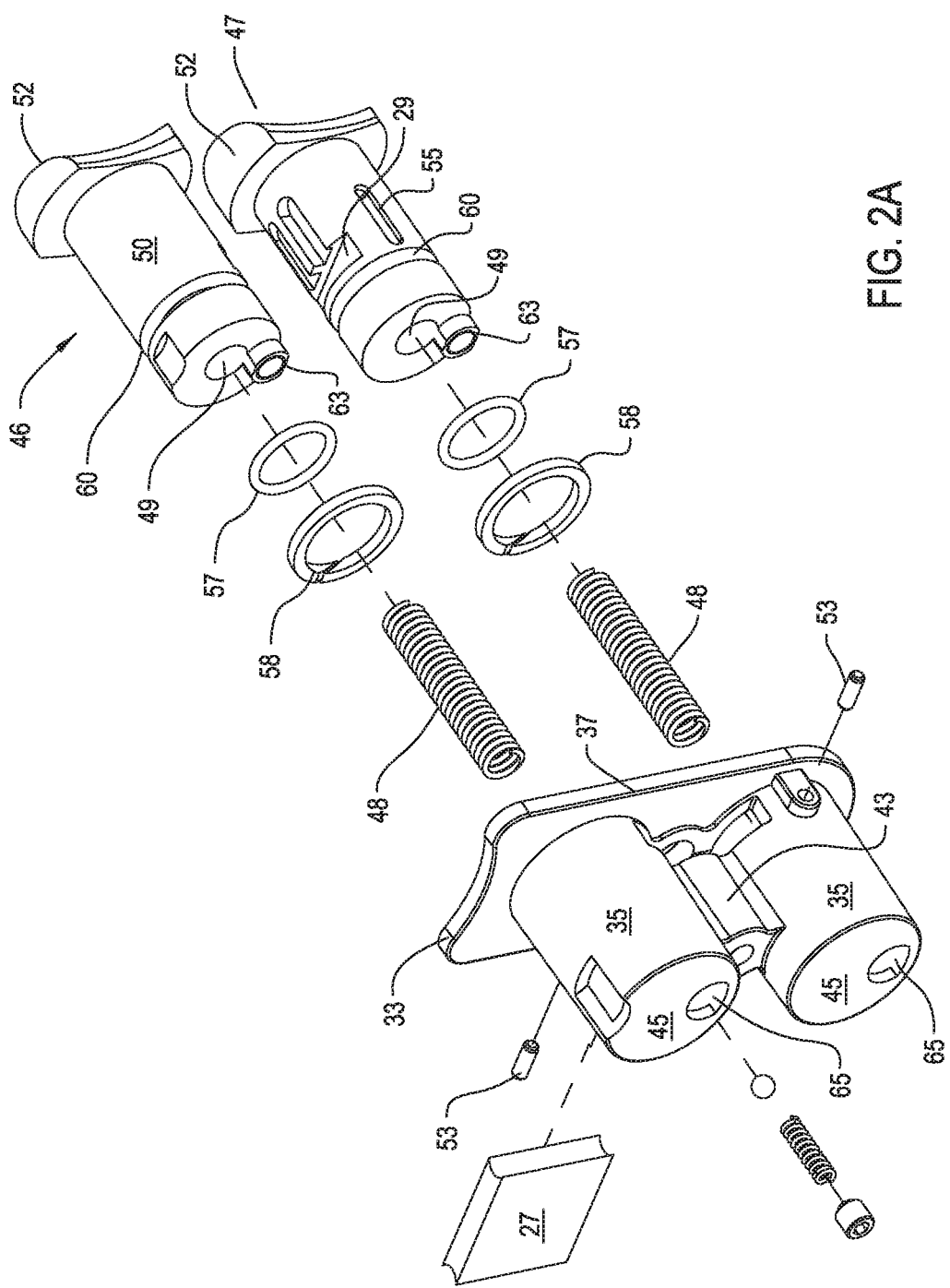
FIG. 2A is an exploded view of a trigger assembly the tool of this invention.
Figure 2B:
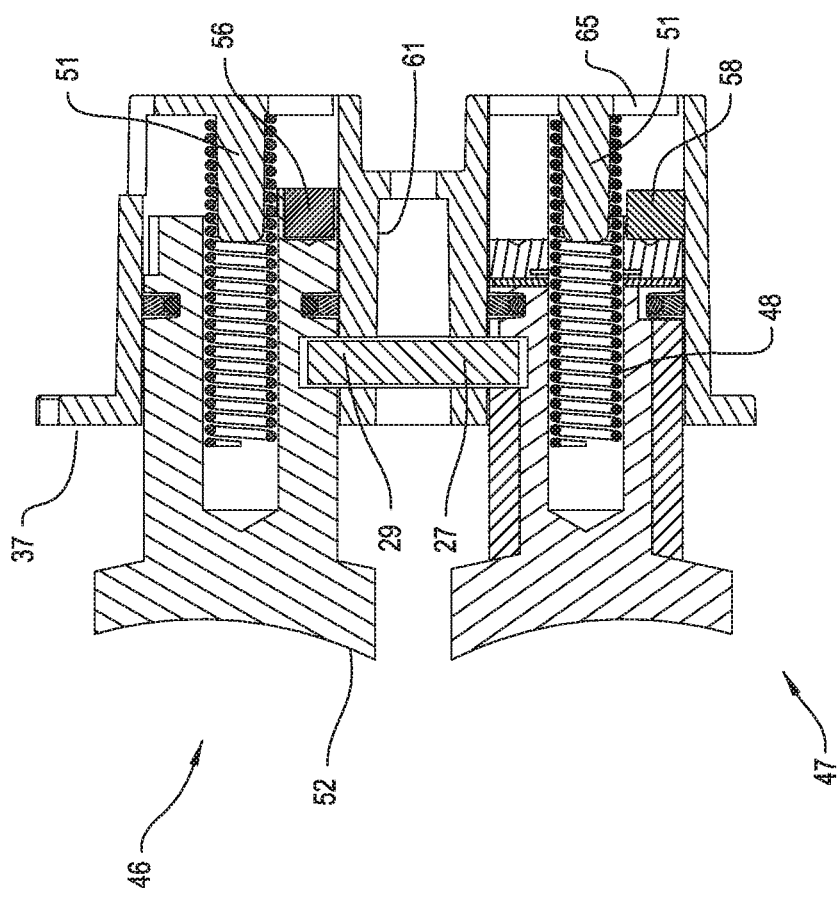
FIG. 2B is a cross sectional view of the trigger assembly.

FIGS. 2A and 2B collectively illustrate how trigger switches 46 and 47 are mounted in a trigger switch housing 33. Trigger switch housing 33 is formed of plastic. The housing 33 is shaped to define two barrel cages, each of which is closed at its proximal end. Each barrel cage 35 is dimensioned to facilitate the slidable slip fitting of one of the associated trigger switch barrels 50. A mounting plate 37 is formed integrally with and extends around the open distal end of the barrel cages 35. Mounting plate 37 is dimensioned to fit in a recessed space defined by the front face of the handle 38 (recessed space not illustrated). A fitting boss 43 extends proximally rearward from mounting plate 37 between the barrel cages 35. Fitting boss 43 has an axially extending through bore 61. A fastening member, not illustrated, extends through boss 43 to hold trigger switch housing 33 to tool housing 32. Trigger switch housing 33 is formed with stop walls 45 that extend across the proximal ends of barrel cages 35. Stop walls 45 are the trigger housing structural members against which the proximal ends of barrels 50 abut when the trigger switches 46 and 47 are fully depressed.

Helical springs 48 normally hold trigger switches 46 and 47 in the fully extended position. Each spring 48 is seated in a longitudinal closed-end bore 49 that extends distally from the proximal end of the associated trigger switch barrel 50. The proximal end of spring 48 bears against housing stop wall 45. The spring 48 is seated around a post 51 that extends distally forward from the inner wall of housing stop wall 45. Post 51 extends partially into barrel bore 49. Forward, distal movement of each trigger switch 46 and 47 is limited by a separate pin 53. Each pin 53 is seated in an opening formed in the associated housing barrel cage 35 (opening not identified) and extends laterally into the space within the barrel cage. The pin 53 seats in a groove 55 that extends longitudinally along the outside of trigger barrel 50. (In FIG. 2A only the groove 55 of trigger switch 47 is shown.) Each groove 55 is closed at both ends so that the abutment of pin 53 against the end walls that define the groove limit both forward and reverse movement of trigger switch 46 or 47.

An O-ring 57 and a Teflon ring 59 are seated in a groove 60 that extends circumferentially around the trigger switch barrel. Groove 60 is located between switch head 52 and longitudinal groove 55. O-ring 57 is seated in the base of the groove 60. Teflon ring 59 is a split ring seated in groove 60 over O-ring 57. The outer surface of Teflon ring 59 presses against the inner wall of barrel cage 35. Teflon ring 59 thus provides a low friction smooth interface between the trigger switch barrel 50 and the adjacent inner surface of the barrel cage 35.

In FIGS. 2A and 2B, a rectangular trigger assembly tool 27 is also shown. After trigger switches 46 and 47 are fitted into their barrel cages 45, tool 27 is slid into the barrel cages and the fitting boss 43. The opposed top and bottom ends of tool 27 seat in grooves 29 formed in the trigger switch barrels 50. Trigger assembly tool 27 holds the trigger switches 46 and 47 in position until pins 53 are seated in the barrel cages and switch barrel grooves 55.

Magnets 56 and 58 are attached to each trigger switch 46 and 47, respectively. Each magnet 56 and 58 is mounted to the proximal end of the trigger switch barrel 50. Each trigger switch barrel 50 has a boss 63 that extends proximally rearward from the proximal end of the barrel. The associated magnet 56 or 58 is seated in a closed end bore formed in the boss 63 (bore not identified).

Each housing barrel cage stop wall 45 is formed to have a proximal end opening 65. The trigger switch barrels 50 are seated in the barrel cage 35 so that when the associated switch is fully depressed, boss 60 and magnet 56 or 58 extend proximally rearward, through the associated opening 65, beyond the cage stop wall 45.

The depression of each trigger switch 46 or 47 thus causes the associated magnet 56 or 58, respectively, to move closer to the control module 40. Owing to the extension of the magnet 56 or 58 proximally beyond the barrel cage 35, the magnet, relative to the body of the trigger switch barrel 50, moves close to the control module 40. For reasons apparent below, tool 30 of this invention is assembled so that neither trigger switch 46 or 47 nor its complementary magnet 56 or 58 contact the control module 40.

Figure 3A:
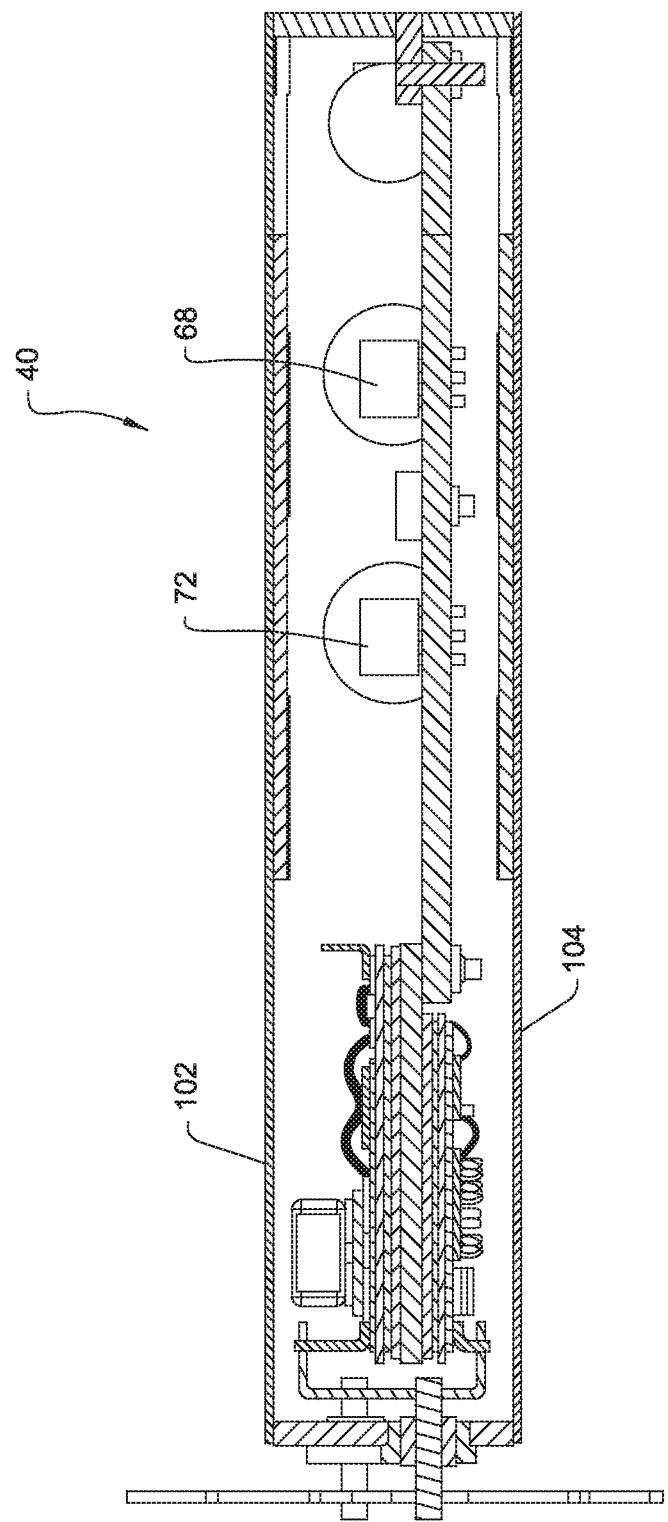
FIG. 3A is cross sectional view of the control module.

As seen in FIG. 3A, internal to the control module 40 is a printed circuit board 64. Mounted to the printed circuit board 64 are three pairs of sensors, sensor pair 66 and 68, sensor pair 70 and 72 and sensor pair 74 and 76 (FIG. 6A). Sensor pair 66 and 68 generates signals as a function of the relative position of magnet 56. Sensor pair 70 and 72 generates signals as a function of the relative position of the magnet 58. Sensor pair 74 and 76 generates signals as a function of the operation of the power-producing unit. In the present version of the invention, sensor pair 74 and 76 generate signals based on the rotational orientation of the motor rotor 78 shown symbolically in FIG. 6D.

Also internal to control module 40 are power FETs 82a-82c and 84a-84c (FIG. 6D). Each FET 82a, 82b and 82c selectively ties one of the motor windings 86a, 86b and 86c, (FIG. 6D) respectively, to the positive terminal of battery 42. Each FET 84a, 84b and 84c selectively ties one of the motor windings 86a, 86b and 86c to ground.

Mounted to printed circuit board 64 are other components discussed below. These components, based on the signals generated by sensor pairs 66-68, 70-72 and 74-76, selectively gate FETs 82a-82c and 84a-84c. The gating of FETs 82a-82c and 84a-84c causes current flow through the windings 86a-86c to energize motor 34.

Figure 3B:
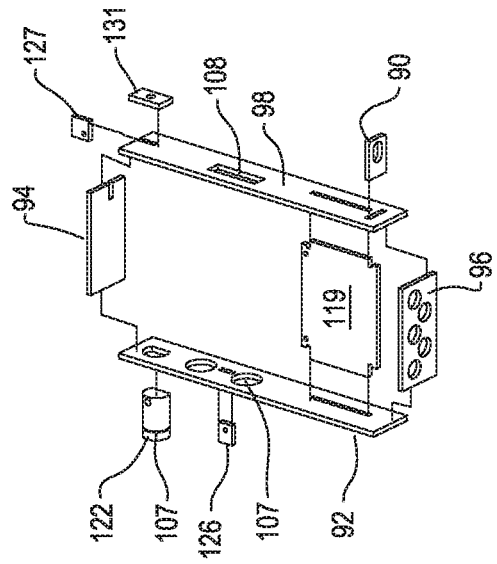
FIG. 3B is an exploded view of the panel members that form the control module.

Control module 40, as seen in FIGS. 3A and 3B, is formed from six plates. When the control module 40 is seated in the housing 32, a front plate 92 is the most distal of the plates and extends longitudinally inside the handle 38. Top and bottom plates 94 and 96, respectively, extend perpendicularly rearward through the handle 38 from the opposed top and bottom edges of the front plate 92. Back plate 98 is the most proximal of the plates. The back plate 98 extends between the proximal ends of the top and bottom plates 94 and 98, respectively. Front, top, bottom and back plates 92, 94, 96 and 98, respectively, are welded together to form a rectangular shell, (not identified). This shell defines the space within module 40 in which printed circuit board 64 is seated.

Lids 102 and 104 are the remaining two plates that form module 40. Lids 102 and 104 are rectangularly shaped and are seal over the opposed faces of printed circuit board 64.

Generally, the front plate 92, the bottom plate 96, the back plate 98 and the lids 102 and 104 are formed of magnetic material that is non-corrosive. One suitable material from which these components can be formed from nickel such as Nickel 200. These plates need to be magnetic because, in the described version of the invention, sensors 66-76 are magnetically sensitive. Forming the plates from a magnetic material shields the sensors from ambient magnetic fields. In one version of the invention, plates 92-98 are approximately 0.050 inches thick; lids 102 and 104 are approximately 0.015 inches thick. The reduced thickness of the lids 102 and 104 facilitates the welding of the lids to the plates 92-98.

Figure 4B:
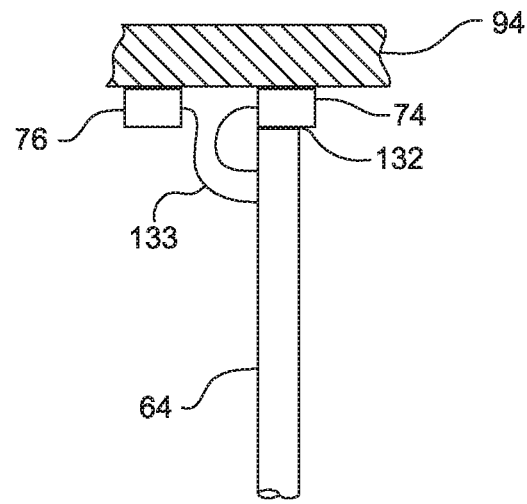
FIG. 4B is a side and partial cross sectional view of how the sensors that monitor motor rotor position are mounted to the printed circuit board internal to the control module.
Figure 4A:
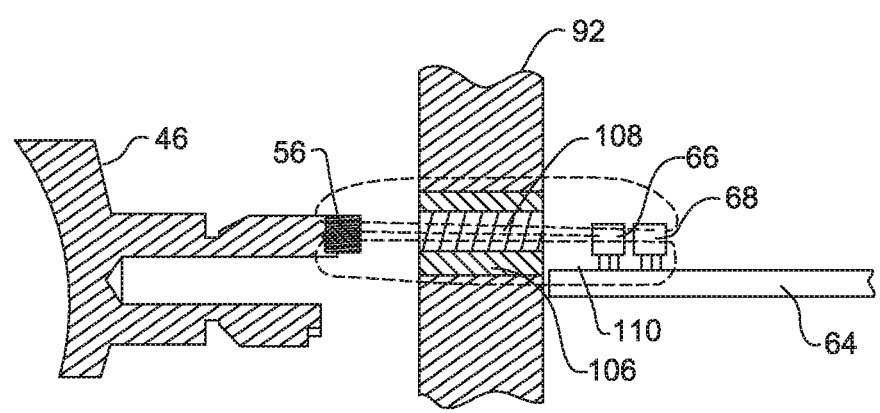
FIG. 4A is a side and partial cross-sectional view illustrating the arrangement of a trigger switch magnet to the sensors internal to the control module that monitor the position of the trigger switch.

While front plate 92 is generally formed of magnetic material, the sections of the plate that extend over the sensor pair 66 and 68 and sensor pair 70 and 72 are in the form of non-corrosive non-magnetic rings 106, seen in FIG. 4A. In one version of the invention, rings 106 are formed from copper or a copper-nickel alloy. One such alloy is sold under the trademark Monel by Inco Alloys of Huntington, W.V., United States. This alloy has a composition by weight of copper 30-35%, nickel 60-65%, remainder sulfur and carbon. Each ring 106 is mounted in an individual circular opening 107 formed in the front plate 92.

At the center of each ring 106 there is a solid disk 108 formed from magnetic material that is non-corrosive. Materials from which it may be possible to form disk 108 include nickel and nickel iron alloys. One such alloy from which disk 108 can be formed is sold under the trademark CARPENTER HIGH PERMEABILITY "49" by the Carpenter Steel Company of Reading, Pa., United States. This alloy has a compensation by weight of nickel 48%, carbon 0.02%, silicon 0.35%, manganese 0.50%, balance iron.

The reason front plate 92 is formed from the different materials is understood by reference to FIG. 4A. Each ring 106 and disk 108 pair is centered along the axial line of travel of one of the trigger switch magnets 56 or 58, magnet 56 shown. This line is also the axis along which the associated pair of sensors 66 and 68 or 70 and 72 is most sensitive to changes in magnetic field. Owing to the magnetic/non-magnetic/magnetic relationship between the front plate 92, ring 106 and disk 108, these components focus the flux of the magnetic field emitted by the magnet along this line. In FIG. 4A, the magnetic flux is illustrated by dashed lines 110. Consequently, slight changes in flux density caused by movement of the trigger switch 46 or 47 to which the magnet 56 or 58 is attached are readily sensed by the sensor pair 66 and 68 or 70 and 72.

Top plate 94, or at least portion thereof that covers sensors 74 and 76, is formed from a non-corrosive non-magnetic material. Copper or Monel alloy may be suitable materials from which this plate or plate section is formed. Top plate 94, or at least the section covering sensor pair 74 and 76, is formed from non-magnetic material because sensors 74 and 76 monitor changes in rotor orientation by monitoring the changes in the magnetic fields emitted by the rotor 78.

In some versions of the invention, opposed magnetic plates, not illustrated, extend upwardly from each of the lids 102 and 104. These plates are located on opposed sides of the location inside the control module 40 where sensor 74 and 76 are mounted. These plates shield sensors 74 and 76 from ambient magnetic fields.

Returning to FIGS. 3A, 3B, 3C and 3D, it is seen that back plate 98 is formed with a rectangular opening 108. Opening 108 functions as the opening in which a terminal board (not illustrated) is seated. Exposed contacts integral with the terminal board are the terminal points to which conductors (not illustrated) from a remote device are connected. The remote device serves as the head through which instructions for operating the surgical tool 30 are supplied to the control module 40 or data regarding the operating state of the tool are output from the module. This remote device may be a second terminal board positioned immediately behind an immediately removable plate over an opening in the tool housing 32 (terminal board, housing opening and plate not illustrated.) Alternatively, this remote device is the data transceiver head 530 described with respect to FIG. 16.

Module bottom plate 96 is formed with five circular openings 111. Each opening 111 houses a single driver/signal pin assembly 112, best seen in FIG. 5. Each driver/signal pin assembly 112 includes a copper core pin 113 that extends through module plate 96. Pin 113 extends through the center opening of a circular, bushing 114 seated around the perimeter of the opening 111. Bushing 114 is formed from cold rolled steel. A circular glass seal 115 holds the pin 113 in the center opening of the bushing 114.

A long clip connector 116 is fitted over the exposed end of each pin 113. Long clip connectors 116 are the module components to which wires to the battery 42 and windings 86a-86c are connected. In some versions of the invention, one or more of the long clip connectors 116 are eliminated.

Five driver/signal pin assemblies 112 are mounted to control module 40. Two of pin assemblies 112 serve as the conductive paths wherein the positive and negative connections to the battery 42 are made. The remaining three pin assemblies 112 function as the conductive paths over which separate connections are made to the motor windings 86a, 86b and 86c.

Figure 3D:
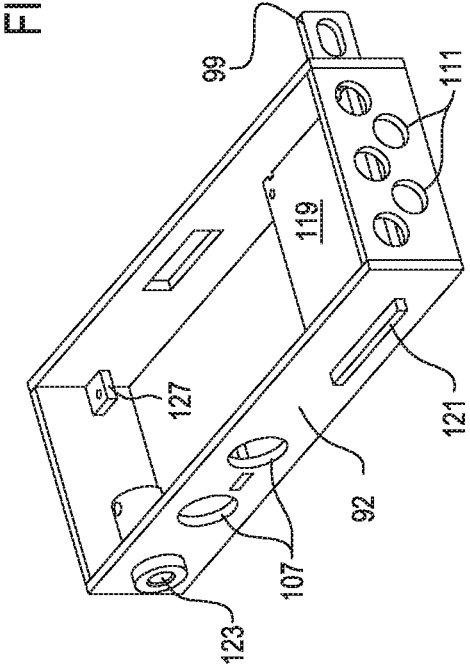
FIG. 3D is a perspective view of the interior of the control module illustrating some of the components mounted to and in the module.
Figure 3C:
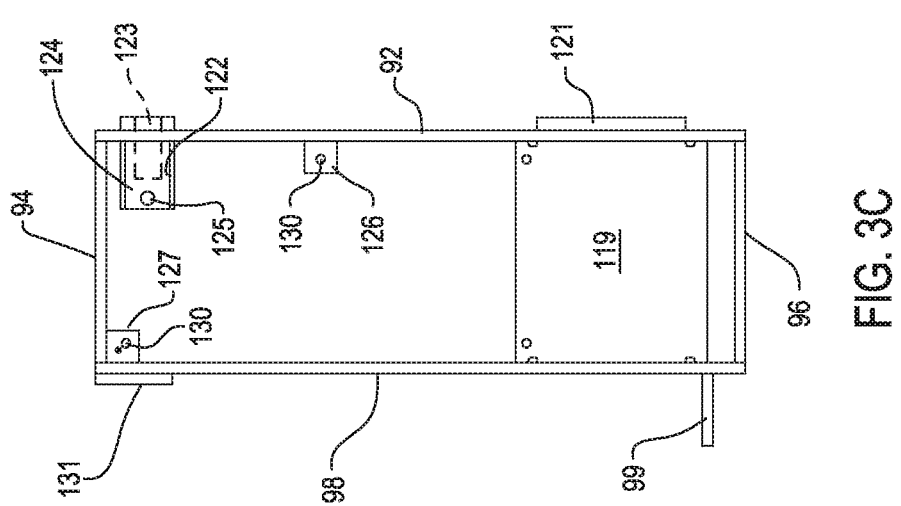
FIG. 3C is a plan view of the interior of the control module.

A rectangular mounting plate 119, best seen in FIGS. 3B and 3C, extends laterally forward from back plate 98 to and through front plate 92 at the bottom of control module 40. Mounting plate 119 is formed of material that has good thermal conductive properties for reasons that are apparent below. One such material is Nickel 200. The proximal end of the mounting plate 119 is seated in a rectangular slot 120 formed in the bottom plate 98 below opening 108. The distal end of mounting plate 119 extends through and forward of a similar rectangular slot formed in front plate 92, (slot not identified). Mounting plate 119 is dimensioned to have a distal end section 121 located distally forward of front plate 92.

When control module 40 of this invention, FETs 82a-82c and 84a-84c are disposed over opposed faces of mounting plate 119. The bottom end of circuit board 64 is disposed over and secured to an adjacent face surface of the top of the plate 119. When the control module 40 is fitted in handle 38, the plate distal end section 121 abuts an adjacent inner wall of the tool housing 32 that defines the space in which the module is seated. Since plate 119 serves as both the mounting surface for FETs 82*a*-82*c* and 84*a*-84*c* and physically contacts tool housing 32 the plate serves as a combined mounted surface and heat sink for the FETs. Distal end section 121 of mounting plate 119 further functions as a spacer to prevent the front end of control module 40 from pressing against the inner wall of the tool housing 32.

Mounting plate 119 also serves as a support member for circuit board 64. During assembly of control module 40, the leads to the low side FETs 84*a*-84*c* are typically wire bonded (ultrasonically) to the printed circuit board 64. During this operation, the mounting plate 119 functions as the backing member that prevents the printed circuit board 64 from vibrating.

A generally cylindrical insert 122 extends laterally inward from the top of front plate 92. Insert 122 is seated in a bore formed in the front plate 92 (bore not identified). The insert 122 is formed with a closed end threaded bore 123, (shown in phantom) that extends inwardly from the exposed face of the insert. When control module 40 is seated in tool housing 32, a fastener (not illustrated) fitted in bore 123 holds the module in position.

As seen by FIG. 3C, insert 122, like the distal end section 121 of mounting plate 119, projects a slight distance distally forward of front plate 92. Thus, insert 122, like mounting plate 119, functions as a spacer to prevent module front plate 92 from abutting the adjacent inner wall of the tool housing 32.

Insert 122 is further formed so to have a planar surface 124. Surface 124 is coplanar with the longitudinal axis of the control module 40. A post 125 integral with the insert 122 projects away from surface 124. When the control module 40 is assembled, printed circuit board 64 is disposed over insert surface 124. Insert 122 thus serves as a mounting bracket for holding the printed circuit board 64 in the control module 40. Post 125 extends through an opening in the circuit board 64 (opening not identified). A locking pin retainer (not illustrated) disposed over the post 125 that presses against the circuit board 64 holds the circuit board to the post. In some versions of the invention, the function of the retainer is performed by a solder connection.

Control module 40 has two additional tabs 126 and 127 that support circuit board 64. Tab 126 is mounted to the inside of front plate 92 between the two openings 107. Tab 127 is located at the corner formed by the junction of top plate 94 and back plate 98. Both tabs 126 and 127 are provided with posts 130 over which the circuit board 64 and to which a circuit board-securing fastener is attached. Alternatively, the circuit board is soldered to tabs 126 and 127.

A push pad 131 is mounted to the outer face of the back plate 98 adjacent top plate 96. When surgical tool 30 is assembled, a set screw (not illustrated) extends from the tool housing 32 against the push pad 131 to facilitate in the positioning of the control module 40. Push pad 131 services as a reinforcing member that distributes the force imposed by the set screw.

A tab 99 extends perpendicularly outwardly from back plate 98. The tab 99 is adjacent bottom plate 96. The tab 99 is formed with an opening, not identified. Tab 99 serves as a bracket for receiving a fastener (not illustrated) used to hold the console in the handle 38.

FIG. 4B illustrates how sensors 74 and 76, the sensors that monitor the operation of motor 34, are mounted to the printed circuit board 64. Sensor 74, the primary sensor, is mounted in a notch 132 formed in the top of the circuit board 64. Sensor 74 is tightly seated in notch 132. This arrangement minimizes the likelihood that, if tool 30 is subject to extreme mechanical shock, for example, dropped, the mechanical moment will cause sensor 74 to shift relative to the motor 34. Locking of the sensor 74 in place ensures the signals generated by the sensor accurately represent motor rotor position.

In some versions of the invention, individual pockets, indentions, are formed in top plate 94 for receiving the individual sensors 74 and 76. These pockets can be formed by half shear punching out of the workpiece forming the top plate. During assembly of the control module, each sensor 74 and 76 is seated in the appropriate pocket. The pockets functions as nests in which the individual sensors are seated. The void spaces of the pockets also position the sensors closer to the motor rotor than if the sensors where merely disposed against the inner planner surface of the top plate 94.

Sensor 76 is mounted to printed circuit board 64 so as to be laterally aligned with and vertically spaced from sensor 74. In some versions of the invention, sensor leads 133 integral with sensor 76 (one lead shown) serve a secondary function as mounting posts that hold the sensor 76 above the circuit board 64 so the two sensors 74 and 76 are aligned in a line perpendicular to both the plane and longitudinal axis of the circuit board 64. For reasons apparent below, minor position shifts of sensor 76 will not adversely affect operation of the surgical tool 30.

Figure 5:
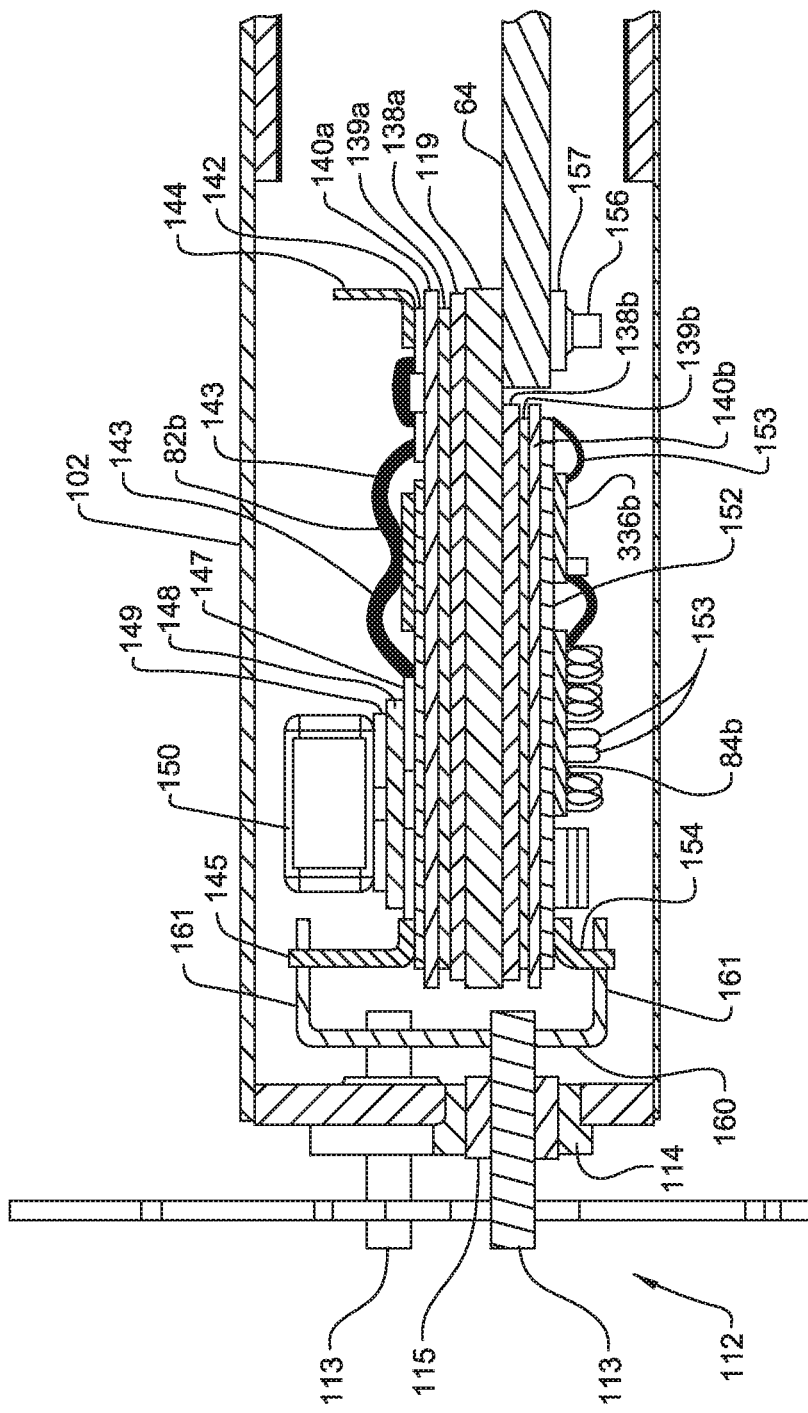
FIG. 5 is a cross-sectional view illustrating how the power FETs are mounted to the control module.

A detailed explanation of how FETs 82*a*-82*c* and 84*a*-84*c* are secured to mounting plate 119 is now provided by reference to FIG. 5. As mentioned above, mounting plate 119 functions as both the support structure for FETs 82*a*-82*c* and 84*a*-84*c* and the heat sink for the thermal energy generated by these and certain other components. Copper/molybdenum laminate structures 138*a* and 138*b* are bonded, respectively, to the opposed top and bottom faces of plate 119. Insulating layers 140*a* and 140*b* are disposed over the copper/molybdenum layers 138*a* and 138*b*, respectively. In actuality, copper/molybdenum layers 139*a* and 139*b* are bonded to the faces of layers 140*a* and 140*b*, respectively, which are bonded to copper molybdenum layers 138*a* and 138*b*. This means a copper-molybdenum laminate 139*a* or 139*b* is soldered brazed or otherwise secured to each copper/molybdenum laminate layer 138*a* or 138*b* of the mounting plate 119. This ensures that interfaces components of mounting plate 119 and insulating layers 140*a* and 140*b* have identical thermal coefficients of expansion.

A copper/molybdenum laminate trace layer 142 is applied to the exposed face of insulating layer 140*a*. The high side FETs 82*a*, 82*b* and 82*c* are attached to the exposed face of insulating layer 140*a*. Wires 143 and the FET leads 83 establish the electrical connections between the FETs 82*a*, 82*b* and 82*c* and the individual traces. L-shaped brackets 144 (one shown) are mounted over the traces of layer 142 at the upper end of the insulating layer 140*a*, the end directed towards module top plate 94. Brackets 144 are the structural elements to which wires that electrically connect traces on circuit board 64 to the traces of layer 142 are connected (wire connections not shown). L-shaped brackets 145 (one shown) are mounted over the traces of layer 142 at the bottom end of the insulating layer 140*a*, the end adjacent module bottom plate 96. Brackets 145 are the conductive components through which signals are exchanged with driver/signal pin assembly pins 113.

A set of filter capacitors 150, (one shown) are also disposed over the traces of layer 142. Filter capacitors 150 remove AC components from the output signal from battery 42. The filter capacitors 150 are disposed over a common insulating layer 148 also formed of a ceramic material.

Copper-molybdenum trace layers 147 and 149 are disposed, respectively, on the lower and upper surfaces of insulating layer 148. The traces of the lower layer 147 establish electrical connections with the physically adjacent traces of layer 142. The traces of upper layer 149 provide the electrical connections to capacitors 150. Not shown are the vias through insulating layer 148 that connect the traces of layers 147 and 149.

The exposed face of insulating layer 140b, the face directed towards lid 104 in FIG. 5A, is provided with a copper molybdenum trace layer 152. Low side FETs 84a, 84b and 84c are disposed over the exposed face of insulating layer 140b and the traces of layer 152. Conductors 153 establish connections between the FETs 84a-84c and the traces of layer 152. In some versions of the invention, plural conductors 153 extend from the exposed face of each FET 84a-84c, which is the FET source to an adjacent trace of layer 152. The plural conductors 153 establish a common ground plane for the FETs 84a-84c.

Also mounted to the exposed face of insulating layer 140b and over the conductive traces of layer 152 are current sense FETs 336a, 336b and 336c, (one shown). Wires 154 connect the leads of the current sense FETs 336a-336c to the traces of layer 152. L-shaped brackets 154 (one shown) are disposed over the traces of layer 152 at the bottom end of the insulating layer 140b. Brackets 154 are the conductive components through which signals are exchanged with driver/signal pin assembly pins 113.

Copper molybdenum layers 138b and 139b, insulating layer 140b, trace and trace layer 152 do not extend to the top end of mounting plate 119. Instead, the top end of the undersurface of plate 119, the surface directed towards lid 104, is exposed. During assembly of control module 40, the bottom end of circuit board 64 is placed over this exposed surface of plate 119. This end of plate 119 is provided with two mounting pins 156, (one shown). When printed circuit board 64 is positioned on plate, 119, pins 156 seat in openings formed in the circuit board, (openings not identified). Lock pin retainers 157 (one shown) fitted over the circuit board 64 and around the pins 156 hold the circuit board in position. In some versions of the invention, solder is employed to secure circuit board 64 to pins 156. This eliminates the need to provide the retainers.

A U-shaped connector bracket 160 is mounted over each driver/signal pin assembly pin 113. Shown in cross section in FIG. 5 is the opening formed in the center web of the bracket 160 in which the pin 113 is press fit or otherwise conductively secured (opening not identified). Bracket 160 is formed to have opposed, parallel, upwardly extending legs 161. A first one of the legs 161 extends above trace layer 142 and terminates close to one of the filter capacitors 150. The opposed leg 161 of each bracket extends over trace layer 152.

The two spaced rows of pins 113 and the brackets 160 are shaped such that each bracket 160 can be used to establish the conductive connections pins 113 in either the upper row or lower row. Thus, the bracket 160 shown in cross section in FIG. 5 can be placed over the upper of the two pins in the Figure, rotated from 180°, and its legs 161 will then be appropriately positioned.

The free end of each leg 161 is formed with a center opening 162 (FIG. 3D). When control module 40 is assembled, each leg opening 162 disposed over trace layer 142 seats over the adjacent one of the brackets 145. Each leg opening 162 disposed over trace layer 152 seats over the adjacent one of the brackets 154.

C. Electrical Features

FIGS. 6A-6E illustrate the circuit internal to control module 40 that regulates actuation of the motor 34. In general, the signals produced by sensors 66-76 are applied to a processor, in FIG. 6A, a digital signal processor (DSP) 170. Based on the signals generated by sensors 66 and 70, the DSP 170, selectively causes the circuit to transition from a power saving "sleep" mode to an "active" mode in which the circuit energizes the motor 34. Based on the signals generated by sensors 68 and 72, DSP 170 generates output signals indicating both the speed and direction in which the motor 34 should be run. Sensors 74 and 76 generate basic signals representative of position of the motor rotor 78. The DSP 170, based on these signals, generates additional signals that indicate rotor position.

The speed and direction instruction signals and motor rotor position signals generated by DSP 170 are applied to a motor control chip (MCC) 172. The MCC 172, based on the DSP-generated signals, selectively gates power FETs 82a-82c and 84a-84c. The MCC 172 also monitors the current drawn by the motor 34. Actuation of the motor 34 by the MCC 172 is further based on the speed at which it operates and the current it draws.

In more detail, also internal to the control module 40 are two voltage regulators 174 and 176. A first one of voltage regulators, regulator 174, outputs digital Vdd signals and analog Vdda signals that are supplied to the other components internal to module 40. In one version of the invention, the nominal level of the Vdd and Vdda signals are at 3.3 Volts. Voltage regulator 174 continually outputs the Vdd and Vdda signals regardless of the sleep/active state of the handpiece 30. Voltage regulator 176 outputs a Vcc signal applied to the other components internal to the module 40. In one version of the invention the Vcc signal is at 12 Volts. Voltage regulator 176 is normally in a deactivated state. When voltage regulator 176 is in this deactivated state, the whole of the control circuit is in the sleep mode. Only when one of the trigger switches 46 or 47 is depressed to actuate the handpiece 30, does voltage regulator 176 transition to the active state. This transition results in the whole of the control circuit transitioning from the sleep mode to the active mode.

The positive terminal of the battery 42 is connected to both voltage regulators 174 and 176. In the illustrated version of the invention, the battery positive terminal is connected to a forward biased diode 177. The cathode of diode 177 is connected to two parallel connected resistors 178 and 180. The signal present at the opposed junction of resistors 178 and 180 is applied to both voltage regulators 174 and 176 as the Vin signal. In some versions of the invention, a single resistor performs the function of resistors 178 and 180. In the application, the voltage present at the positive terminal of battery 42 is the BATT+ signal.

In one version of the invention, an LT1765EFE-3.3 3 Amp 1.25 MHz Step-Down Switching Regulator available from the Linear Technology Corporation of Milpitas, Calif. is employed as voltage regulator 174. A capacitor 182 is tied between the Vin input of this voltage regulator 174 and ground. A capacitor 184 and series connected resistor 186 are tied between the Vc pin of voltage regulator 174 and ground. A capacitor 188 is tied across capacitor 184 and resistor 186. Other ground connections of the pins of the voltage regulator 174 to ground are not specifically described.

The output voltage from voltage regulator 174 is obtained from the Vsw pin. The output signal is applied to an inductor 190. The voltage present at the end of inductor 190 distal from the voltage regulator 174 is the Vdd voltage. The voltage present at the distal end of inductor 190 is applied through a forward biased diode 192 to the boost pin of the voltage regulator. A capacitor 194 is tied between the Vsw pin of the voltage regulator 174 and the cathode of diode 192. A rectifying diode 196 is forward bias connected between ground and the Vsw pin of voltage regulator 174. An inductor 198 is connected to the distal end of inductor 190. The voltage present at the end of inductor 198 distal to voltage regulator 174 is the Vdda voltage. A capacitor 202 is connected between the junctions of inductors 190 and 198 and ground. The voltage present at the junctions of inductors 190 and 198, the Vdd voltage, is applied back to the voltage regulator 174 as the feedback voltage.

In one version of the invention, the LT3436 3 Amp, 800 kHz, Step-Up Switching Regulator, also from Linear Technologies, is employed as voltage regulator 176. A capacitor 206 is tied between the ground the Vin pin of voltage regulator 176. A voltage suppression diode 208 is also tied between ground and the Vin pin of voltage regulator 176. Diode 208 prevents transient voltages from being applied to the Vin pins of both voltage regulators 174 and 176. A capacitor 209 and series connected resistor 210 are connected between the Vcc pin of voltage regulator 176 and ground. A capacitor 212 is tied across capacitor 208 and resistor 210. Other ground connections to the pins of voltage regulator 176 are not discussed.

The output voltage of the voltage regulator 176 is based on the signal at the Vsw pin. This signal is applied to a capacitor 214 and a series connected, forward biased diode 216. The signal present at the cathode of diode 216 is the Vcc signal. Capacitor 217 connected between the cathode of diode 216 and ground filters AC components from the Vcc signal. The signal applied to the Vin pin of voltage regulator 176 is applied to the Vsw pin of the voltage regulator through an inductor 218. The signal present at the junction of capacitor 214 and diode 216 is tied to ground through an inductor 220. The signal present at the cathode of diode 216 is applied to ground through a voltage divider consisting of series connected resistors 222 and 224. The voltage present at the junction of resistors 222 and 224 is applied back to the feedback pin of voltage regulator 176.

An alternative voltage regulator 176 is the LM3478MM available from National Semiconductor. This voltage regulator requires a separate external FET (not illustrated) for selectively tying inductor 220 to ground.

An AWAKE signal digital signal from DSP 170 is selectively applied to voltage regulator 176. The AWAKE signal, which is asserted high, is applied to a $\overline{\text{SHDN}}$ pin on the voltage regulator. The assertion of the AWAKE signal actuates voltage regulator 176. The negation of the AWAKE signal causes voltage regulator 176 to cease outputting the Vcc signal.

Sensors 66 and 70 each output a bi-state, digital signal as a function of the proximity of the associated magnets 56 and 58, respectively. In one preferred version of the invention, A3213LUA Hall effect switches available from Allegro Microsystems of Worchester, Mass., function as sensors 66 and 70. The Vdd signal is applied to the supply pin of each sensor 66 and 70. The ground pin of each sensor 66 and 70 is tied to ground. The output pins of sensors 66 and 70 are tied to a common input pin of DSP 170. In some versions of the invention, these output pins are tied to separate input pins of the DSP 170.

Sensors 68 and 72 each output an analog signal as function of the proximity of the associated magnet 56 and 58, respectively. In one version of the invention, the SS495A Ratiometric Linear (Hall) sensors available from Honeywell Sensing and Control of Freeport, Ill. are employed as sensors 68 and 72. A 5 Volt signal is applied to the Vs supply pin of each sensor 68 and 72. The V-pin of each sensor 68 and 72 is tied to ground. The output signals from sensors 68 and 72 are applied to separate analog signal input pins of the DSP 170. Each output signal from the sensor 68 or 72 is applied to the DSP 170 through a separate resistor 230. A capacitor 232 is tied between the end of each resistor 230 adjacent the DSP 170 and ground. A zener diode 233 is also tied between the output pin of each sensor 68 and 72 and ground, cathodes directed to the DSP 170. Zener diodes 233 protect DSP 170 from high voltage signals emitted by sensors 68 and 72. These high voltage signals may be generated if the sensors are exposed to a reverse polarity magnetic field.

Sensor 74 is identical to sensors 68 and 72. The Vs pin of sensor 74 is tied to the 5 Volt voltage source; the V-pin is tied to ground. The output signal of sensor 74 is applied through a resistor 234 to the inverting input of an amplifier 236. A capacitor 238 is tied between the inverting input of amplifier 236 and ground. Feedback to the amplifier 236 is supplied by a resistor 240 tied between the output of the amplifier and the inverting input. A reference signal is applied to the noninverting input of amplifier 236. In the illustrated version of the invention, the reference signal is signal is supplied from the center of a voltage divider consisting of series connected resistors 242 and 244. The free end of resistor 242 is connected to the 5 Volt source. The free end of resistor 244 is tied to ground. Resistors 242 and 244 are selected so that reference voltage is typically between 1.5 and 3.0 Volts. The output signal produced by amplifier 236 is applied to an analog input of DSP 170.

In the illustrated version of the invention, sensor 76 is identical to sensor 74. The output signal from sensor 76 is applied through a resistor 246 to the inverting input of an amplifier 248. A capacitor 250 is tied between the inverting input of amplifier 248 and ground. A resistor 252 tied between the output of amplifier 248 and the inverting input supplies the feedback. The reference signal applied to the noninverting input of amplifier 236 is supplied to the noninverting input of amplifier 248. The output signal generated by amplifier 248 is applied to a distinct analog input of DSP 170.

In one version of the invention, amplifiers 236 and 248 are both formed from MAX4247 Ultra-Small, Rail-to-Rail I/O With Disable Single/Dual-Supply, Low-Power Operation Amplifier available from the Maxim Company of Sunnyvale, Calif. Not shown are where the Vdd signal is applied to each amplifier 236 and 248. Also, a capacitor, (not illustrated) is tied between the Vdd pin of amplifier 236 and ground. LMV982 amplifiers available from National Semiconductor may also be used as amplifiers 236 and 248.

Amplifiers 236 and 248 each have a $\overline{\text{SHDN}}$ pin to which an activation signal is selectively applied. The AWAKE signal from the DSP 170 is selectively applied to the $\overline{\text{SHDN}}$ pins to regulate the on/off state of the amplifiers 236 and 248.

In one version of the invention the MC56F8322 16-Bit Hybrid Controller from Freescale Semiconductor of Chandler, Ariz. is employed as the DSP 170. DSP 170 powered by the Vdd and Vdda signals. Not shown are the capacitors that filter the Vdd and Vdda signals applied to the DSP 170. DSP 170 receives as inputs the above five described signals from sensors 66-76. DSP 170 also monitors the filtered voltage out of battery 42. Specifically, the BATT+ signal is applied to an analog input pin of the DSP 170 through a voltage divider consisting of series connected resistors 258 and 260. The BATT+ signal is applied to the free end of resistor 258. The free end of resistor 260 is tied to ground. A capacitor 262 is tied across resistor 260. The voltage present at the junctions of resistor 258 and 260 is applied to an analog input pin of DSP 170. Capacitor 260 thus filters the divided down BATT+ signal before it is applied to the DSP 170 for monitoring.

The DSP 170 also receives as an input an indication from the MCC 172 when the motor 34 draws an excessive amount of current. Specifically, the MCC 172 generates a maximum current (I_LMT) signal to the DSP 170 when the current drawn by motor 34 exceeds a set amount.

DSP 170 outputs five signals. The first signal output is the AWAKE signal. The AWAKE signal is asserted when the DSP 170 receives a signal from either sensor 66 or sensor 70 that the magnet 56 or 58, respectively, associated with the sensor is proximally displaced from the most distal position. This signal represents the depression of the associated trigger switch 46 or 47 to actuate the handpiece 30.

The second and third signals output by DSP 170 are respectively, FORWARD (FWD) and REVERSE (REV) signals. These signals are output as a function of the output signals generated by sensors 68 and 72. Generally the actuation of a separate one of the trigger switches 46 or 47 results in the outputting of a separate one of the FORWARD or REVERSE signals. THE FORWARD and REVERSE signals are applied to the MCC 172.

As explained below, though, there is no set relationship between which trigger switch 46 or 47 is depressed to cause a specific one of the FORWARD or REVERSE signals to be output. Depending on how the handpiece 30 is selectively configured, one presses either one of the trigger switches 46 or 47 to cause the FORWARD signal to be output. Similarly, based on the temporary configuration of the handpiece 30, in order to cause the REVERSE signal to be asserted, either trigger switch 46 or 47 is depressed. Depending on handpiece configuration, simultaneous depression of the both trigger switches 46 and 47 can result in simultaneous assertion of the FORWARD and REVERSE signals. Handpiece 30 may further be configured so that depression of one of the trigger switches 46 or 47 causes the FORWARD and REVERSE signals to be simultaneously asserted.

The fourth signal output by DSP 170 is a set of Hall signals, HALLx signals in the Figures, representative of signals representative of the angular position of the motor rotor 78. The HALLx signals are equivalent to the signals generated if traditional digital Hall sensors mounted in the motor 34 generate signals representative of rotor position. DSP 170 normally outputs the HALLx signals as a function of the signal received from sensor 74. At start-up, the output HALLx signals are further a function of the signal output by sensor 76. The HALLx signals are applied to the MCC 172.

The fifth signal output by DSP 170 is a USER_SPEED (U_S) signal. The USER_SPEED signal is generated as a function of the signal received from the sensor 68 or 72 associated with the most fully depressed trigger switch 46 or 47, respectively. In the described version of the invention, the USER_SPEED signal is an analog signal. The process steps DSP 170 executes in order to, based on the signal from the sensor 68 or 72, generate the USER_SPEED signal are discussed below.

Motor control circuit 172 is an application specific integrated circuit. Generally, MCC 172 based on states of the FORWARD, REVERSE, USER_SPEED, and HALLx signals, generates the signals necessary to gate FETs 82a-82c and 84a-84c to cause the appropriate actuation of the motor 34. A detailed understanding of the motor control sub-circuits internal to MCC 172 is obtained from the Applicant's U.S. Pat. No. 6,025,683, MOTOR CONTROL CIRCUIT FOR REGULATING A DC MOTOR, issued 15 Feb. 2000, the contents of which are incorporated herein by reference.

While a detailed understanding of a number of the sub-circuits internal to MCC 172 is provided in U.S. Pat. No. 6,025,683, the following understanding of the MCC 172 is provided by reference to FIGS. 6B and 7.

One sub-circuit internal to the MCC 172 is the direction controller 270. Direction controller 270 is the MCC 172 sub-circuit that receives the FORWARD and REVERSE signals from the DSP 170. As a function of the FORWARD and REVERSE signals, direction controller 270 selectively asserts a FORWARD/REVERSE (F/R) signal. If the FORWARD and REVERSE signals from the DSP 170 are simultaneously asserted, direction controller 270 cyclically asserts and negates the FORWARD/REVERSE signal. This, in turn, causes energization signals to be applied to the motor 34 so that rotor 78 oscillates back and forth.

Direction controller 270 includes a FET 272. The drain of FET 272 is tied to a resistor 344, (FIG. 6D) that is part of an off-chip current measuring circuit. As discussed below, the current measuring circuit generates a variable signal as a function of the current drawn by the motor 34. The source of FET 272 is tied to ground. Normally, direction controller 270 maintains FET 272 in an on state. When the motor is to be driven in an oscillator pattern, direction controller 270 also periodically gates FET 272 off. As discussed below, this causes the magnitude of the signal representative of the current drawn by motor 34 to change.

A tachometer 274 is also internal to the MCC 172. The tachometer 274 receives as input signals the HALLx signals from the DSP 170. Based on the HALLx signals, the tachometer 274 produces a constant on time pulse as a tachometer signal (TACH). The frequency with which the pulses are generated is representative of the rotational speed of motor 34.

The MCC 172 also includes a speed controller 276. The speed controller 276 receives as inputs the USER_SPEED signal and the TACH signal. Based on these signals, speed controller 276 produces a pulse width modulated SPEED_CONTROL (S_C) signal. Specifically, the USER_SPEED signal is applied from DSP 170 through a resistor 278, seen in FIG. 6B, to the speed controller 276. A capacitor 280 is tied between the MCC 172 pin through which the USER_SPEED signal is input and ground.

Internal to the speed controller 276 is an operational amplifier, not illustrated. The USER_SPEED signal is applied to the noninverting input of this amplifier. The TACH signal is applied to the inverting input of the amplifier. This signal is applied to the amplifier through an off-chip resistor 282. The output signal of this amplifier is also applied as a feedback signal to the amplifier inverting input. This signal is feedback through a resistor 284. A capacitor 286 is tied across resistor 284. A DC voltage is also applied to the inverting input of the speed control operational amplifier. This voltage is taken from a voltage divider consisting of series connected resistors 288 and 290. The free end of resistor 288 is connected to the 5 Volt supply. The free end of resistor 290 is tied to ground. The voltage present at the junction of resistors 288 and 290 is applied to the inverting input of the speed controller amplifier through a resistor 292. This amplifier and the other components of speed controller 276 cooperate to generate a SPEED_CONTROL (S_C) signal. The SPEED_CONTROL signal is a pulse width modulated signal. The on duty cycle of the SPEED_CONTROL signal is proportional to the difference between the user-selected speed and the measured speed of the motor 34.

Speed controller 276, also selectively asserts a digital BRAKE_ENABLE (B_E) signal. The BRAKE_ENABLE signal is asserted whenever the output signal from the operational amplifier indicates the motor rotor 78 is turning at a rate significantly greater than the user-desired speed.

Figure 7:
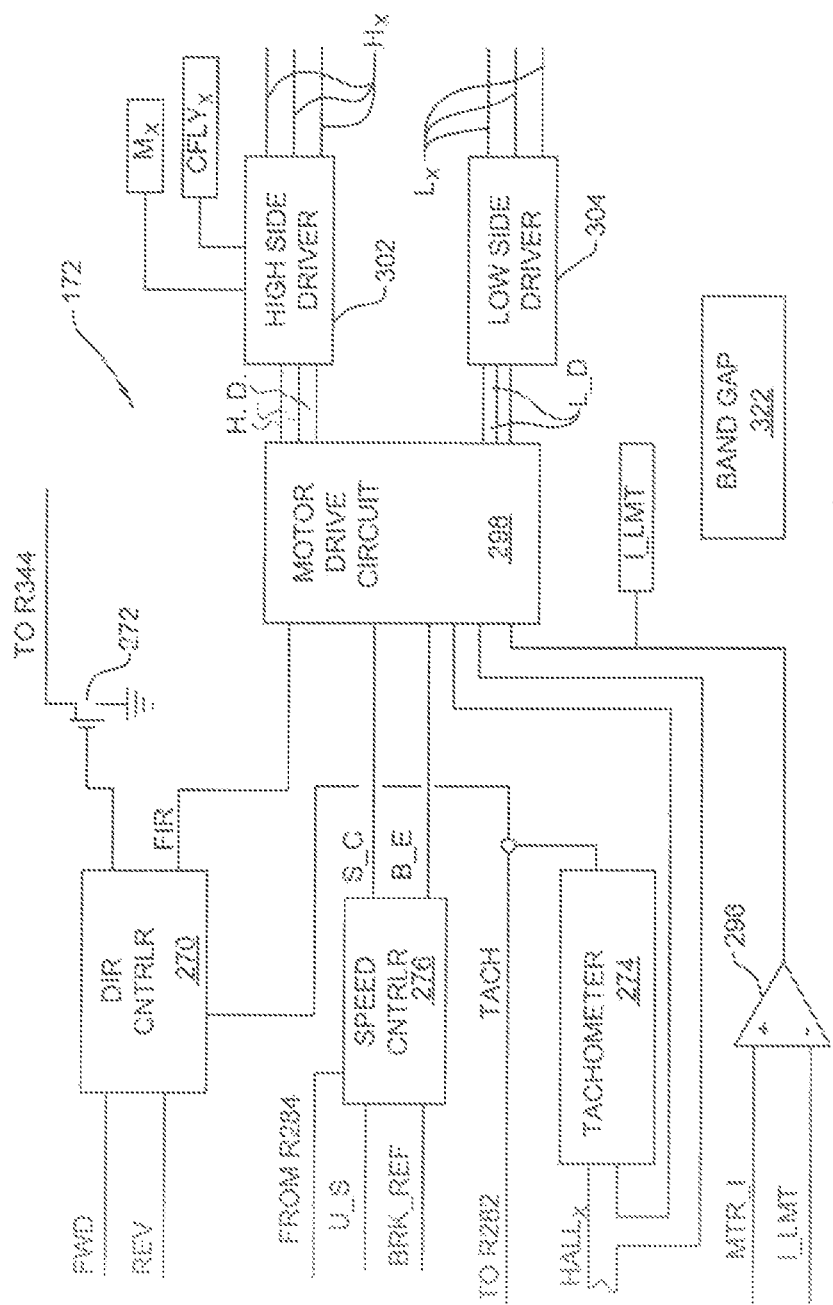
FIG. 7 is a block diagram of the main sub-circuits that form the motor control circuit.
Figure 8A:
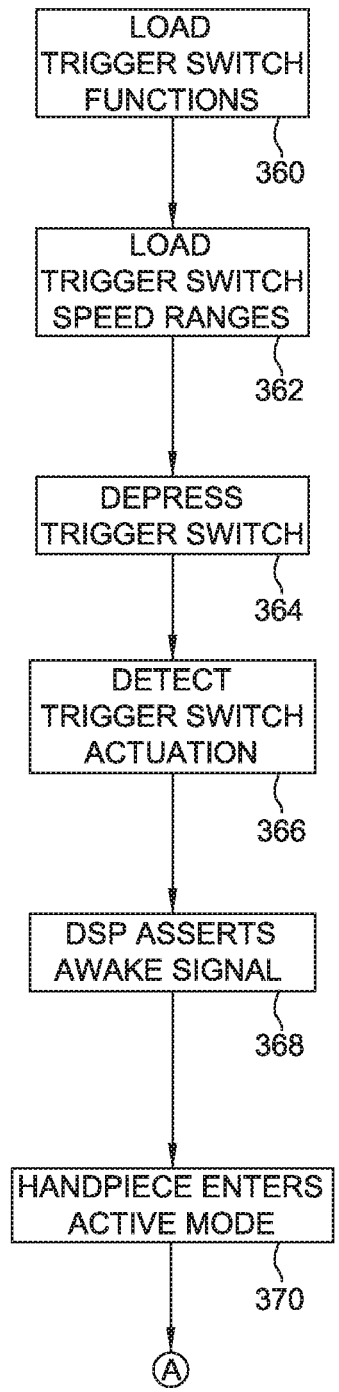
FIGS. 8A, 8B, 8C and 8D collectively form a flow chart of the process steps executed by the components internal to the tool upon actuation of the tool.
Figure 8B:
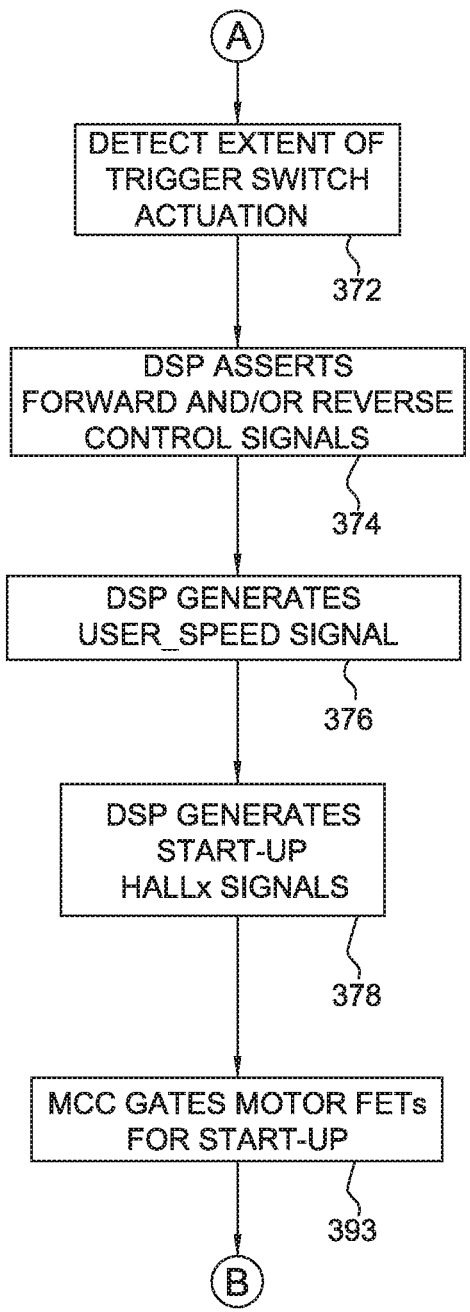
Figure 8C:
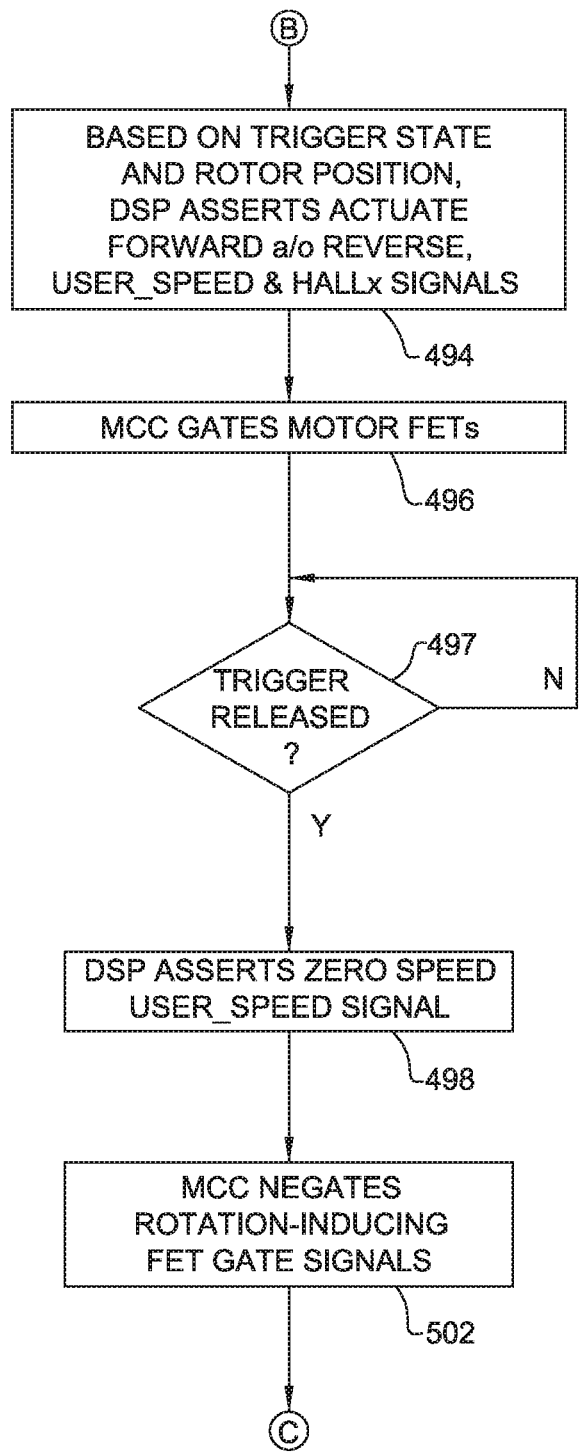
Figure 8D:
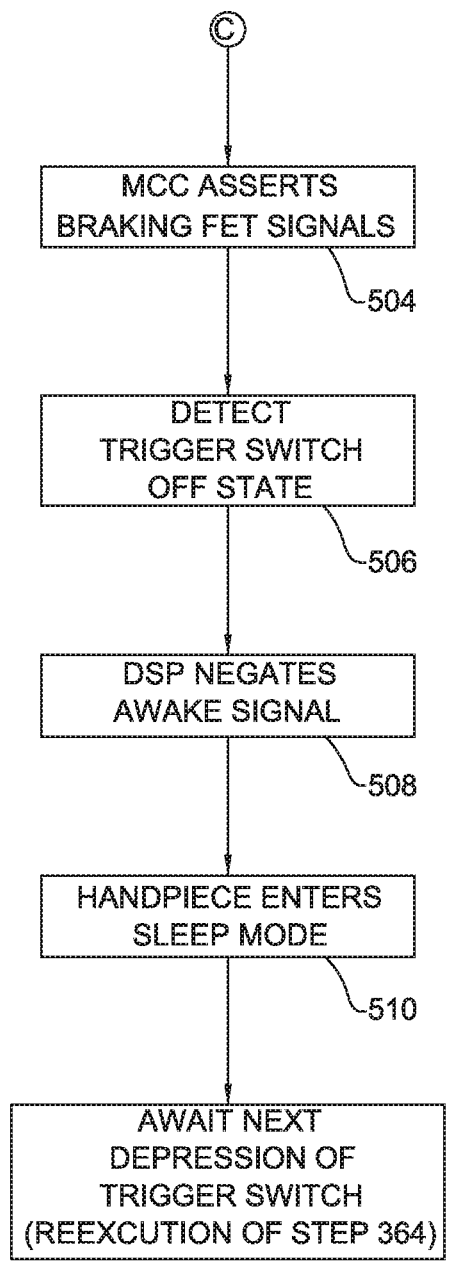

In FIG. 7, the BRAKE_ENABLE signal is shown as being applied directly to a motor drive circuit 298. This is for purposes of simplicity. In practice, the BRAKE_ENABLE signal may be applied to the direction controller 270. The direction controller 270 serves as the actual sub-circuit that asserts the BRAKE_ENABLE signal to the motor drive circuit 298. This construction makes it possible for the direction controller 270 to, when the motor 34 is to be driven in oscillatory mode, cyclically assert the BRAKE_ENABLE signal. This reduces tool vibration when motor 34 is oscillated.

A current monitor 296, again part of the MCC 172, monitors the current drawn by the motor 34. Current monitor 296 is essentially a comparator. When the current limit exceeds a set limit, current monitor 296 asserts a current limit (I_LMT) signal. This I_LMT signal is the signal asserted to the DSP 170.

The motor drive circuit 298, also integral with the MCC 172 asserts the basic trigger signals that gate FETs 82a-82c and 84a-84c. Motor drive circuit 298 receives as input signals, the S_C signal, the F/R signal, the BRAKE_ENABLE signal, the HALLx signals and I_LMT signal. Based on these signals motor drive circuit 298, asserts three (3) high drive H_D signals and three (3) low drive L_D signals. The H_D signals are asserted to individually gate FETs 82a-82c, the FETs that tie the windings 86a-86c, respectively, to the BATT+ voltage. The L_D signals are asserted to individually gate FETs 84a-84c, the FETs that tie the windings 86a-86c, respectively, to the BATT− ground.

Motor control circuit 172 also includes high side drivers 302 and low side drivers 304. Each H_D signal is applied to a specific one of the high side drivers 302, collectively shown as a single block. Each high side driver 302, in response to receipt of the associated H_D signal, asserts a high side control (Hx) signal to the gate of associated one of the FETs 82a, 82b or 82c. Each Hx high side control signal is applied to the associated FET 82a, 82b or 82c through a distinct conductor 308.

The actual H1, H2 or H3 signal applied to each FET 82a, 82b or 82c, respectively, is applied to the FET's gate through a resistor 315. The drain of each FET 82a-82c is tied to the BATT+ terminal of the battery 42. The source of each FET 82a, 82b and 82c is tied to a separate one of the windings 86a, 86b and 86c.

A boost signal from a flyback circuit is applied to the gates of FETs 82a, 82b and 82c to ensure they are forward biased relative to the complementary sources. Each flyback circuit consists of a diode 310 to which the Vcc signal is applied. This signal is applied to a capacitor 312. The opposed end of the capacitor is tied to the winding to which the associated FET 82x is attached. In FIGS. 6B, 6C and 6D, the M1, M2, M3 conductors are shown extending to windings 86a, 86b and 86c, respectively. A zener diode 314 is reverse bias connected between each Hx line and the associated Mx line.

A boost circuit, part of the flyback circuit and contained in the high side drive circuit 302, triggers the outputting of the boosted gate signal. Specifically, when each winding 86a, 86b, or 86c is tied to ground, charge builds across the associated capacitor 312. Capacitor 312, it is further observed, is connected to the high side circuit 302 through a CFLYx connection. The boost circuit internal to the high side drive circuit includes a FET, not illustrated, for regulating current flow from the capacitor. The signals on the Mx line serve as the reference signals for the boost circuit. When the winding is to be tied to the BATT+ terminal, the charge across the capacitor 312 is applied through the CFLYx connection and turned on boost circuit FET. This boosted signal is then output over Hx line to the gate of the appropriate FET 82a, 82b or 82c. Diodes 314 prevent burn out of the associated FET 82a, 82b or 82c if the gate to source voltage exceeds a specific level. In one version of the invention, this is 15 Volts. This prevents possible FET burnout due to the rotor being stalled. In this situation, there will not be any back EMF signals on the windings. In this situation, the voltage present at the sources of the FETs 82x can drop to near zero.

Each L_D signal is applied to a specific one of the low side drivers 304, collectively shown as a single block. When an L_D signal is applied to a low side driver 304, the driver 304 asserts a low side control signal (Lx) to the gate of the associated FET 84a, 84b or 84c. Each low side drivers 304 include a pair of series connected off-chip FETs, not illustrated. The drain of a first one of the FETs is tied to the Vdd voltage source. The source of the second FET is tied to an off chip Kelvin ground 318 (Conductor represented as KGND). The signal present at the junction of the source of the first FET to the drain of the second FET is the Lx low side control signal. The sources of the FETs 84a-84c that tie the windings 86a-86c to ground are also connected to Kelvin ground by a conductor 320.

The Lx signals asserted by each low side driver 304 are applied to the gate of a separate one of the FETs 84a, 84b or 84c through a resistor 321. The drain of each FET 84a, 84b and 84c is tied to a separate winding 86a, 86b and 86c, respectively. The sources of FETs 84a-84c are tied to the BATT− pin, the terminal to where the negative terminal of the battery 42 is connected.

Also internal to MCC 172 is a bandgap circuit 322. Bandgap circuit 322 functions as a temperature independent constant voltage source and a constant current source for the components internal to the MCC 172.

While not illustrated, it should be understood that MCC has 5 Volt regulated voltage source. This voltage source functions as the 5 Volt power supply for the other components internal to control module 40 including sensors 68, 72, 74 and 76, connections not shown. The output signal from this voltage regulator is applied to ground through series connected resistors 324, 326 and 328 seen in FIG. 6B. The voltage present at the junction of resistors 324 and 326 is applied to the speed controller 276 as a brake reference (BRK_REF) signal upon which the assertion of the BRAKE_ENABLE signal is based. The voltage present at the junction of resistors 326 and 328 is applied the current monitor 296 as a reference (I_REF) signal upon which the assertion of the I_LMT signal is based.

A capacitor 329 is in parallel across resistors 324, 326 and 328 and ground. The voltage present at the junction of resistor 324 and capacitor 329 is the filtered, voltage regulated 5 Volt reference signal.

A more detailed understand of the above circuits is presented in the aforementioned, incorporated by reference U.S. Pat. No. 6,025,683. In the circuit disclosed in this document, the bandgap regulator also functions as the 5 Volt regulated power supply.

The MCC 172 is powered by the Vcc signal produced by voltage regulator 176. The Vcc signal is applied to separate Vcc and DRVcc pins on the MCC 172. A capacitor 330 is tied between the Vcc pin and ground. A complementary analog ground pin on MCC 172 is tied to the ground of capacitor 330. A capacitor 332 is tied between the DRVcc pin and ground. A complementary digital ground pin on MCC 172 is tied to the ground of capacitor 332. The Vcc signal is also applied to a Vmm pin on MCC 172 through a resistor 333

As mentioned above, the control module 40 also includes a circuit for monitoring the current drawn by the motor 34. This circuit includes three FETs 336*a*, 336*b* and 336*c*. The drain of each FET 336*a*, 336*b* and 336*c* is tied to a separate one of the motor windings 86*a*, 86*b* and 86*c*, respectively. The L1, L2 or L3 low side control signals applied to the gate of each FET 84*a*, 84*b* or 84*c*, respectively, are applied to the gate of the complementary FET 336*a*, 336*b* or 336*c*, respectively. Thus, each time a FET 84*a*, 84*b* or 84*c* is turned on, the complementary FET 336*a*, 336*b* or 336*c*, respectively, is likewise turned on.

The sources of FETs 336*a*-336*c* are connected to a common resistor 338. The free end of resistor 338 is tied to ground through a resistor 340. The voltage present at the junction of resistors 338 and 340 is applied to the MCC current monitor 296 as MTR_I signal representative of current drawn by the motor 34. A capacitor 342 connected across resistor 340 filters this signal Resistor 344 is also connected at one end to the junction of resistors 338 and 340. The second end of resistor 344 is connected to the drain of FET 272. Normally, when FET 272 is gated on, the signal across resistor 338 flows to ground through the parallel paths of resistor 340 and 344. Thus, normally, the MTR_I signal is based on a relatively low volts/current ratio.

When the motor 34 is driven in an oscillatory mode, direction controller 270 gates FET 272 off for an initial period of time after the FORWARD/REVERSE is toggled. This effectively disconnects resistor 344 from the current measuring circuit. The MTR_I signal is then based on relatively high volts/current ratio. This, in turn, causes the current monitor 296 to assert the I_LMT signal more rapidly than it would otherwise be asserted. The rapid assertion of the I_LMT signal, in turn, causes the less frequent application of energization signals to the motor 34. This reduces initial motor acceleration. The reduction of motor acceleration, in turn, reduces the counter torque the handpiece 30 initially produces. This "counter-torque" is torque opposite the torque the handpiece produces as a consequence of the motor rotating in a first direction. The minimization of the counter torque reduces the kick the handpiece produces in the hand of the user as the motor shifts rotation from a first direction to a second direction.

D. Tool Operation

The operation of surgical tool 30 of this invention is now explained by reference to the flow chart of FIGS. 8A-8D. Prior to actuation of the handpiece 30, the DSP 170, in step 360, is provided with instructions that identify the command signals each trigger switch 46 and 47 are to generate. For example, based on surgeon preference, either trigger switch 46 or 47 is set to be the switch that is depressed to cause the handpiece motor to run in the forward direction. The remaining trigger switch 47 or 46 is set to be the one depressed to run the switch in the reverse direction.

Alternative trigger switch settings are possible. For example, one trigger switch 46 or 47 may be set so that its depression causes the motor to run in the forward direction; the second trigger switch 47 or 46 is set so that its depression causes the motor to run oscillatory pattern. In still another configuration, the handpiece 30 is set so that depression of either trigger switches 46 or 47 causes the motor to run in the forward direction. As discussed below, the handpiece may be so set so that full depression of switch 46 causes motor 34 to run at a first speed; full depression of switch 47 causes motor 34 to run at a second speed. In another alternative configuration, the handpiece 30 is set so that depression of one trigger switch 46 or 47 causes the motor to run in the forward or reverse direction. In this configuration, the second trigger 47 or 46 switch is set to an inactive state; depression of this switch does not result in any actuation of the handpiece motor 34.

Thus step 360 is the loading into the DSP 170 instructions indicating which signal, FORWARD, REVERSE or oscillation between the two, the DSP should generate upon detection that a particular trigger switch 46 or 47 is depressed.

Prior to operation of the handpiece 30, in step 362, the DSP 170 is also loaded with instructions indicating the range of the USER_SPEED signal that is to be generated as a function of the extent to which the specific trigger switch 46 or 47 is depressed. This range is a function of variables such as surgeon preference, type of cutting accessory attached to the handpiece, and type of the surgical procedure being performed. For example, based on the preferences of one surgeon, the trigger switches may be set so that trigger switch 46 is the switch that is depressed to cause the motor to run in the reverse direction and when the switch is fully depressed the motor will run at a maximum of 25,000 RPM. The same surgeon sets DSP 170 so that full depression of trigger switch 47 causes the motor 34 to run in the reverse direction and the maximum speed the motor will run when so actuated is 15,000 RPM.

A second surgeon sets DSP 170 so that depression of either trigger switch 46 or 47 causes the motor to run in the forward direction. This surgeon more specifically sets handpiece 30 so that when trigger switch 46 is fully depressed, the motor runs at a maximum of 30,000 RPM and, when trigger switch 47 is fully depressed, the motor runs at a maximum of 7,500 RPM.

Also, as part of step 362, the minimum speed at which the motor 34 is run may also be actuated. Thus, a surgeon may set the handpiece so that when one of the trigger switches 46 or 47 is actuated, the motor runs in the forward direction at speeds between 5,000 and 25,000 RPM. When the second trigger switch 47 or 46 is depressed, the motor 34 runs in the forward direction at speeds between 10,000 and 13,000 RPM.

Steps 360 and 362, it should be recognized, are only performed if a particular surgeon wants to operate the handpiece in mode different from the mode defined by the default settings previously stored in the DSP 170. Typically, these default settings are loaded into the DSP 170 during the manufacturing process.

Prior to actual use of the handpiece, the DSP 170 maintains the components internal to control module 40 in the sleep mode. The AWAKE signal is not asserted. Thus, voltage regulator 176 does not output the Vcc signal. Since the Vcc signal is not output, the MCC 172 is in a deactivated state. Since the MCC 172 is deactivated, the MCC voltage regulator does not output the 5 Volt signal to the components to which it is otherwise applied. Sensors 68, 72, 74 and 76 are, therefore, inactive. Also deactivated are the analog to digital converters internal to the DSP 170 (converters not illustrated).

Even when the surgical tool 30 is in the sleep mode, voltage regulator 174 outputs the Vdd and Vdda signals.

Sensors 66 and 70 and DSP 170 are thus active even when the above-discussed tool components are in the sleep mode.

Depression of one of the trigger switches 46 or 47, step 364, results in the actuation of the handpiece 30. For purposes of illustration, discussion proceeds with the understanding that trigger switch 47 is the depressed switch. Initially, the movement of trigger switch 47, actually magnet 58, is detected by sensor 68, step 366. Consequently, in step 366, the output signal generated by sensor 68 undergoes a state change. DSP 170, upon detecting the change in state of the output signal from sensor 68, asserts the AWAKE signal, step 368.

Upon the assertion of the AWAKE signal 368, in a step 370, the remainder of the handpiece 30 enters the active mode. Specifically, the assertion of the AWAKE signal causes voltage regulator 176 to start to output the Vcc signal. The receipt of the Vcc signal energizes MCC 172. As a consequence of this energization, the MCC voltage regulator outputs the 5 Volt signal to the other components of the module 40 including sensors 68, 72, 74 and 76. Another sub-process of the sleep-to-active transition is the activation of the analog to digital converter block internal to the DSP 170.

As part of step 370, the AWAKE signal is also applied to the $\overline{\text{SHDN}}$ pins of amplifiers 236 and 246. Amplifiers 236 and 246 are thus enabled to produce amplified versions of the output signals generated by sensors 74 and 76, respectively. In practice it takes the components internal to control module 40 approximately 200 msec or less to transition from the sleep mode to the active mode. In more preferred versions of the invention, it should take 100 msec or less to undergo the transition. This is to minimize the extent to which the user may perceive a delay in tool start up.

Once the control module components are in the active mode, sensor 72 asserts a variable output signal based on the detected movement of magnet 58, step 372. Based on receipt of the signal from sensor 72, the DSP 170 engages simultaneously in steps 374 and 376. In step 374, based on the instruction data loaded in step 360, DSP 170 asserts the appropriate state FORWARD or REVERSE signal or a combination of these signals. If the handpiece 30 is set so that trigger switch 47 is the forward control switch then, in step 374, the DSP asserts the FORWARD signal. If trigger switch 47 is set to be the reverse control switch, the DSP asserts a REVERSE signal. Alternatively, if trigger switch 47 is set as the oscillating control switch, DSP 170 simultaneously asserts both the FORWARD and REVERSES signals.

In step 376, the DSP 170 generates the USER_SPEED signal. This signal is based on the instructions received in step 362 and the signal from sensor 72 representative of the extent to which magnet 58 has been displaced along its path of travel. When DSP 170 is programmed to vary the USER_SPEED linearly with the extent to which trigger switch 47 is actuated, the signal is determined according to the following formula $$\text{USER\_SPEED} = SPD_{MIN} + SS(SPD_{MAX} - SPD_{MIN}) \quad (1)$$

Here $SPD_{MIN}$ and $SPD_{MAX}$ are, respectively, the minimum and maximum speeds the motor 34 is to be run when trigger switch 47 is depressed. These are the coefficients supplied in step 362. The variable SS is the sensor signal from sensor 72, normalized from 0.00 to 1.00, representative of the extent to which trigger switch 47 is displaced from the extended to the retracted position.

As discussed below DSP 170 may be programmed to vary USER_SPEED in other than a linear relationship based on the displacement of the trigger switch.

In a step 378, which occurs near simultaneously with steps 374 and 376, the DSP 170 also generates HALLx signals representative of the position of the motor rotor 78. At start up, rotor speed 0 RPM, these data are based on signals from both sensor 74 and sensor 76. The basis for this determination is now explained by reference to the plots in the graph of FIG. 9. This graph illustrates the signals generated from the sensors 74 and 76 if the rotor is a two pole rotor. This is for the purposes of simplification. Thus, the output signal from sensor 74, plot 382, is a single sine wave over the 360° of rotation of the rotor.

In order for the MCC 172 to generate the Hx and Lx control signals in the appropriate sequence on motor start-up, the HALLx supplied from the DSP 170, must indicate within which sextant, 60° arc, the rotor 78 is located. If the signal from sensor 74 is between 0.866 and 1.00 it is clear that rotor is within the arcuate range of 60 to 120°. Similarly, if the signal from sensor 74 is between −0.866 and −1.0, it is clear that the rotor is within the arcuate range of 240 to 300°.

However, outside of these ranges, the single signal from sensor 74 does not, at start-up, accurately indicate rotor position. This is because outside of these two ranges, the single signal does not indicate where on the sine wave curve the rotor is located. For example, if the signal generated by sensor 74 is 0.5, it is not clear if the rotor is at the 30° position or the 150° position. On plot 382, these two positions are represented by points 384 and 386, respectively. Similarly, if the signal from sensor 74 is −0.71 it is not clear if the rotor is at the 225° position or the 315°. On plot 382 these two positions are represented by points 388 and 390, respectively.

Figure 9:
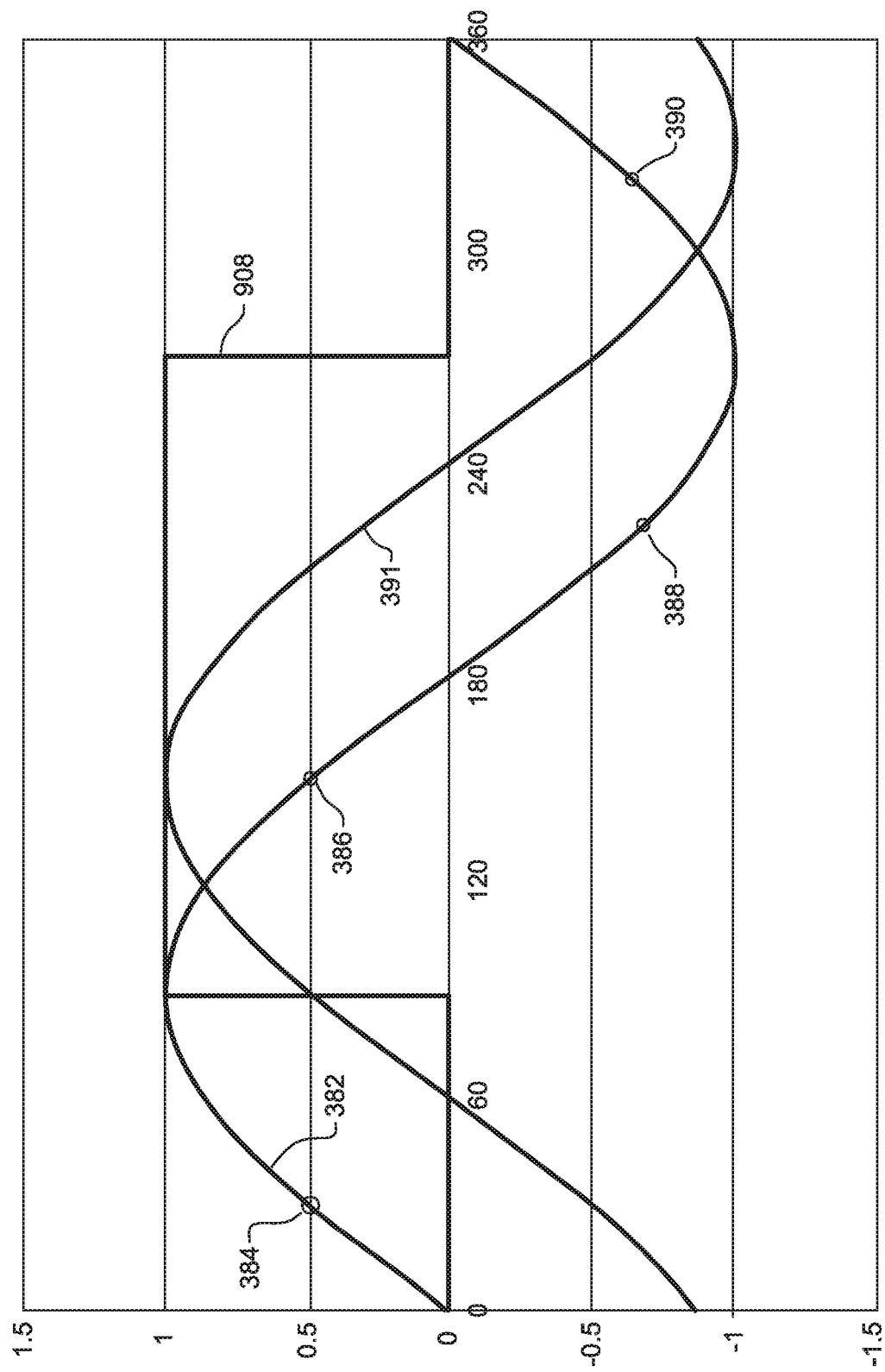
FIG. 9 are plots of the signals generated by the control module sensors that monitor the position of the motor rotor of the tool.

Thus, at start-up, in step 378, the DSP 170 employs the signals from both sensors 74 and 76 to generation an accurate determination of rotor position. In the illustrated version of the invention, since sensor 76 outputs an analog signal, this sensor is positioned in control module 40 to output a signal that is a maximum 60° out of phase behind the signal generated by sensor 74. In FIG. 9, the normalized signal output by sensor 76 is shown as plot 391.

In step 378, when the signal from sensor 74 outside of the ranges in which this signal alone can be used to determine rotor position one of two evaluations are performed. If the normalized output signal from sensor 74 indicates the rotor 78 is in either that 0 to 60° sextant or the 120 to 180° sextant, a test is made to determine if:

sensor 74 signal>sensor 76 signal

If this determination tests true, then, collectively the sensor signals indicate the rotor is in an angular position between 0 and 60°. If this determination tests false, collectively the signals indicate the rotor is in a position between 120 and 180°. If the normalized output signal from sensor 74 indicates the rotor is in either the 180 to 240° sextant or the 300 to 360° a test is made to determine if:

sensor 74 signal<sensor 76 signal

If this determination tests true, then, the sensor signals indicate the rotor is in an angular position between 180 and 240°. If this determination tests false, then the rotor is in a position between 300 and 360°.

Thus, on start-up, based on the signal from sensor 74 and the comparison of the signals generated by sensors 74 and 76, the DSP 170 generates a HALLx signals representative of motor rotor position.

Consequently, immediately after start-up, DSP 170 presents the following signals to MCC 172: the FORWARD and/or REVERSE signals; a USER_SPEED signal; and HALLx signals. Based on these signals, MCC 172 asserts the HIGH_ and LOW_SIDE_CONTROL signals. These signals are asserted in the sequence necessary to cause the energization currents to be applied to the windings in the appropriate pattern needed to cause the rotor 78 to be rotated in the appropriate user-selected direction and at the appropriate user-selected speed.

Based on the above signals, in step 393, MCC appropriately gates FETs 82a-82c and 84a-84c to cause the energization signals to be applied to the windings 86a-86c so that rotor 78 turns in the appropriate direction.

As energization signals are applied to the windings, the rotor 78 rotates. Once the initial position of the rotor 78 is determined, the later positions of the rotor 78 are determined solely on the basis of the signal produced by sensor 74. DSP 170 converts this signal into subsequent sets of HALLx signals. Based on the state of the HALLx signals, MCC 172 continues to assert the HIGH_ and LOW_SIDE_CONTROL signals needed to cause the rotor to turn in the user-desired direction at the user-desired speed.

Figure 10:
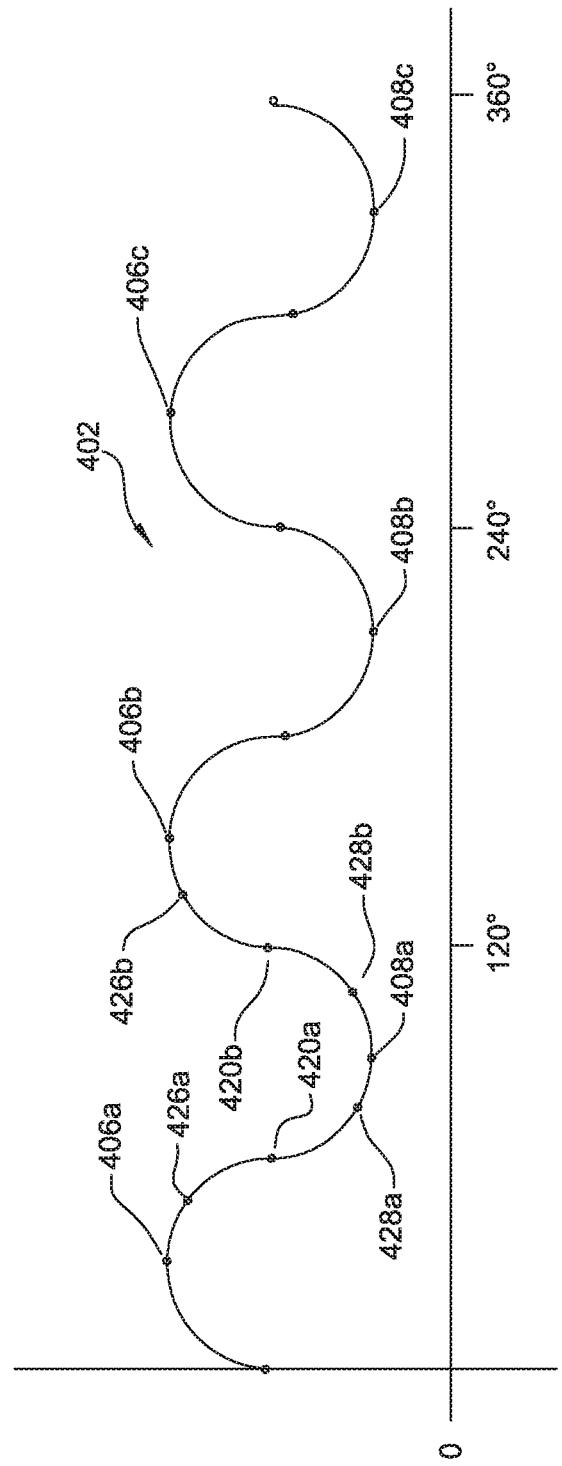
FIG. 10 is a plot of the waveform of the output signal generated by the primary sensor that monitors motor rotor position.
Figure 11A:
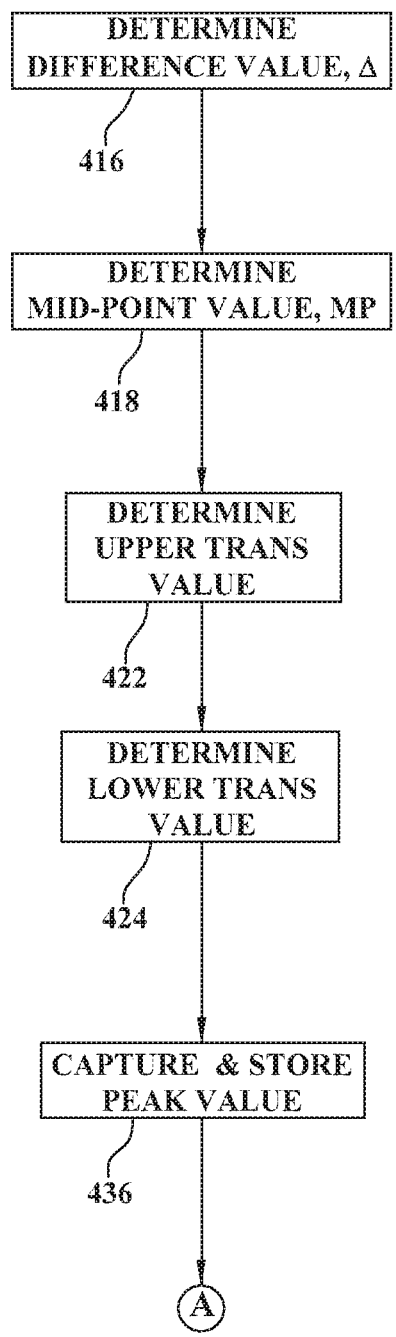
FIGS. 11A-11D collectively form a flow chart of the process steps executed by a processor integral with the tool control module in order to generate digital signals representative of motor rotor position as the rotor turns.
Figure 11B:
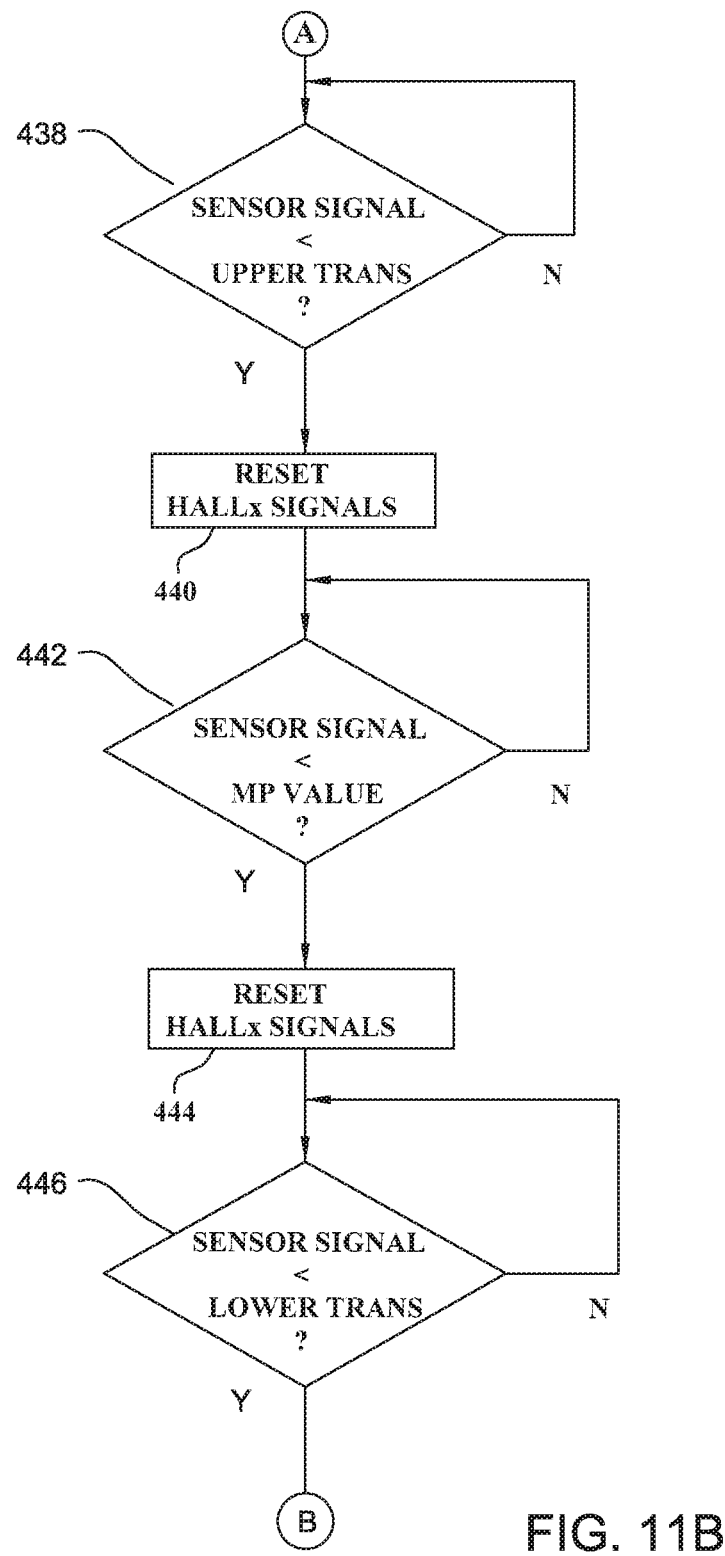
Figure 11C:
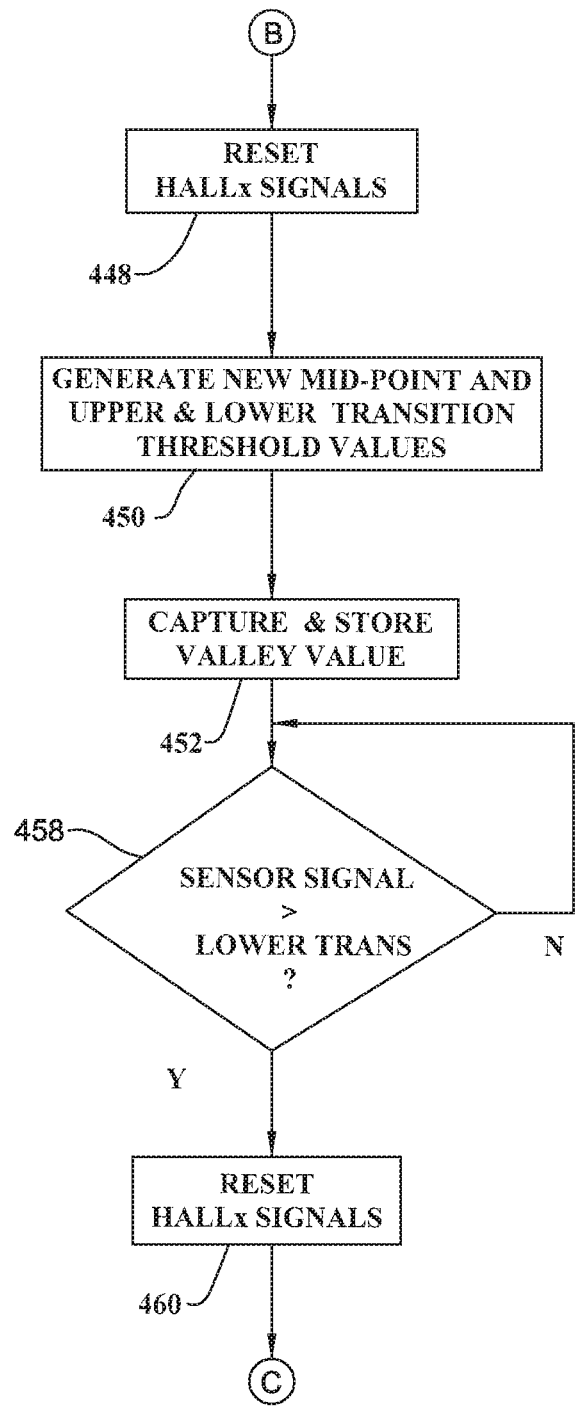
Figure 11D:
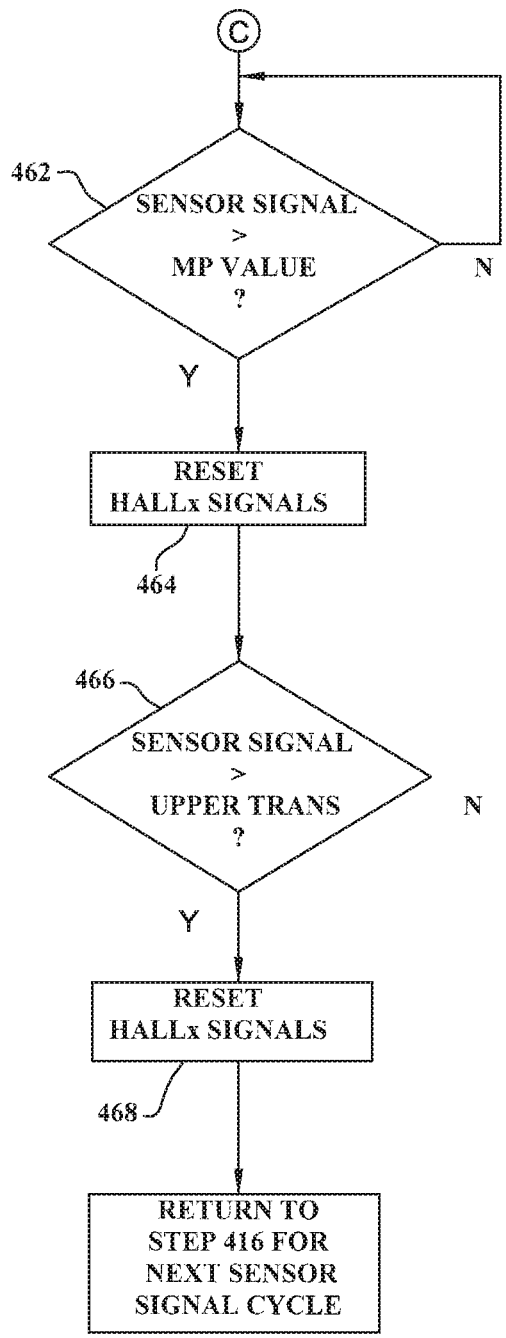

The means by which the HALLx signals are subsequently determined is described by reference to waveform 402 of FIG. 10 and the flow chart of FIGS. 11A-11D. Waveform 402 represents the output signal from sensor 74 over a complete 360° of rotation of rotor 78. Since rotor 78 is a six pole rotor, over the course of the complete rotation, sensor 74 generates three sine waves. In FIG. 10, the three peak values are the values at points 406a, 406b and 406c. The three valley values are the signal levels at points 408a, 408b and 408c. In FIG. 10, the individual sine waves are shown as having identical peak and valley signal levels. It should be understood that, in actuality, even at a very cold or very hot start-up, there are some differences in these signal levels. These differences though are typically less than 5%.

Figure 12:
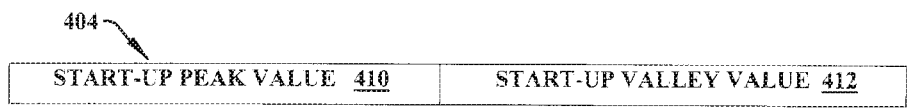
FIG. 12 depicts some of the data stored in a permanent memory integral with the control module processor.

During manufacturing calibration, a non-volatile memory 404 integral with DSP 170, represented by FIG. 12, is loaded with data representing the peak and valley point values of the output signal from sensor 74. A single start-up peak value is stored in field 410. A single start-up valley value is stored in a field 412. In some versions of the invention, the single start-up peak value is the largest of the three peak values at points 406a, 406b or 406c. The single start-up valley value is the value lowest of the three valley values 408a, 408b or 408d. In an alternative version of the invention, the stored start up peak value is the average or median of the three peak values 406a, 406b or 406c. In these versions of the invention, the stored valley value in field 412 is the average or median of the three valley values 408a, 408b or 408c.

Prior to sensor 74 generating the output signal representing the transition from one peak to the next valley (or one valley to the next peak) DSP 170 performs signal processing to determine when the state of the HALLx signals are to be changed. Specifically in a step 416, for the signals from peak 406a to valley 408a, DSP 170 determines the difference value, Δ, between the peak and the valley. This value is determined by the formula:

$$\Delta = \text{SIGNAL VALUE}^{PEAK} - \text{SIGNAL VALUE}^{VALLEY} \qquad (2)$$

In a step 418, a midpoint value, MP, between the peak 406a and valley 408a is determined according to the following formula:

$$MP = \Delta/2 + \text{OFFSET} \qquad (3)$$

Here, OFFSET is the level of the sensor signal at the valley 406a, the SIGNAL VALUE$^{VALLEY}$ signal. In FIG. 10, this midpoint reference signal level is represented by point 420a. At least, immediately after startup, it should be understood that the SIGNAL VALUE$^{PEAK}$ and SIGNAL VALUE$^{VALLEY}$ values are the signal levels retrieved from memory 404.

In steps 422 and 424 the DSP 170 determines, respectively, the upper and lower transitions for the signal from sensor 74. In step 422, the upper transition is determined according to the formula:

$$\text{UPPER TRANS} = MP + 0.433\Delta \qquad (4)$$

In step 424, the lower transition is determined according to the formula:

$$\text{LOWER TRANS} = MP - 0.433\Delta \qquad (5)$$

In Equations (4) and (5), the constant 0.433 is based on the fact that, in this version of the invention, the HALLx signal transitions are to occur at each 60° phase change of waveform 402. The first phase change/HALLx signal transition occurs as the waveform changes from the 359° to 0° position. Therefore, the next HALLx signal transition-inducing phase occurs when the sensor 74 signal transitions above 60° position; the sin of 60° is 0.866. Similarly, there is a HALLx signal transition-inducing phase change when the sensor 74 transitions from the 179° position to the 180° position. Therefore, the next HALLx signal transition-inducing phase change occurs when the sensor 74 signal drops below 240°. The sin of 240° is –0.866.

Since the signals produced by sensor 74 are all output above 0.0 Volts, MP>0.0. Therefore, the midpoint values are representative of the sensor 74 signal levels when the signal transitions from 359° to 0° and from 179° to 180°. The transition signal values of Equations (3) and (4) are offset from the midpoint value.

Graphically in FIG. 10, point 426a on waveform 402 represents the upper transition reference signal level as the signal from sensor 74 drops from peak value 406a to valley value 408a. Point 428a represents the lower transition reference signal level as the signal undergoes this transition.

The above transition reference signal levels are thus used to determine the levels of output signal from sensor 74 as it transits from the level above peak value 406a to the valley value 408a. These signal levels represent the angular position of rotor 78 as it rotates. The determination of these signal levels is used by DSP 170, in turn, to determine when the state of the HALLx signals should be changed.

In the remaining steps of FIGS. 11A-11D, it is assumed that, in step 378 it was determined that the start-up, 0 RPM, position of motor rotor 78 is within 30° of the peak position represented by any one of the peak values 406a, 406b or 406c. At start up, the peak and valley values stored in memory 404 are identical. Therefore, the data from which the mid-point and upper and lower transition signals are determined are, for each of the three cycles of sensor 74 signal for a single 360° rotation of rotor 78. Therefore, in order for the remaining steps used to determine rotor position immediately after start up, there is no requirement the DSP 170 be supplied with data indicating through which of the three 360° output signal cycles sensor 74 is presently cycling. Therefore, for purposes of example, it is arbitrarily assumed that output signal from sensor 74 indicates it is near the position of peak level 406a.

Figure 13:
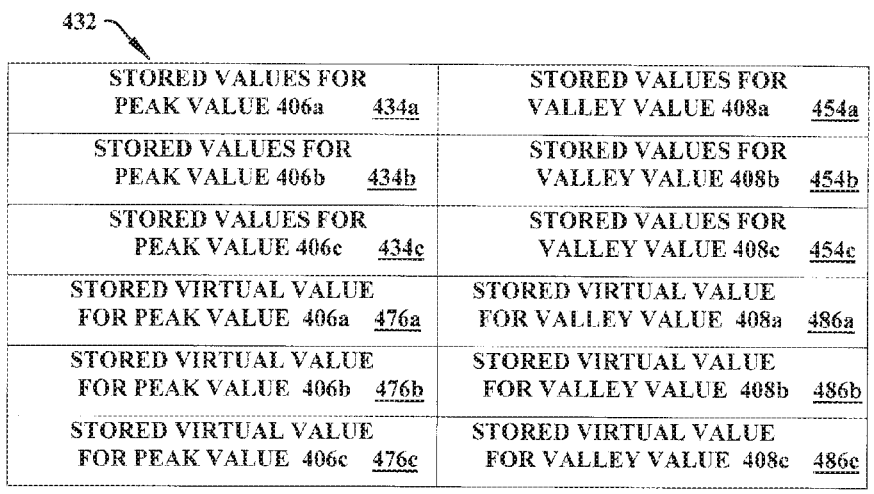
FIG. 13 depicts some of the data stored in a random access memory integral with the control module processor.

During the cycling of the output signal from sensor 74, the DSP 170 monitors the output signal to capture the actual peak value signal level from the sensor of peak 406a. This value is stored in a RAM memory 432, FIG. 13, associated with the DSP 170. In practice, the captured peak value is stored in table 434*a* of peak values for point 406*a*. Collectively, these two processes are represented by step 436. The purpose of the storage of this signal level is discussed below. It should further be appreciated that, at start-up, it may not be possible to execute step 436.

Then, in a step 438, DSP 170 continues to test to determine if the sensor 74 output signal falls below the upper transition reference signal level, the level of point 426*a*. Once the output signal falls below this level, in step 440, the DSP resets the HALLx signals to reflect the new position of rotor 78. Then, in step 442, the DSP 170 continually tests the sensor 74 output signal to determine if it falls below the midpoint reference signal level, the level of point 420*a*. Once this event occurs, in step 444, the HALLx signals are again reset.

In step 446, DSP 170 tests the sensor 74 output signal to determine if the signal level falls below the lower transition reference signal level, the level of point 428*a*. Once this event occurs, in step 448, the DSP 170 again resets the HALLx signals.

After step 448, DSP 170 re-executes steps 416, 418, 422 and 424. In FIG. 10, the re-execution of steps 416, 418, 422 and 424 is shown as step 450. In this execution of steps 416, 418, 422 and 424, DSP 170 determines the mid-point and the upper and lower transition reference signal levels in order to determine when, as the signal output from sensor 74 transits from valley value 408*a* to peak value 406*b*, the state of the HALLx signals are reset. On FIG. 10, the new lower transition reference signal level is represented by point 428*b*, the new mid-point reference signal level is represented by point 420*b* and the new upper transition reference signal level by point 426*c*. Again, it should be understood that at least initially, these signal midpoint and upper and lower transition levels are calculated based on the peak value signal level data stored in memory 404.

Also, in a step 452, the DSP 170, monitors the sensor 74 output signal to determine the actual signal level of valley 408*a*. This value is stored in a table 454*a* of RAM 432.

Then, as the output signal from sensor 74 rises from valley 408*a* to peak 406*b*, the signal is tested against the new mid-point and transition reference signal levels. Specifically, a step 458 is executed to determine when the sensor 74 output signal rises above the lower transition reference signal level, point 428*b*. Once this event occurs, in step 460, the HALLx signals are appropriately reset. Then, a step 462 is executed to test when the sensor 74 output signal rises above the mid-point reference signal level, point 420*b*. After this event occurs, DSP 170 resets the HALLx signals as appropriate, step 464.

In a step 466, DSP 170 then tests to determine when the sensor 74 output signal rises above the upper transition reference signal level, above the level of point 426*b*. Once this event occurs, DSP 170 again resets the HALLx signals, step 468.

The above processes are re-executed as rotor 78 completes a full 360° of rotation. Thus, steps 416, 418, 422, 424 and 438-448 each time the sensor 74 output signal transits from a peak value 406*x* to a valley value 408*x*. Each time the sensor 74 output signal transits from a valley value 408*x* to the next peak value 406*x*, steps 450 and 458-468 are executed.

From the above, it should be appreciated that each time the output signal from sensor 74 transits through a single sine wave cycle, from one peak through the adjacent valley to the next peak, the HALLx signals undergo six state transitions. When the sensor 74 output signal transits through the next sine wave cycle, the HALLx signals undergoes the same six transitions. In order to properly gate FETs 82*a*-82*c* and 84*a*-84*c*, the MCC 172 only requires the data indicating in which sextant of a sine wave cycle the rotor 78 is positioned. The MCC 172 does not need to know in which of three sine waves generated during a 360° rotation of the rotor 78 the rotor is transiting. This is why only three individual HALLx conductors are required to provide a 3-bit binary HALL signal representative of rotor position to the MCC 172.

The above is also why, at start-up, it is only necessary to provide the DSP 170 with sufficient sensor data to indicate in which sextant of a sine wave cycle the rotor 78 is positioned. Based on these data alone, DSP 170 is able to immediately calculate the reference levels against which the later received and changing output signal from sensor 74 is compared.

Also during the rotation of rotor 78, the DSP continually executes step 436 to capture and store the values of each sine wave peak 406*a*, 406*b* and 406*c*. These values are stored in tables 432*a*, 432*b* and 432*c*, respectively, of RAM 432. Step 452 is also continually executed as long as the handpiece 30 remains actuated in order to capture and store the values of each sine wave valley 408*a*, 408*b* and 408*c*. These values are stored in tables 454*a*, 454*b* and 454*c*, respectively, of RAM 432.

Figure 14:
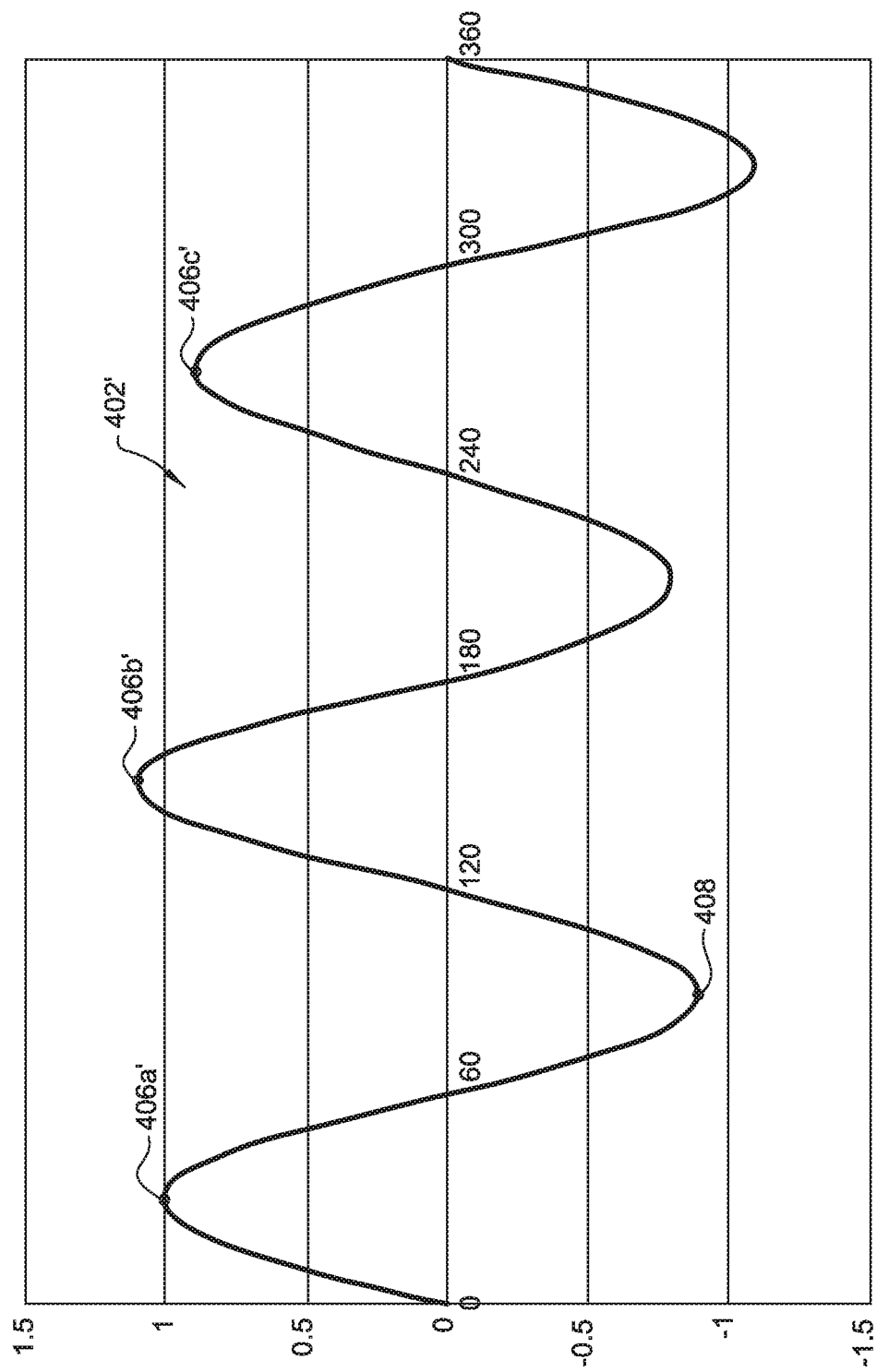
FIG. 14 is a plot of an alternative waveform of the output signal generated by the primary sensor that monitors motor rotor position.

The reason the sensor 74 output signal values representative of the sine wave peaks and valleys are stored is now described by reference to FIGS. 14 and 15. FIG. 14 is a plot 402' of the output signal of sensor 74 over a complete 360° rotation of rotor 78 after the handpiece has been actuated for a period of time. Here it can be seen that there are differences in the peak and valley signal levels between the individual sine waves. One reason these differences may arise is that, due to heating of the motor and the inherent physical differences in the rotor magnets, the magnetic fields emitted by the individual rotors start to vary.

Alternatively, post manufacture, the position of the sensor 74 may shift. Such shift may be due to exposure to mechanical shock if the handpiece 30 is dropped. If sensor 74 so shifts position, it may be positioned so that the amplitudes of the sensed magnetic fields vary. This is a second reason that, post-manufacture, the output signal from sensor 74 shifts from the relative uniform appearance of FIG. 11 to the uneven appearance of FIG. 14. In FIG. 14 points 406*a'*, 406*b'* and 406*c'* represent the new peak values' points 408*a'*, 408*b'* and 408*c'* represent the new valley values.

Exposure of the sensor 74 to heat as a result of tool autoclaving can also cause the output signal of the sensor 74 to vary.

Figure 15:
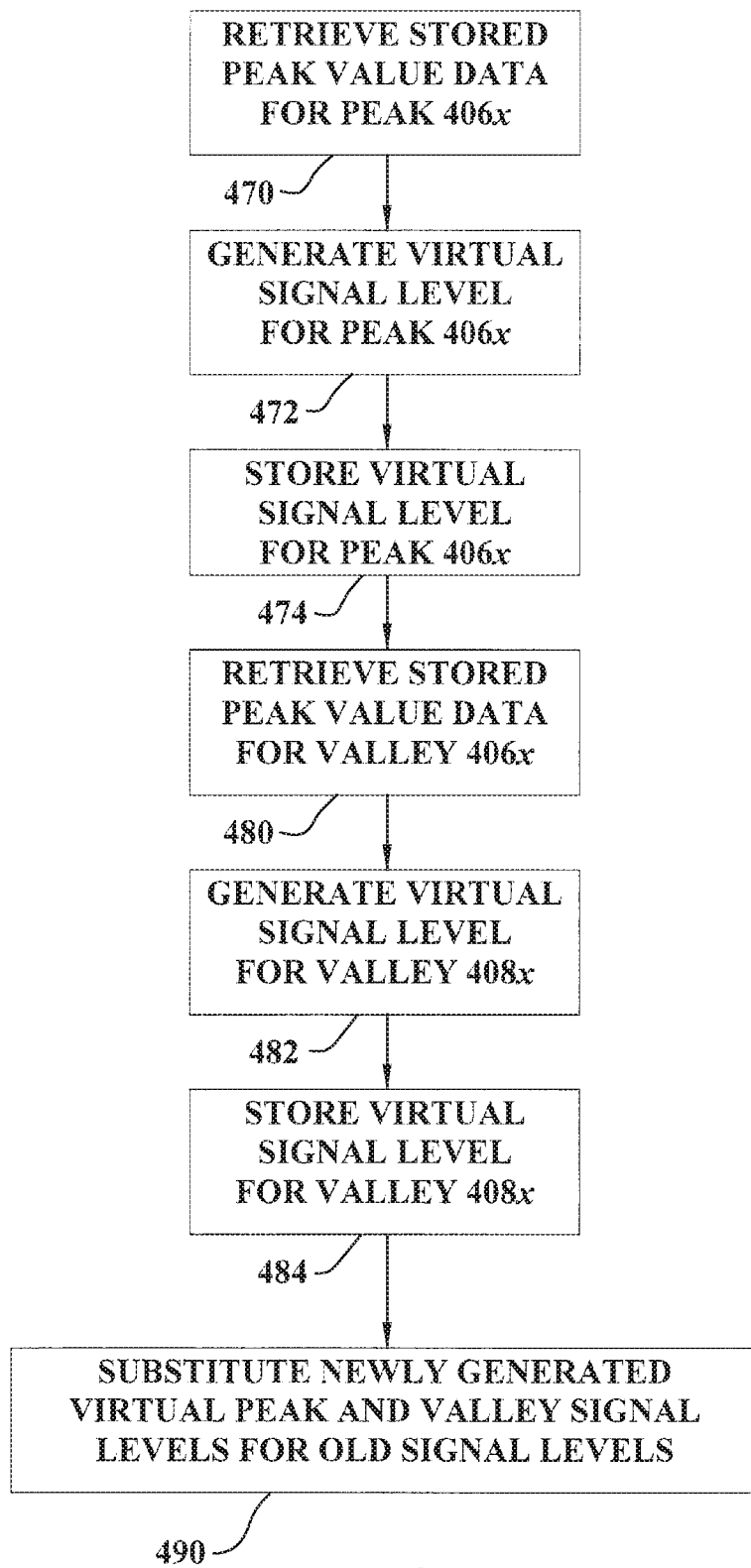
FIG. 15 is a flow chart of the process steps executed to update the signal transition levels against which the motor sensor output signal is compared.

To compensate for the shifting in sensor 74 output signals, DSP 170 performs the further processing of FIG. 15. Specifically, in a step 470, the DSP 170 retrieves the stored peak value data in one of the tables 434*a*, 434*b* or 434*c* of memory 432. The data, in step 472 are then processed to generate a new estimated to produce a virtual signal level for the associated sine wave peak. In one version of the invention, each table 434*x* contains the last captured peak signal value. This value is then employed as the peak signal in the next set of calculations to determine the HALLx signal transition reference signal levels.

In other versions of the invention, each table field 434*x* and plural captured peak signal values. In step 472 simple averaging or weighted averaging of these values are used to generate the virtual signal level for the peak 406*x*. These virtual values for peaks 406*a*, 406*b* and 406*c* are stored in fields 476*a*, 476*b*, and 476*c*, respectively. These process steps 470-474 are performed for each of the three sine waves, (loop back not shown).

Similarly, in a step 480, DSP 170 retrieves the stored valley value data in one of the tables 454a, 454b or 454c of memory 432. The data, in step 482 are then processed to generate a new estimated to produce a virtual signal level for the associated sine wave peak. Typically the same algorithm used to generate the virtual signal levels for each peak is used to generate the virtual signal level for each valley 408a, 408b or 408c. In step 484 the calculated virtual sine wave valley level is stored in a field 486a, 486b or 486c of memory 432. Process steps 480-484 are performed for each of the three sine waves, (loop back not shown).

Once steps 470-474 and 480-484 are performed, step 490 is executed. In step 490, DSP 170 substitutes these calculated virtual peak and valley signal levels for the previous levels used to determine the mid-point and upper and lower transition signal levels. Thus, in the future executions of steps 416, 418, 422, 424 and 450, these virtual signal levels are used as the input variables for Equations 2 and 3 above. Thus, once step 490 is executed, the later generated mid-point and upper and lower transition reference signal levels are based on peak and valley signal levels that closely approximate the actual peak and valley signal levels generated by sensor 74. This ensures that, should the output signal from sensor 74 vary from manufacture or vary during a single procedure, DSP 170 continues to assert HALLx signals that are accurately representative of rotor position.

Returning to FIG. 8C, it should be understood that, as long as the trigger switch 46 and/or 47 remains depressed, DSP 170 asserts the ACTUATE signal, the FORWARD and/or REVERSE signal, the USER_SPEED signal and the HALLx signals, step 494. The MCC 172, in turn, in step 496, continues to gate FETs 82a-82c and 84a-84c as appropriate to cause the rotor to turn in the appropriate direction at the user-selected speed.

Steps 494 and 496 are continually executed as long as the trigger switch 46 and/or 47 remains depressed. As represented by step 497, eventually the surgeon releases pressure on the trigger switch 46 and/or 47 to deactivate the handpiece. Initially, when this event occurs, the magnet 56 and/or 58 moves to a position beyond which the sensor 68 or 72 cannot detect the presence of an appreciable magnet field. Sensor 68 or 70 thus produces an output signal that causes the DSP 170 to assert a zero speed USER_SPEED signal, step 498.

At the time the MCC speed controller 276 receives this zero speed USER_SPEED signal, the motor rotor 78 is turning. Therefore, the speed controller 276 causes the MCC to negate the assertion of signals to FETs 82a-82c and 84a-84c that cause currents to be applied to the windings 86a-86c that cause rotor rotation, step 502. Instead, the speed controller asserts the BRAKE_ENABLE signal. This causes MCC 172 to gate FETs 82a-82c and 84a-84c so that the windings enter a braking mode that slows the rotation of rotor 78, step 504.

As the magnet 56 or 58 moves further away from control module 40, the field generated is no longer sensed by sensor 66 or 70. Consequently, in step 506, the output signal from sensor 66 or 70 goes to the off state. The toggling of the signal from sensor 66 or 70 to the off state causes DSP 170 to stop asserting the AWAKE signal, step 508. This causes the deactivation of voltage regulator 176 and amplifiers. The deactivation of voltage regulator 176 results in the like deactivation of MCC 172. Collectively, the deactivation of these components, represented by step 510, is the entry of the handpiece back into the energy-saving sleep mode.

In one version of the invention, as soon as the output from sensor 66 or 70 returns to the off state signal, the DSP 170 immediately negates the AWAKE signal. In another version of the invention, there is a delay of up to 5 seconds, between when sensor 66 or 70 asserts the off-state signal and when the DSP negates the AWAKE signal. During this delay period, MCC 172 continues to assert the signals that foster braking of the motor rotor 172. An advantage of continuing this braking is that it reduces the mechanical shock to which the individual holding the handpiece 30 is otherwise exposed.

Handpiece 30 remains in the sleep state until, in a re-execution of step 364, a trigger switch 46 or 47 is again depressed.

II. Integrated System

As discussed above tool 30 is custom configurable for each use. In step 360, the trigger switch functions (forward, reverse, oscillate or off) are loaded into DSP 170. In step 362, DSP 170 is loaded with the range of the USER_SPEED signals it should generate as a function of the depression of a trigger switch 46 or 47. The mechanics by which these and other instructions are loaded into the tool 30 is now explained by initial reference to FIGS. 16 and 17. The tool 30, in addition to the control module 40 components internal to the module, also includes one or more data transceiver heads 530 (one shown). Each transceiver head 530 exchanges signals with a unit physically separate from the tool 30. As illustrated in the block diagram version of the tool of FIG. 16, that the transceiver head 530 will be external from the control module 40. In some versions of the invention, it may be possible to place a transceiver head 530 internal to the control module 40. In one version of the invention, the DSP 170 (tool control processor) exchanges signals with the transceiver head over a serial data communications line 531.

The actual means by which the transceiver head 530 exchanges signals with the separate unit is not, in this invention, limited to a particular technology. In some versions of the invention, in order to facilitate signal exchange the tool is seated in a docking station 532. Docking station 532 has its own transceiver head 534. When the tool 30a is seated in the docking station 532, the two transceiver heads 530 and 534 are positioned close enough together to allow the signal exchange therebetween.

In some of these versions of the invention, transceiver heads 530 and 534 are exposed electrical contacts that mate when the tool (tool 30a in FIG. 17) is docked. Alternatively, the transceiver heads 530 and 534 are complementary coils that allow inductive signal transfer. Transceiver heads 530 and 534 may be complementary pairs of light emitting and light detecting components. These versions of the invention emit and or detect light at a particular frequency including possibly light in the infra-red spectrum. Alternatively, transceiver heads 530 and 534 are complementary RF antennae. In these versions of the invention each transceiver head 530 and 534 also includes the appropriate signal modulating and demodulating sub-circuits to convert the exchanged signals between electrical and RF states. Transceiver heads 530 and 534 may even be complementary exposed sets of conductors. This arrangement requires physical connection of the surgical tool 30a to the docking station. An advantage of this arrangement is that it allows for very high baud rate between the tool 30a and the other components of the system.

Figure 17:
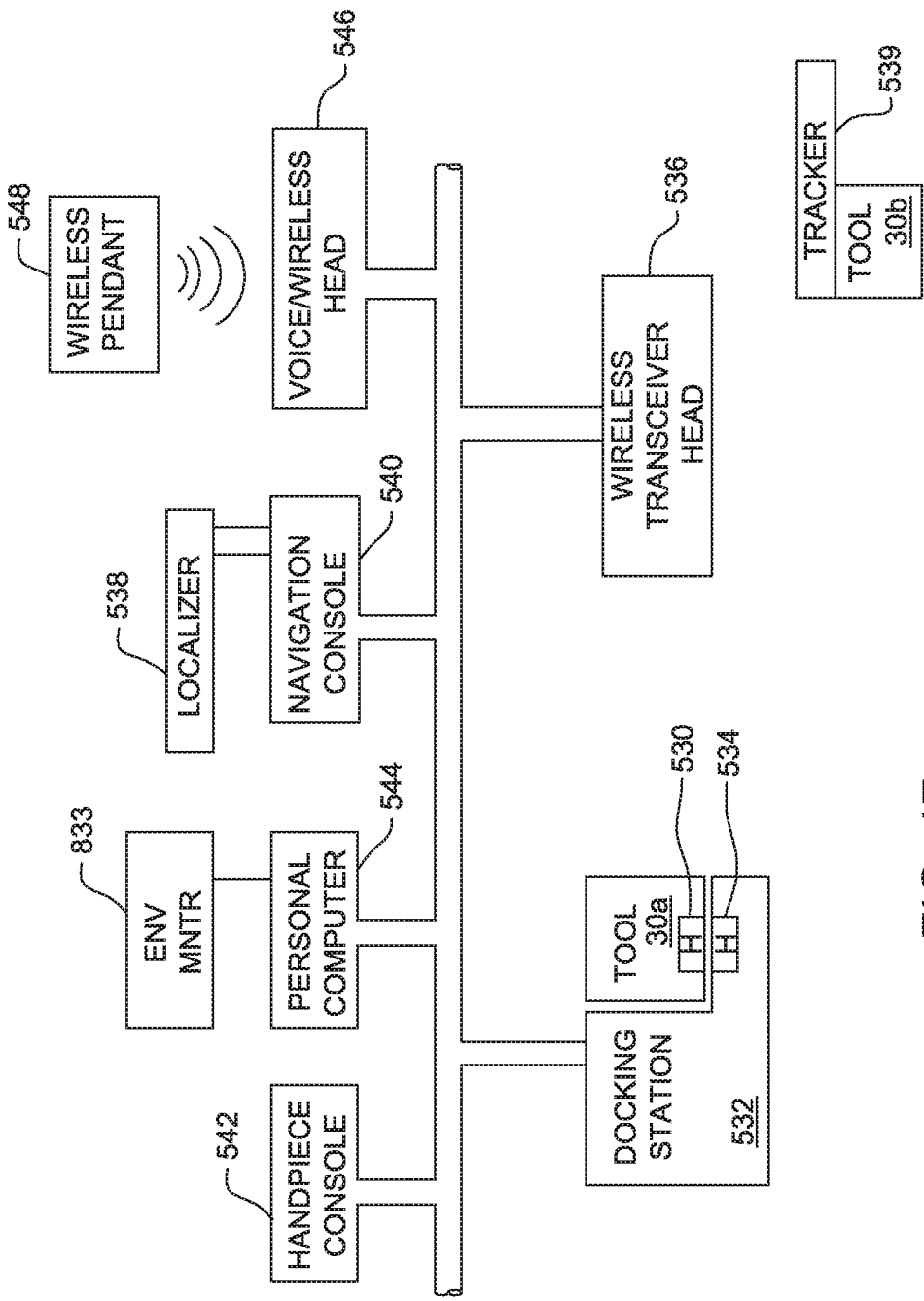
FIG. 17 is a system diagram illustrating the components external to the tool that used to externally configure and control the tool.

As seen by tool 30b and wireless transceiver head 536 of FIG. 17, there is no requirement a tool be in a static dock in order to for the data transceiver 530 to exchange signals with the separate unit. In these versions of the invention, tool transceiver head 530 and wireless transceiver head 536 exchange signals wirelessly even when tool 30b is a distance of a meter or more away from head 536 and is being moved. This signal exchange by the exchange of light including infra-red pulses, radio waves, including such technologies as WiFi, Bluetooth or G3, or electromagnetic pulses.

In some versions of this embodiment of the invention, tool transceiver head 530 and wireless transceiver head 536 are part of a surgical navigation system. Briefly, a surgical navigation system includes a fixed unit and a mobile unit attached to the device the position of which is being tracked. One of the units transmits a set of two or more signals, typically light, electromagnetic or RF. The second unit has two or more sensors that receive the transmitted signals. Based on the differences in signal strength of the received signals, a surgical navigation console (data processor) 540 generates data indicating the position and orientation of the mobile unit relative to the fixed unit. Many surgical navigation systems are designed so that the mobile unit emits the light. This mobile unit, referred to as a tracker 539, is attached to the mobile device, the surgical tool 30b of FIG. 16. The fixed unit, referred to as a localizer 538 contains the sensors that monitor the emitted light. Tracker 539 contains the sensors. By tracking the position and orientation of the tool 30b, the surgical navigation console 540 generates that indicates the position of the surgical tool 30b and/or the complementary attachment relative to the surgical site on the patient.

In some versions of the invention, tool transceiver head 530 is built into the tracker 539; wireless transceiver head 536 is built into the localizer 538.

Tool 30a or 30b exchanges signals with one or more units. One of these units is, for example, the surgical navigation console 540. A second type of unit with which tool 30a or 30b may exchange signals is a handpiece control console 542. Console 542 is normally employed to apply energization signals a corded surgical tool. Two such consoles 542 are disclosed in the Applicant's Assignee's U.S. Pat. No. 6,017,354, INTEGRATED SYSTEM FOR POWERED SURGICAL TOOLS, issued 25 Jan. 2001 and its U.S. patent application Ser. No. 10/955,381 filed 30 Sep. 2004, INTEGRATED SYSTEM FOR CONTROLLING PLURAL SURGICAL TOOLS, U.S. Patent Pub. No. 2006/0074405 A1, now U.S. Pat. No. 7,422,582, both of which are incorporated herein by reference.

A personal computer 544 may also serve as the unit with which tool 30a or 30b communicates. It should be appreciated that computer 544, or any other of the units may serve as a gateway through which data are exchanged between the tool 30a and 30b and unit that is not even located in the operating room/surgical suite in which the procedure is being performed. Such unit may, for example be a memory store device in which logs of data regarding the use of the tool 30a or 30b or the surgical procedure are maintained. Personal computer 544 or other operating room unit may be connected to this remote unit through a convention network such as Ethernet or POTS.

A voice/wireless head 546 may also serve as the unit with which tool 30a or 30b exchanges signals. One such head 546 is sold by the Applicant's Assignee under the trademark SIDNE. Surgical personnel using a headset-mounted microphone (not illustrated) speak commands. Voice/wireless head 546 contains speech recognition circuits that convert the audible commands into digital signal packets. Head 546 also serves as the head through which signals from a wired or wireless device, wireless pendant 548 illustrated, are received. Thus, a surgeon enters a command by pressing touch screen buttons presented on pendant 548. These commands are broadcast to head 546. Head 546, in turn, converts these commands into digital signal packets.

It should likewise be understood that the other remote units used to communicate with the tool such as the surgical navigation console 540, handpiece control console 542 or personal computer 544 may have touch screen displays in which buttons are presented that allow commands to be entered to the tool. Alternatively, units like the surgical navigation console 540 or personal computer 544 have keyboards and/or mice through which commands are entered.

In FIG. 17, docking station 530, wireless transceiver head 536, navigation console 540, handpiece control console 542, personal computer 544 and voice wireless head 546 are tied to a common bus 552. The bus may be any bus such as an IEEE-1394 Firewire bus or LAN. Thus, in this construction of the invention, each external unit navigation console 540, handpiece control console 542, personal computer 544 and voice wireless head 546 can exchange signals with either one of the tools 30a or 30b. Also, as discussed below, this configuration of the system further allows tool 30a to communicate with tool 30b.

Alternatively, in a less complex system, a single external unit is simply the only component connected to a docking station 530 or wireless transceiver head 536.

Figure 18:
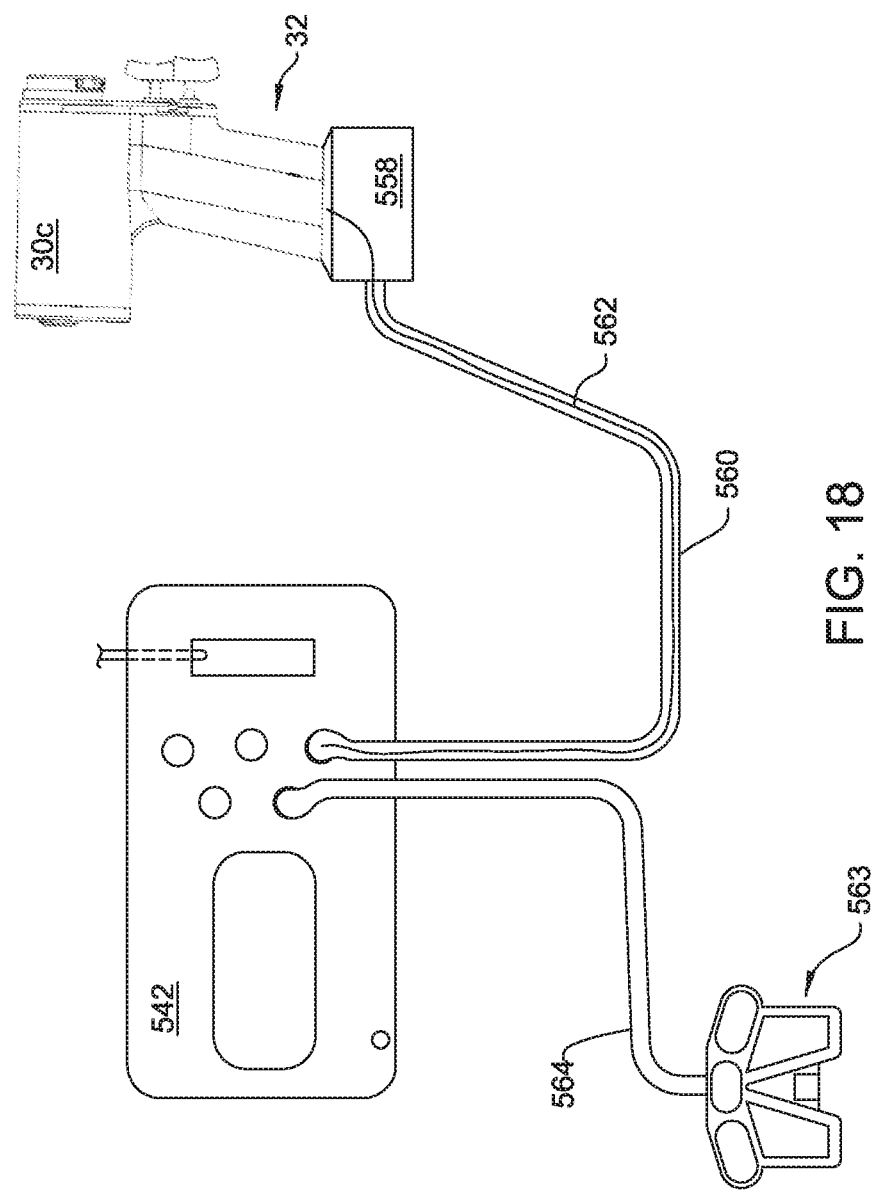
FIG. 18 is a diagrammatic view of a how a tool of this invention exchanges data and instructions with a handpiece control console through a corded power pack.

Still another means by which signal may be exchanged with a tool 30c of this invention is illustrated with respect to FIG. 18. As discussed above, some surgeons, in some circumstances, do not object to working with corded tools. One advantage these tools offer is that, since the power is always available from the hospital supply network the possibility that due to battery discharge, the tool will slow or cease operation is eliminated. Thus, it is known to provide these surgeons with a corded power pack 558. Power pack 558 couples to the tool housing 32 at the location at which the cordless battery pack is normally fitted. A cord 560 extends from the pack 558. The proximal end of cord 560 plugs into a socket (not identified) part of handpiece control console 542 into which the power cord for a corded tool is otherwise attached. Console 542 supplies an energization signal to the pack 558 through cord 560, Internal to pack 558 are components not illustrated and not relevant to this invention that convert the energization signal supplied by handpiece control console 542 into a form that emulates the form otherwise supplied by battery 42.

Also internal to pack 558 and cord 560 are data conductors represented by a single line 562. The data conductors are conductive paths between the data transceiver head 530 in the tool 30c and the processor in the handpiece control console 542. Thus, in this configuration of the invention, tool 30c and handpiece control console 542 exchange signals without use of a docking station or wireless transceiver head.

In FIG. 18 a footswitch unit 563 is shown connected to the handpiece control console 542 by a cable 543. Commands may be entered into the system of this invention by selective depression of the footswitch pedal (pedals not identified). In some versions of the system of this invention footswitch unit 563 is wirelessly connected to the other system components.

Once a communications link is established between a surgical tool 30 and a remote unit, the control processor internal to the tool (DSP 170 of FIG. 16) transmits a number of different types of data to the remote unit. If the data transceiver head 530 is part of a surgical navigation system, built into tracker 539, these data include information that allows the surgical navigation system to determine the position and orientation of the tool. It should be recognized that these data are transmitted when other flexible communications links are established. These communication links are other wireless links or links established by flexible cables such as cable 543.

DSP 170 also provides the remote unit with data indicating the operating speed of tool motor 34. In some versions of the invention, the PWM measure of motor speed generated by MCC 172 is supplied to the DSP 170. The DSP 170, based on this signal produces a multi-bit digital signal representative of motor speed based on this measure of motor speed. In alternative versions of the invention, DSP 170, based on either the periodicity of either the output signal from sensor 74 or the HALLx signals, calculates its own measure of motor speed. This is the motor speed signal supplied through the data transceiver head 530 to the remote unit.

In other surgical tools of this invention wherein a device other than a motor is the power generating unit, the control processor still transmits a measure of power emitted by the generating unit to the remote unit. For example, if the tool is an RF ablation probe, the distal end of the surgical attachment has a temperature sensitive transducer, often a thermocouple. The control processor generates a digital representation of the temperature measured by the thermocouple and supplies these data to the remote unit.

In versions of the invention wherein the surgical attachment 41 is removable and replaceable, tool 30 also provides data regarding the identity of the tool. In these versions of the invention, the surgical attachment has an identification component 568 in which data regarding the characteristics of the attachment are stored. Component 568 is typically read through an electrical or optical process. Often component 568 is the form of an RFID or a NOVRAM. Tool 30 has a reader 570 capable of reading the stored in identification component 568. For example, the Applicant's U.S. patent application Ser. No. 10/214,937, SURGICAL TOOL SYSTEMS WITH COMPONENTS THAT PERFORM INDUCTIVE DATA TRANSFER, filed 8 Aug. 2002, U.S. Pat. Pub. No. 2003/0093103, and incorporated herein by reference discloses how data are read from an RFID chip in a surgical attachment, sometimes called a cutting accessory, by both corded and cordless surgical tools.

Once these data are read, the control processor forwards the data to the remote unit by the data transfer head 530.

The above-identified, incorporated-by-reference application Ser. No. 10/214,937 also discloses how data from intermediate devices between the tool housing and the actual applied-to-the-surgical site attachment are read. This document also discloses how data describing implants fitted into place by the tool are read back to the tool. Thus, it should likewise be understood that these data are likewise transmitted out through the data transceiver head 530 to the remote unit.

The tool control processor (DSP 170) also provides the remote unit with data describing the operating state of the tool components. For example, as discussed above these data, for example, include data indicating the charge level of the battery. Returning to FIG. 6B, it is appreciated that a signal representative of the voltage out of the battery is supplied to the DSP 170 from the junction of resistors 258 and 260. DSP 170, based on the level of this signal, outputs through transceiver head 530 data indicating the charge level across the battery.

Figure 16:
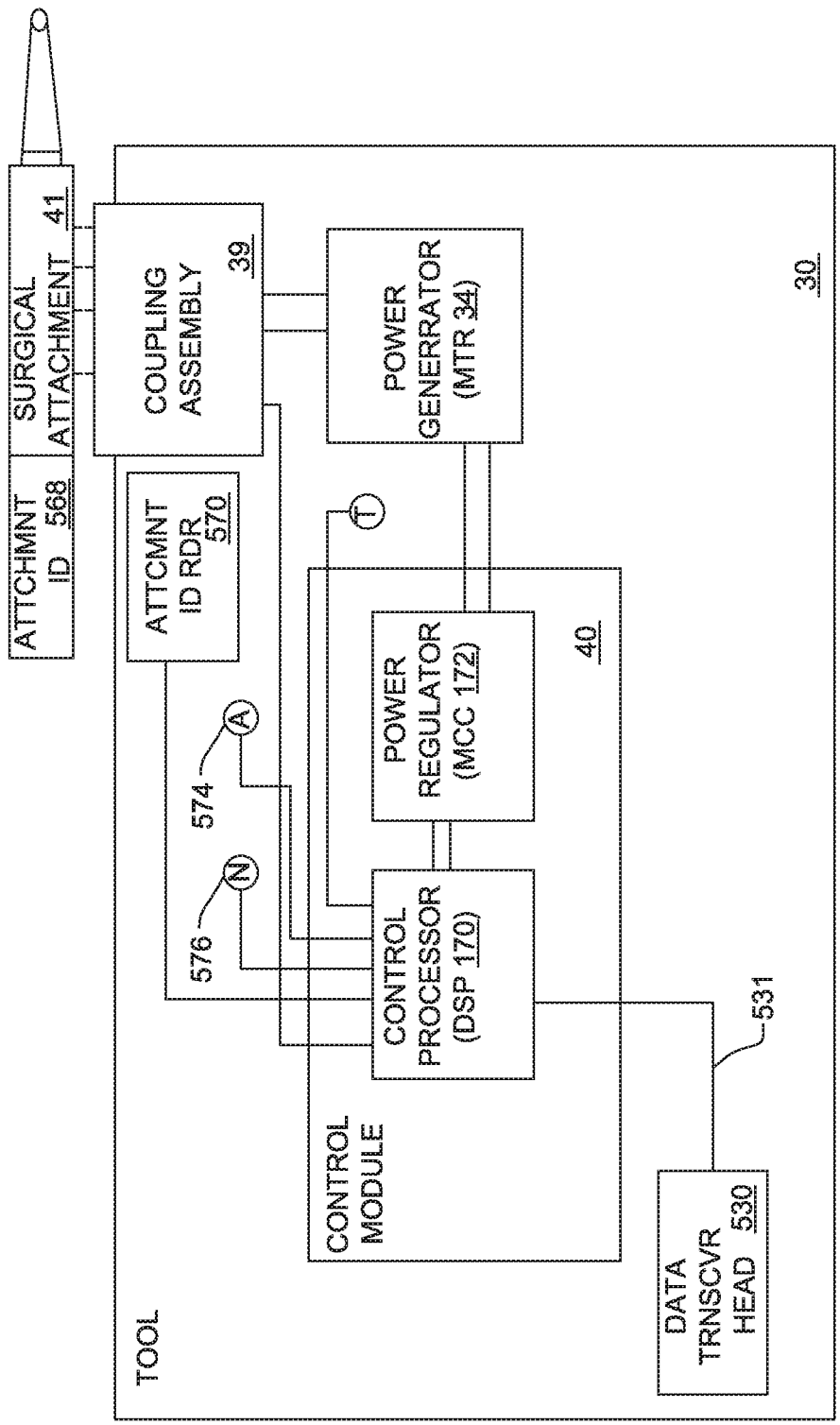
FIG. 16 is a block diagram of the components internal to the tool of this invention that facilitate the variable configuration and remote control of the tool.

A second tool operating parameter output is tool temperature. In FIG. 16, tool 30 is shown as having a temperature transducer 572. Transducer 572 is often placed near the heat generating component of the tool, typically the power generating component (motor 34). Alternatively, transducer 572 is positioned adjacent a surface of the tool normally grasped by the surgeon, for example, handle 38. The output signal produced by transducer 572 is supplied to the control processor (DSP 170). The control processor generates a digitized representation of this temperature and outputs these data by transceiver head 530 to the remote unit.

Tool 30 has an accelerometer 574 and a noise detector 576. Accelerometer 574 generates an output signal as a function of the vibration of the tool. Noise detector 576 generates a variable signal as a function of the noise emitted by the tool 30 and associated surgical attachment 41. The output signals from accelerometer 574 and noise detector 576 are supplied to the control processor (DSP 170). Digital representations of both these tool vibration and emitted noise are transmitted through data transceiver head 530 to the remote unit.

As mentioned above, when the power regulator (MCC 172) determines the power generating unit (motor 34) has attempted to draw excess current, a pulse bit indicating this event occurred is forwarded to the control processor (DSP 170). The control processor, in turn, forwards this information through the transceiver head 530 to the remote unit.

Some of the batteries 42 used to energize cordless versions of tool 30 have internal temperature sensors (not shown). The signal from this transducer is also supplied to the control processor (DSP 170). The control processor similar forwards a digital signal representative of the sensed battery temperature through transceiver head 530 to the remote unit.

Tool coupling assembly 39 may also have a sensor (not illustrated) that monitors the state of the assembly. Typically, this type of sensor asserts a first signal indicating when the coupling assembly 39 is in the locked state; the assembly is holding a surgical attachment 41 in place. The sensor asserts a second signal when the coupling assembly 39 is in the load state; an attachment 41 can be removed from and replaced back to the coupling assembly. The output signals asserted by this sensor are forwarded to the control processor (DSP 170). Whenever the signal from this sensor toggles, the DSP 170 transmits a data packet through the data transceiver head 530 to the remote unit.

III. Custom Tool Configuration

Figure 19:
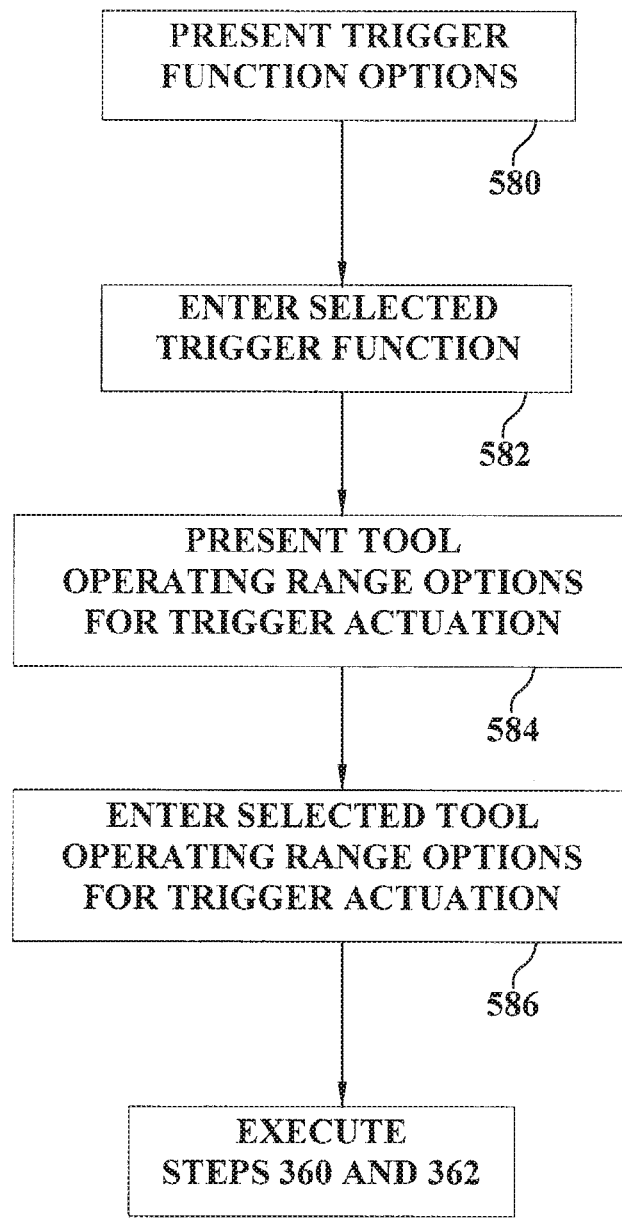
FIG. 19 is a flow chart of the steps performed by the integrated tool system of this invention in which the tool is configured to preferences of the surgeon.

The types of data the remote unit supplies to the tool 30 are first described by reference to FIG. 19. This Figure represents the process steps by which surgeon preferences for configuring the tool are loaded. Initially, the remote unit, for example handpiece console 542 or personal computer 544, is placed in an operating state in which the unit accepts the surgeon-selected custom configuration data, (step not shown). In a step 580, the remote unit generates a touch screen display in which the surgical personnel are invited to specify a function for a handpiece trigger 46: forward; reverse; oscillate; or off. In step 582, the personnel enter the selected function by depressing the appropriate touch screen button.

In a step 584, the remote unit presents one or more displays in which the surgical personnel are invited to specify the range at which the power generating unit should operate based on the range of movement of the trigger from the partially retracted to the fully retracted states. If the power generating unit consists of motor 34, in step 584, the remote unit presents displays inviting the surgical personnel to enter the selected minimum and maximum speeds at which the motor should operate based on the extent to which the trigger 46 or 47 is retracted. As discussed below, in step

584, the remote unit also invites the surgical personnel to indicate the rate of change of the power generating unit, for example, stepped speed increases or linear increases. In step 586, by depressing the appropriate buttons presented on the remote unit display, the surgical personnel enter the operating range profile wanted by the surgeon.

Steps 580-586 are then re-executed for the second trigger switch 47, (loop back not shown). Once the surgeon-selected operating configuration steps 360 and 362 are executed. Steps 360 and 362 are executed by the remote unit forwarding the surgeon-selected operating configuring data to the docking station transceiver head 534, the wireless transceiver head 536 or over cable 562 depending on which tool 30*a*, 30*b* or 30*c* is to be configured. These data are then loaded into the appropriate locations in RAM memory 432 of the control module 40 (memory locations not shown). Then, depending on which trigger 46 or 47 is actuated and the extent to which the trigger is actuated, the power generating unit (motor 34) is actuated in accordance with the surgeon's preferences.

Figure 20A:
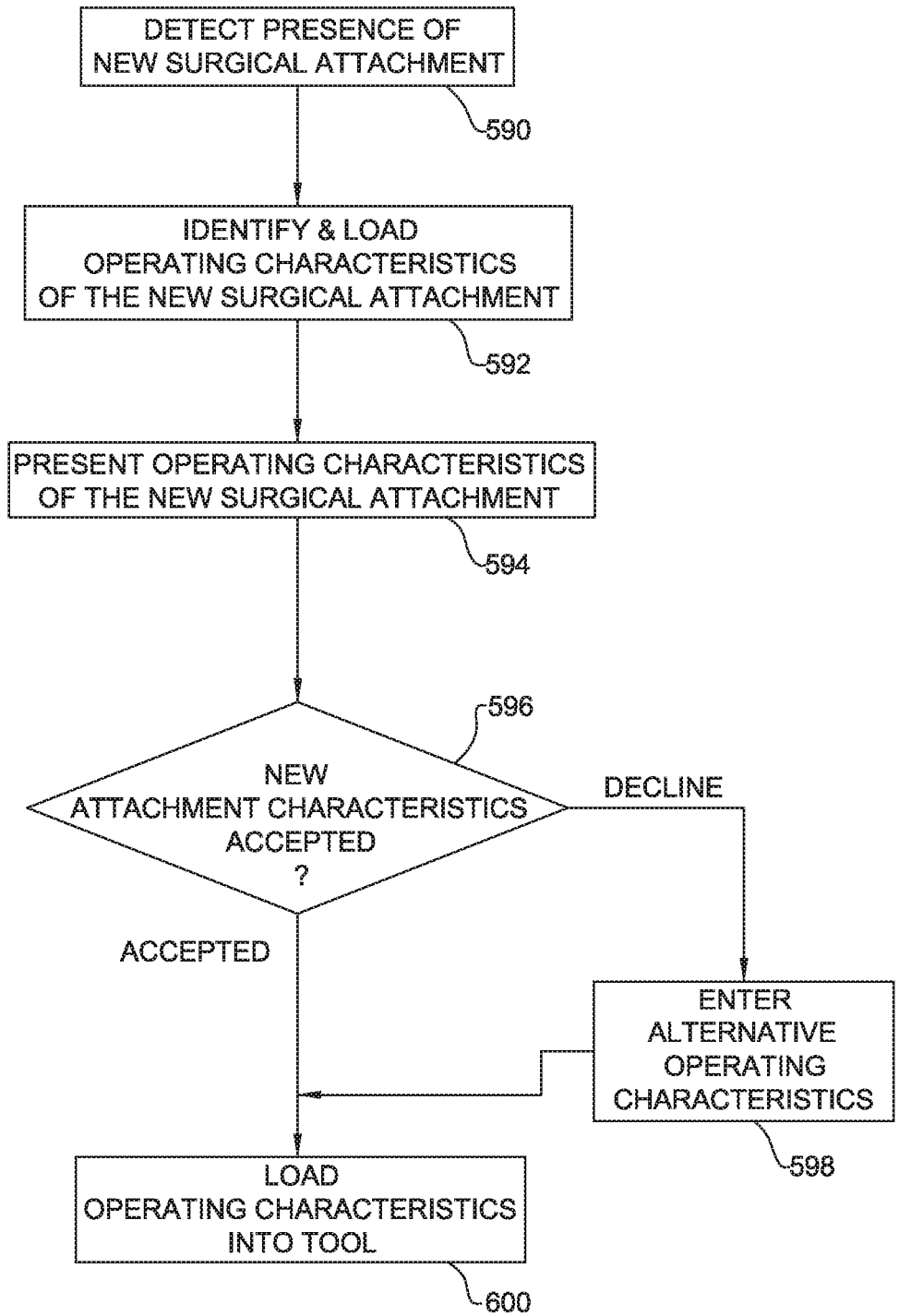
FIGS. 20A and 20B collectively form a flow chart of the steps performed by the tool system when the tool is configured based on the characteristics of the attached accessory and as operated based on these characteristics.
Figure 20B:
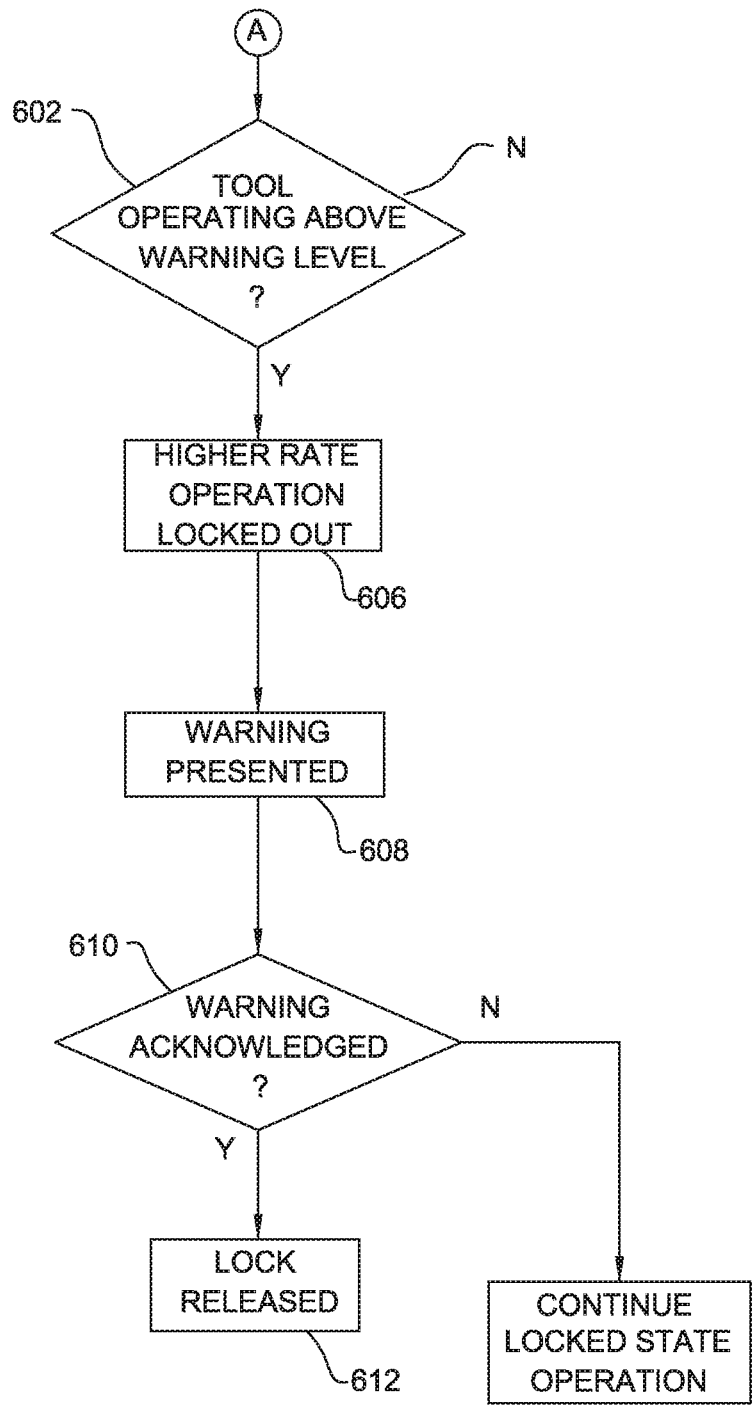

Tool configuration may be set as a function of the specific surgical attachment 41 coupled to the tool. In FIG. 20, the initial step 590 of this process is the detection by the system that a new surgical attachment has been coupled to the tool 30. There are a number of means by which the specific identity of the attachment is determined. In versions of the invention in which the attachment 41 has an attachment identification component 568 and tool 30 has a complementary reader 570, the reader performs this function.

In alternative configurations of this invention, another component performs the function of reading the data stored in the attachment identification component. For example, Applicant's U.S. Patent Application No. 60/634,588, filed 9 Dec. 2004, entitled Wireless System For Providing Instrument And Implant Data To A Surgical Navigation Unit, U.S. Patent Pub. No. 2006/0142656 A1, incorporated herein by reference discloses how an intermediate attachment reads data from the actual attachment applied to a surgical site or to an implant the tool is used to fit to the surgical site. These data are then transmitted to a static head such as navigation localizer 538.

In still another version of the invention, the attachment data are entered manually. In these versions of the invention, control processor (DSP 170) transmits a signal to the remote unit when the signal asserted from the sensor integral with the coupling assembly 41 transitions from the from the load state to the run state. The remote unit, for example the handpiece control console 542 or personal computer 544, interprets this information as an indication that a new surgical attachment 41 is attached to tool 30. Once the remote unit determines that this event has occurred, the remote unit generates a display requesting the surgical personnel identify the newly-attached surgical accessory 41, (steps not shown).

Once step 590 is executed, a step 592 is performed in which the handpiece operating parameters for the newly attached attachment are identified. Step 592 is performed by the reading of additional data stored in the attachment identification component 568. Alternatively, step 592 is performed by retrieving data in a remote lookup that, for each type of surgical attachment 41, identifies certain operating characteristics. This look-up table may be in the operating room remote unit employed to configure the tool 30 or in a file server off-site from the operating room. This operating parameter data is a function of the type of tool and attachment. For example, if motor 34 comprises the power generating unit and the surgical attachment is a bur, these data may be an initial and maximum speed for the bur. If the tool is an RF ablation device, and the surgical attachment is an ablation electrode, these data are the preferred and maximum temperatures at which the electrode should operate and the maximum current the electrode should draw.

It should be appreciated that step 592 may be performed by the manual entry of data through the remote unit.

In a step 594 these operating characteristics are displayed by the remote unit employed to configure the handpiece 30. As part of this display, and shown as a step 596, the surgical personnel are invited to accept or reset the operating characteristics of the tool based on the retrieved operating characteristics. Step 598 represents the resetting of the tools operating characteristics by the surgical personnel away from the retrieved characteristics. Thus, step 598 is an execution of step 586 in which buttons are depressed to reset the operating characteristics of the tool up or down from the retrieved characteristics.

Once, in step 596, the preferred operating characteristics are accepted or, in step 598, the characteristics are reset, a step 600 is executed. Step 598, similar to step 362, is performed in which the attachment specific parameters are loaded into the control processor (DSP 170).

From the above description, it is clear that the surgeon has the option of configuring the tool 30 to operate in a state greater than that specified by operating characteristic data specified for the attachment 41. The system of this invention provides additional feedback regarding when tool 41 is so operated. Specifically, as represented step 602, there is monitoring of when the operating state of the tool exceeds a defined state established from the retrieved operating characteristics. For example, in step 602 operation of motor 34 is monitored to determine if the motor operating speed exceeds a level based on the preferred maximum speed. This rate is, for example, between 1.0 and 2.0 times the preferred maximum operating speed.

The monitoring of step 602 may be performed by the tool control processor (DSP 170) or the remote unit, (handpiece console 542 or personal computer 544). If the monitoring is performed by the remote unit, in a separate step (not illustrated) the tool control processor sends a message to the remote unit indicating that the operating state is being exceeded.

Once it is determined that the operating state is being exceeded, the system executes steps 606 and 608. In step 606, the remote unit temporarily prevents the tool 30 from being operated beyond the defined operating state. For example, if the tool contains a motor 34, the control processor (DSP 170) does not assert signals that allow the power regulator to drive the motor above the defined speed level. If the tool is an ablation tool, the control processor does not assert signals that allow the power regulator to apply current above the defined level to be applied to the ablation electrode.

In step 608, the remote unit generates a display advising the surgeon that it appears the tool is going to be driven beyond the defined level. Surgical personnel in step 610 then must acknowledge it is the intent to so operate the tool. Once the surgical personnel enter this acknowledgment, the remote unit releases the lock on the tool operation, step 612. In step 612, the remote unit performs this function by sending an appropriate command to the tool control processor through transceiver heads 536 and 530 (or conductor 562). The tool control processor, in step 614, then releases the operating lock on the tool.

In some versions of this invention, once the acknowledgement of step 612 is entered, the system records in the event logs for the tool and the surgical procedure that the tool 30 and attachment were operated at a rate above the preferred maximum operating rate.

Figure 21:
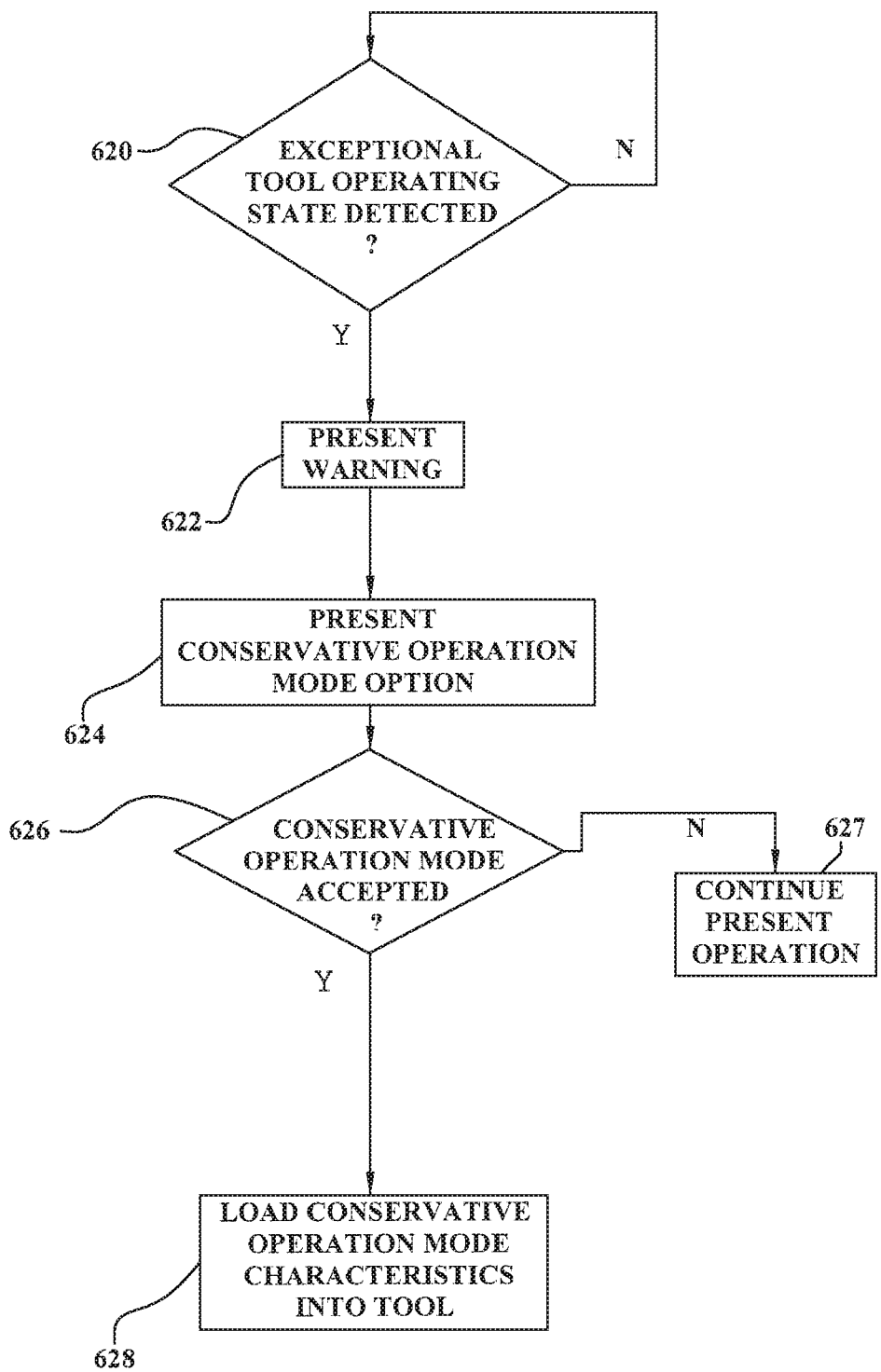
FIG. 21 is a flow chart of the process steps performed by the integrated tool system of this invention to warn and conserve operation of the tool when a tool component enters an exceptional operating state.

As represented by the process steps of FIG. 21, the remote unit also regulates the operation of tool 30 based on the monitored operating characteristics of the internal components of the tool. As discussed above, the tool control processor (DSP 170) forwards data packets to the remote unit containing information regarding the operating condition of the components internal to the tool. In some versions of the invention, these packets contain data that quantifies the operating state or condition. This type of data packet, for example, contains an exact indication of the temperature of the tool motor 34 measured by transducer 572. Alternatively, based on temperature monitoring performed by the tool control processor (DSP 170), the control processor sends a data packet whenever the output signal from transducer 572 rises above a defined level.

Similar monitoring and data packet generation is performed based the operating characteristic data received by monitoring the charge across the battery 42, the signals received from accelerometer 574, the noise detector 576 or the temperature transducer internal to the battery. Data packets may also be sent by the control processor when the control processor receives an indication that the motor is drawing an excess amount of current.

In FIG. 21, step 620 represents the detection that the tool 30 is no longer in the normal state and has entered an exceptional operating state. Examples of exceptional operating states include: a determination that the battery will soon be discharged; the battery, as indicated by a rise in its temperature; is approaching a breakdown condition; the tool 30 is at or approaching a temperature in which it will be difficult to hold; that the tool is vibrating excessively or developing excessive noise; or that the motor has been excessively heated. Still another exception operating state occurs when the power generating unit (motor 34) repeatedly draws current above the set limit level at frequency above a pre-defined level.

As mentioned, the determination of step 620 may be made by the monitoring performed by the tool control processor (DSP 170). Alternatively, the remote unit, the handpiece control console 542 or personal computer 544, may perform the monitoring of step 620 based on data transmitted by the tool control processor.

If, in step 620, it is determined that the tool is in an exceptional operating state, the remote unit, in step 622, presents a warning regarding the operation of the tool. This warning indicates the nature of the exception. For example, if in step 620 it is determined that the battery 42 is almost completely discharged, this information is presented. If, in step 620, it is determined the motor temperature is rising to a level at which it may cause motor malfunction or damage, this information is presented.

Either simultaneously with or immediately after step 622, the remote unit presents the surgeon with a conservative operation mode option, step 624. In this step, the surgeon is given the option of operating the tool at a reduced operation level in order to prevent operation of the tool from decaying or being interrupted. Typically this conservative operation mode limits the rate at which the power generating unit operates. For example, if the power generating unit is motor 34 and in step 620 it is determined that the battery is close to complete discharge or motor temperature is approaching an unacceptable level, the conservative operation is the reduction in the maximum speed at which the motor can be operated. Another example of the conservative operation mode is the reduction in the power an RF ablation probe can apply to the surgical site.

In step 626 the surgeon accepts or declines the invitation to operate in the conservative mode. A surgeon may select to decline operation of the tool in the conservative mode if it is known that tool use required for only a short time period. If the surgeon declines to accept conservative operation of the tool, operation continues as before, step 627. It should be appreciated that as part of this step, the remote unit writes data into the external tool log that the tool entered a particular exceptional state and the surgical personnel declined the invitation to have the tool placed in the conservative operation mode.

Alternatively, given that the surgeon may need the tool for extended time and the procedure is at point wherein interruption of tool operation is undesirable, in step 626 he/she accepts the conservative operation mode.

If the conservative operation mode is accepted, in step 628 the remote unit loads the conservative operating mode parameters into the tool. Step 628 is thus analogous to a re-execution of step 362 in which new operating characteristics are loaded into the tool control processor (DSP 170). Once step 628 is executed, the tool continues to operate though at the levels specified by the conservative operation mode characteristics.

This feature of the system of this invention provides a means to continue to operate the surgical tool 30 in the event the occurrence of an exceptional event may otherwise make it difficult to continue to operate the tool.

Figure 22:
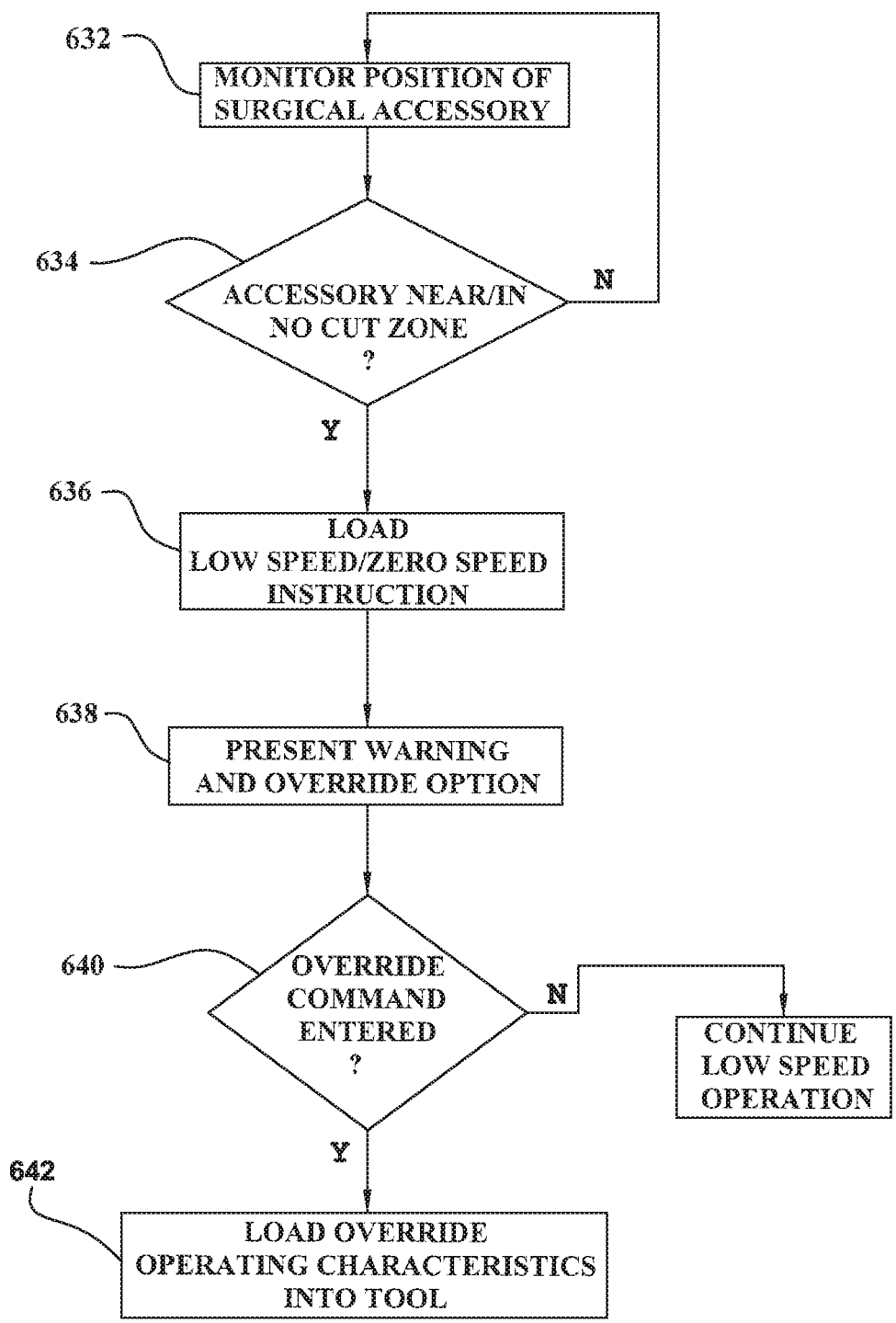
FIG. 22 is a flow chart of the process steps performed by the integrated tool to inhibit application of the tool attachment beyond application at the surgical site at which the procedure is being performed.

Surgical tool 30 of this invention, in combination with the surgical navigation system, is further configured to provide the surgeon with notice when the surgical attachment is approaching or at body location at which the attachment should not be applied. As represented by step 632 of FIG. 22, during the surgical procedure, surgical navigation console 540 monitors the position of the surgical accessory 41. This monitoring is performed based on the tracker 539 attached to the tool 30, to the accessory or to the intermediate accessory between the tool and the accessory actually applied to the site.

Prior to the initiation of the procedure, the surgical navigation processor 540 is provided with map data that indicates the body locations adjacent the surgical site to which the surgical attachment should not be applied or should only be applied with extreme care. Collectively, these areas are referred to as "no cut zones". (Step not shown)

In step 634, based on the accessory position data acquired in step 632, surgical navigation processor 540 determines if the attachment 41 is at or has crossed the boundary of a not cut zone.

If the surgical attachment 41 is so positioned, the surgical navigation console 540, in step 636, loads a low speed or zero speed instruction into control processor (DSP 170) of tool. Step 636 is thus a re-execution of step 362. In step 636, the tool control processor (DSP 170) is loaded with data indicating that the tool is to either be deactivated or, at a minimum, run at very low operating rate. For example if the power generating unit is motor 34, the control processor is loaded with instructions indicating the motor is to be run at either a low speed, (motor maximum speed is appreciably lowered) or totally deactivated. If the power generating tool is an RF ablation probe, the instructions loaded in step 636 are typically instructions that the tool should be deactivated. Based on these instructions, the control processor generates the appropriate USER_SPEED signals to the power regulator (MCC 172). The power regulator, in turn, appropriately resets the operation of the tool power generating unit. (Steps not shown).

The execution of step 636 by the surgical navigation unit 540 and the subsequent reduction in operation of the tool 30 are performed to immediately minimize, if not prevent, the extent to which attachment 41 is active in the no cut zone.

Essentially simultaneously with the execution of step 636, in a step 638, a warning is presented. Typically this warning is presented of the display integral with the surgical navigation processor 540. In step 638 this warning contains in indication that use of the tool has been reduced or totally blocked because the attachment 41 is at or has entered the no cut zone.

Integral with the warning, also in step 638, the surgeon is also presented with an override option. The override option allows the surgeon to continue to operate the tool even though the attachment 41 is near or has crossed into the no cut zone. Step 640 depicts the process in which the surgeon selectively accepts the override option. If this option is not selected, operation of the tool continues based on the commands entered in step 636.

Alternatively, in step 640, the surgeon enters the override command. If this event occurs, in step 642, a remote unit, the surgical navigation controller processor 540, the handpiece control console 542 or the personal computer 544, loads override operating characteristics in the tool control processor (DSP 170). These characteristics, which are predefined, limit the use of the surgical attachment at or near the no cut zone. For example, if in step 636 use of the tool is totally blocked, in step 640, the override characteristics may allow operation of the tool to continue however at a lower operating rate.

Alternatively, the instructions loaded in step 636 may have only caused the control processor to reduce the rate at which the tool power generating unit operates. In this event the instructions loaded in step 642 direct the control processor to allow the power generating unit to operate at a higher rate than that specified in the instructions of step 636. In step 642, the new instructions may even direct the control processor to allow the power generating unit to continue to be operated at the defined rate before step 636 was executed.

IV. Kinematic Machine Positioning

Figure 23:
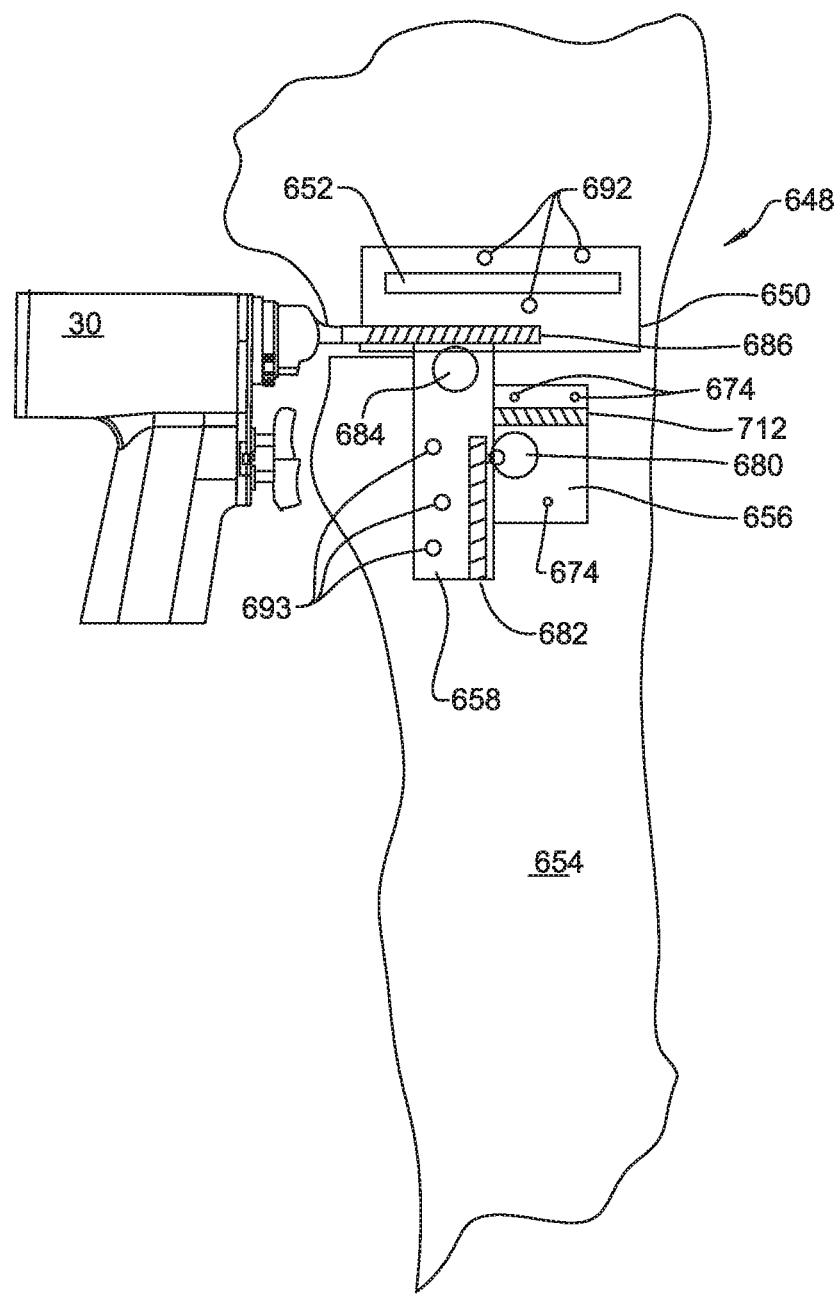
FIG. 23 depicts how the integrated system of this invention is used to facilitate the positioning of a kinematic machine such as the illustrated jig.

The integrated system of this invention is used to precisely position a kinematic machine that is fitted to a patient. Typically, a kinematic machine has at least one and often two or more moveable links that are selectively positioned relative to a static point on the body of the patient. By precisely locating the links, a therapeutic task is accomplished using the machine. FIG. 23 illustrates one such kinematic machine, a jig assembly 648. Jig assembly 648 includes a fixed marker block 656 and a jig head 650 that is moveable relative to the mounting block. Jig head 650 is formed with a guide slot 652. During the process of attaching an implant to a bone 654, jig head 650 is precisely positioned. Once the jig head 650 and guide slot 652 are so positioned, a saw blade is inserted in the guide slot 652 to remove a section of the bone in order to create a space in which the implant is fitted.

The marker block 656 is mounted to the bone 654. The jig head 650 is moveably attached to a positioning block 658 that itself is moveably attached to the marking block 656. The integrated system of this invention is used to precisely position jig head 650 to ensure the tissue is cut at the appropriate location.

Figure 24A:
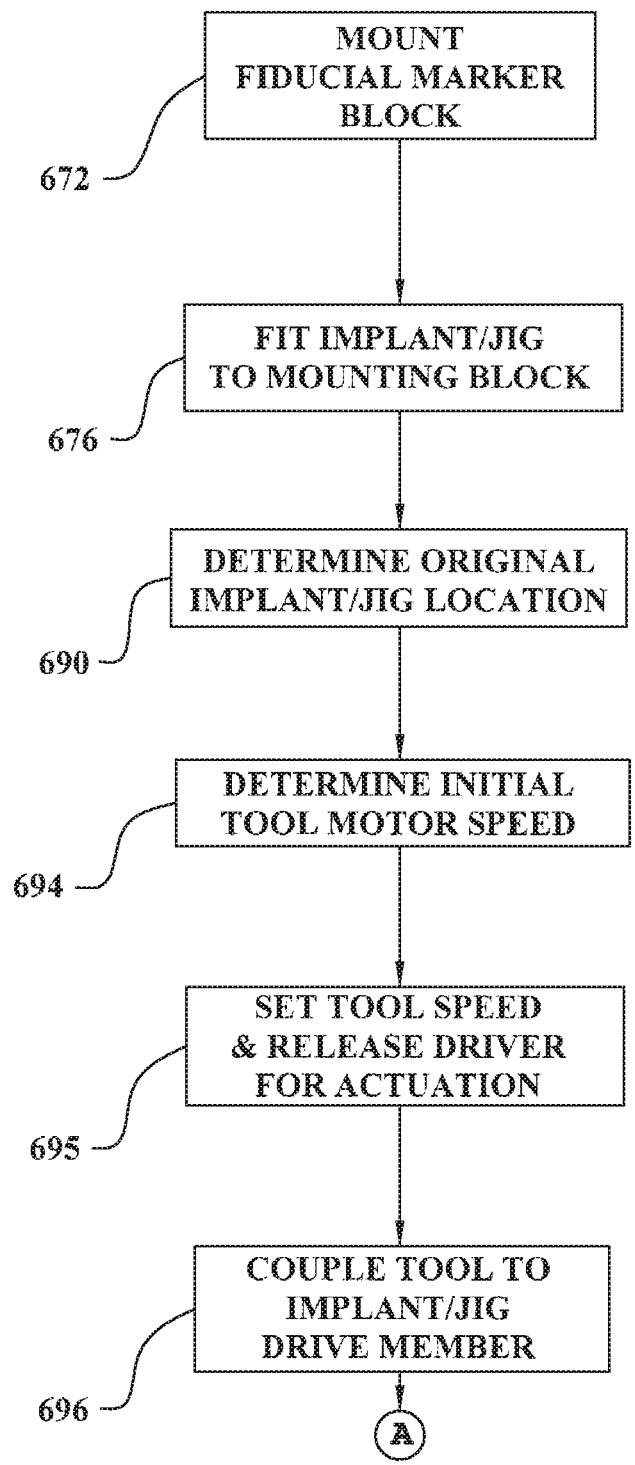
FIGS. 24A and 24B collectively form a flow chart of the process steps executed by the system to position a surgical implant or other surgical device.

As represented by step 672 of FIG. 24A, the integrated process of this invention starts with the mounting of the marker block 656 to a fixed location. Typically, this location is a position on the body, for example, to a section of bone 654. Usually, the surgical navigation system is employed to facilitate the positioning of the marker block at a location close to where the surgical component, here the jig head 650 is to be located. In one version of the invention, pins 674 integral with the marker block 656 are used to hold the marker block to the bone 654.

In a step 676, the jig head 650 or other surgical device or surgical implant is fitted to the marker block 656. In one version of the invention the jig head 650 and marker block are provided with complementary feet and grooves (not illustrated). The feet of one of the jig head 650 or marker block 656 are dimensioned for a close sliding fit in one or more grooves formed in the other of the marker block 656 or jig head 650. Other means may be provided to facilitate the close sliding fit of these two components.

In the illustrated version of the invention, jig head 650 is moveably attached to the positioning block 658 and the positioning block 658 is moveably attached to the marker block 656.

In addition to a coupling assembly that allows jig head 650 to move relative to marker block 656, these two components are collectively provided with a complementary drive assembly. This drive assembly allows jig head 650 to move relative to the marker block 656. In the disclosed versions of the invention, there are two drive assemblies. A first drive assembly vertically moves positioning block 658 relative to marker block 656. In FIG. 23, this drive assembly is represented by a circular gear 680 rotatingly mounted to the marker block 656 and a worm gear 682 rotating to the positioning block 658. A second drive assembly moves horizontally moves jig head 650 relative to the positioning block 658. This drive assembly is represented by a circular gear 684 rotatingly mounted to the positioning block 658 and a worm gear 686 rotatingly fitted to jig head 650.

Once the jig assembly 648 is fitted to the patient, in step 690 the surgical navigation unit determines the original location of the jig head. In FIG. 23 jig head 650 is shown as having three LEDs 692. The LEDs 692 represent a tracker built into the jig head 650. Positioning block 658 is also shown as having three LEDs 693. LEDs 693 facilitate the determining of the position of the positioning block 693 with the surgical navigation unit.

In a step 694 an initial displacement rate for the jig head 650 is generated. This displacement rate may be generated by one of the remote units such as the surgical navigation console 540, the handpiece control console 542 or personal computer 544. The displacement rate is based on the previously set position on the patient at which the jig head 650 should be positioned and the current position of the jig head 650 obtained in step 690. Generally, the initial displacement rate is inversely related to original distance of the jig head (or implant) relative to the previously determined final location. Also in step 694 an initial speed for the handpiece motor, based on the initial jig head displacement rate is determined. In a step 695, the initial handpiece motor speed is loaded into the handpiece control processor (DSP 170). A message is also displayed indicating that these tasks were executed.

In a step 696, the surgical tool 30 is attached to the drive assembly. In FIG. 23, this is represented by the coupling of surgical tool 30 to the worm gear 686 of jig head 650. This coupling is accomplished by providing the drive assembly and the moving member of the surgical tool with complementary coupling features. For example, the proximal ends of worm gears 682 and 686 are provided with closed end square shaped bores. The drive shaft of the surgical tool 30 has a distal end square shape that allows the shaft to closely slip fit into the proximal end bores of the worm gears 682.

Once step 696 is executed, in step 698, the surgeon actuates the surgical tool 30 so as to position jig head 650. In the versions of the invention in which, in step 694 jig head displacement rate/motor speed are calculated and loaded, upon the depression of the trigger switch 46 or 47 to actuate the tool, the control processor (DSP 170) automatically sets the USER_SPEED so that motor 34 runs at the specified speed. The mechanical energy output by the surgical tool is employed by the drive assembly to move the jig head 650 to the appropriate final position, (step not shown).

Throughout the time in which jig head 650 is displaced, the surgical navigation system monitors the position of the jig head, step 702. In a step 704, the surgical navigation console 540 or the handpiece control console 542, based on the changes in distance between the jig head and the target position, updates the jig head displacement rate/motor speed. As part of step 704, command data setting the new user speed are continually transmitted to the handpiece control processor (DSP 170). Based on these data, the control processor continually resets the USER_SPEED signal. Thus, as the jig head 650 approaches the target position, the speed at which it moves decreases.

Figure 24B:
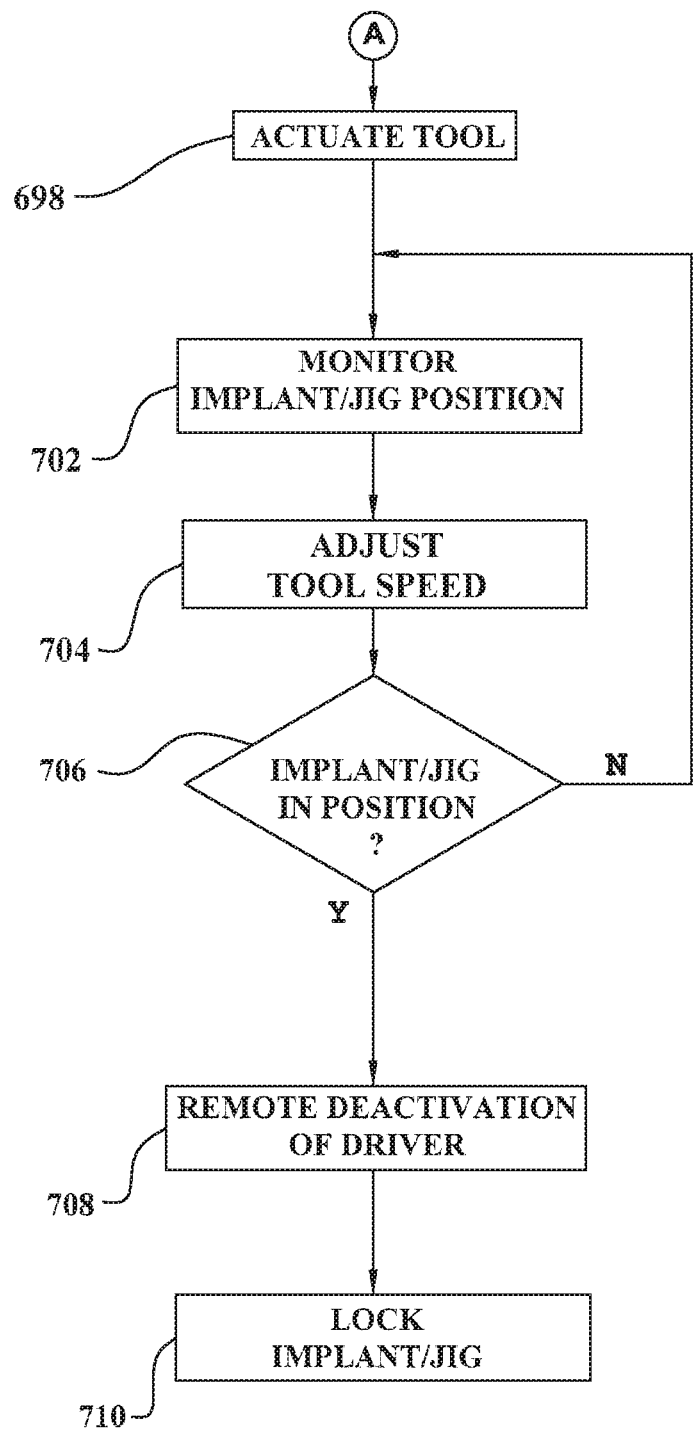

Eventually, the surgical navigation processor 540, in step 706 determines the jig head reaches the target position. In FIG. 24B, this is represented by the loop backed repetitive execution of steps 702, 704 and 706. Once the event occurs, the surgical navigation processor 540 or handpiece control console 542 sends a deactivation command to the surgical tool, step 708. Upon receipt of this command, control processor (DSP 170) sets the USER_SPEED signal to zero. This causes power regulator (MCC 172) to deactivate and brake the motor rotor 78.

A step 710 is then executed to clamp the jig head 650 in the desired position. In FIG. 23, a set screw 712 is shown as extending through marker block 656. Set screw 712 is positioned to bear against positioning block 658. The set screw 712 thus functions as the clamping member that holds positioning block 658 in the correct position. A similar set screw, not illustrated, can be used to hold jig head 650 in position.

This configuration of the integrated tool system of this invention uses the motorized surgical tool 30 to precisely position a surgical component or implant. Once the kinematic machine is so positioned, the tool 30 is deactivated.

Other kinematic machines the system and method of this invention can be used to position include body fixator units. One such type of an assembly is halo type unit used to hold the skull static relative to the collar bone. Other kinematic machines are used to hold spinal disks in fixed positions relative to each other. Still other kinematic machines hold fractured bone fragments together. It should likewise be appreciated that the method of FIGS. 24A and 24B is not limited to the positioning of kinematic machines. The system and method of this invention may also be used to precisely position in an implant relative to body tissue markers.

V. Integrated Cement Mixing

Figure 25:
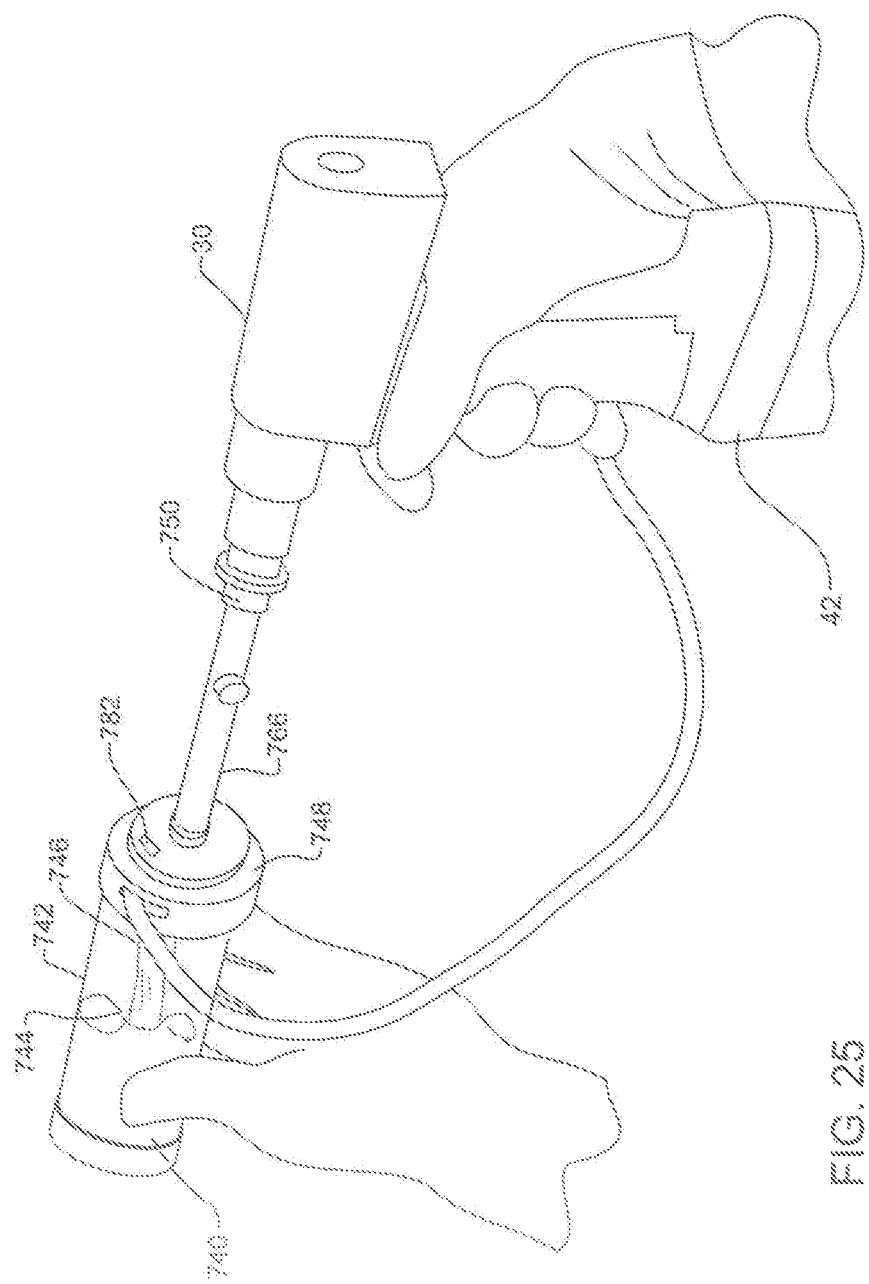
FIG. 25 is a perspective view of how a surgical tool of this invention is used to mix orthopedic cement for a predetermined amount of time and monitor the viscosity of the cement.

A system with surgical tool 30 of this invention is also used to mix surgical cement as seen by reference to FIG. 25. Here, the cement powder 740 is contained in a cartridge 742. A monomer (not illustrated) is also placed in the cartridge 742. A blade 744 in the cartridge mixes the cement powder and monomer together to form an uncured mass of cement. A shaft 746 attached to the blade 744 extends out of cap 748 disposed over the cartridge. 30. Surgical tool 30 is actuated at a select speed for a select Shaft 746 is coupled to an output shaft 750 of the surgical tool amount of time to so that, at the end of the mixing process the cement mass hardens, sets, at the desired rate and when hardened, has the surgeon-selected desired porosity and opacity.

Figure 26A:
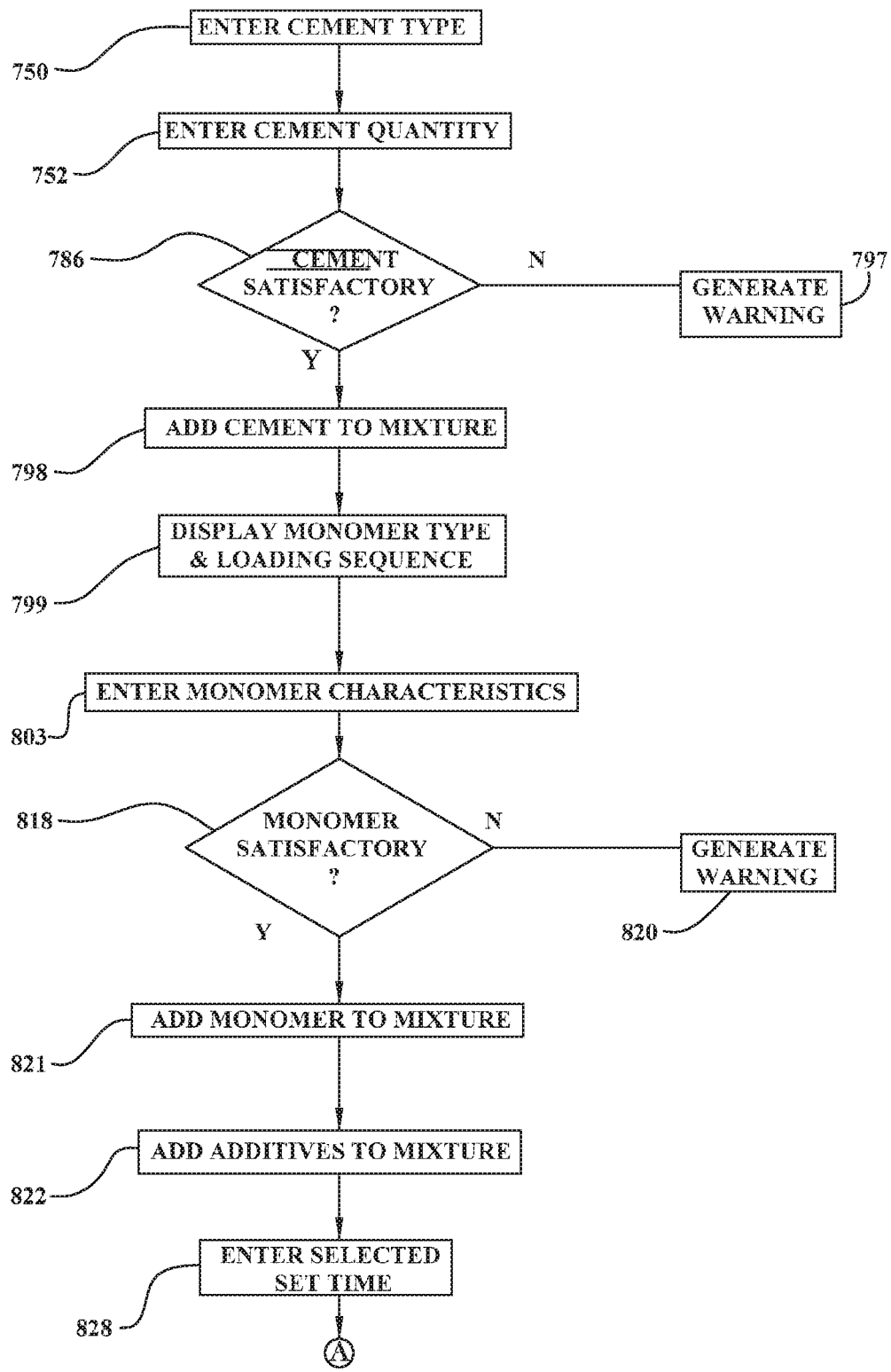
FIGS. 26A, 26B and 26C collectively form a flow chart of the process steps executed by the surgical tool system of this invention to ensure the cement is mixed for an appropriate amount of time and to monitor the viscosity of the cement.
Figure 26B:
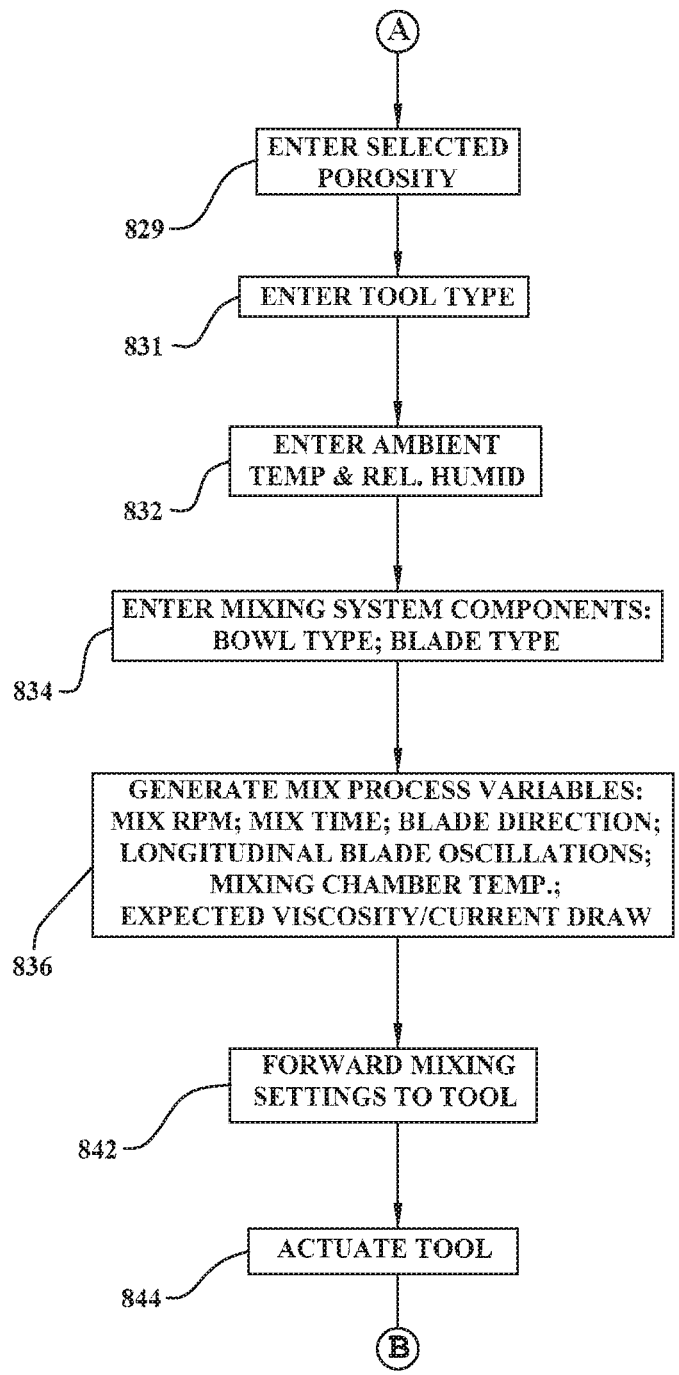
Figure 26C:
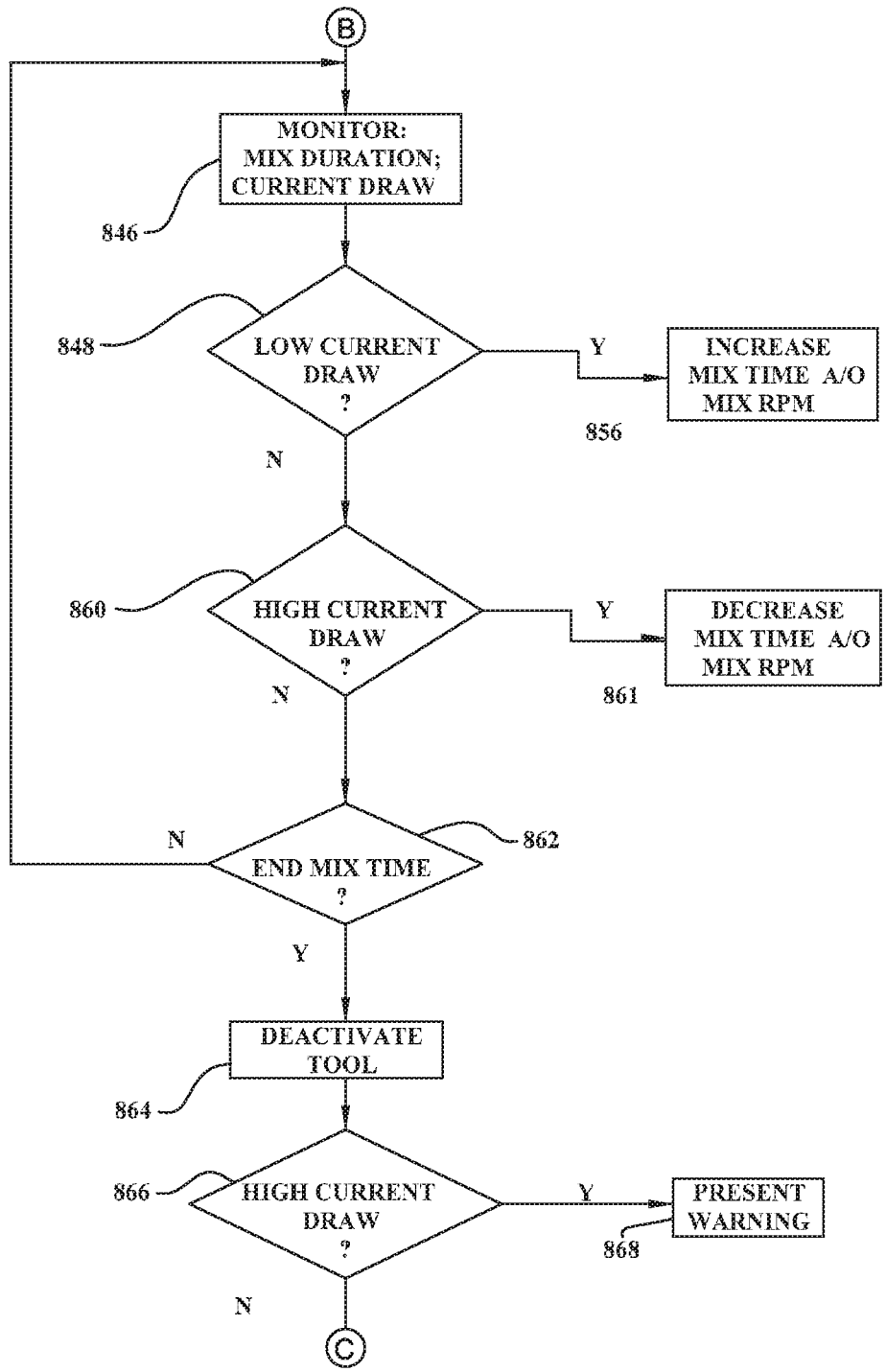

FIGS. 26A, 26B and 26C collectively form a flow chart of the process steps executed by the system of this invention to facilitate the proper mixing of the cement. The process starts with, in steps 750 and 752, respectively, the entry of the type of and quantity of cement to be mixed. There are number of means by which steps 750 and 752 are executed. In one version of this invention, cement type and quantity information are entered by depressing specific touch screen buttons on one of the components of the system such as the handpiece control console 542, personal computer 544 or pendant 548.

Figure 27:
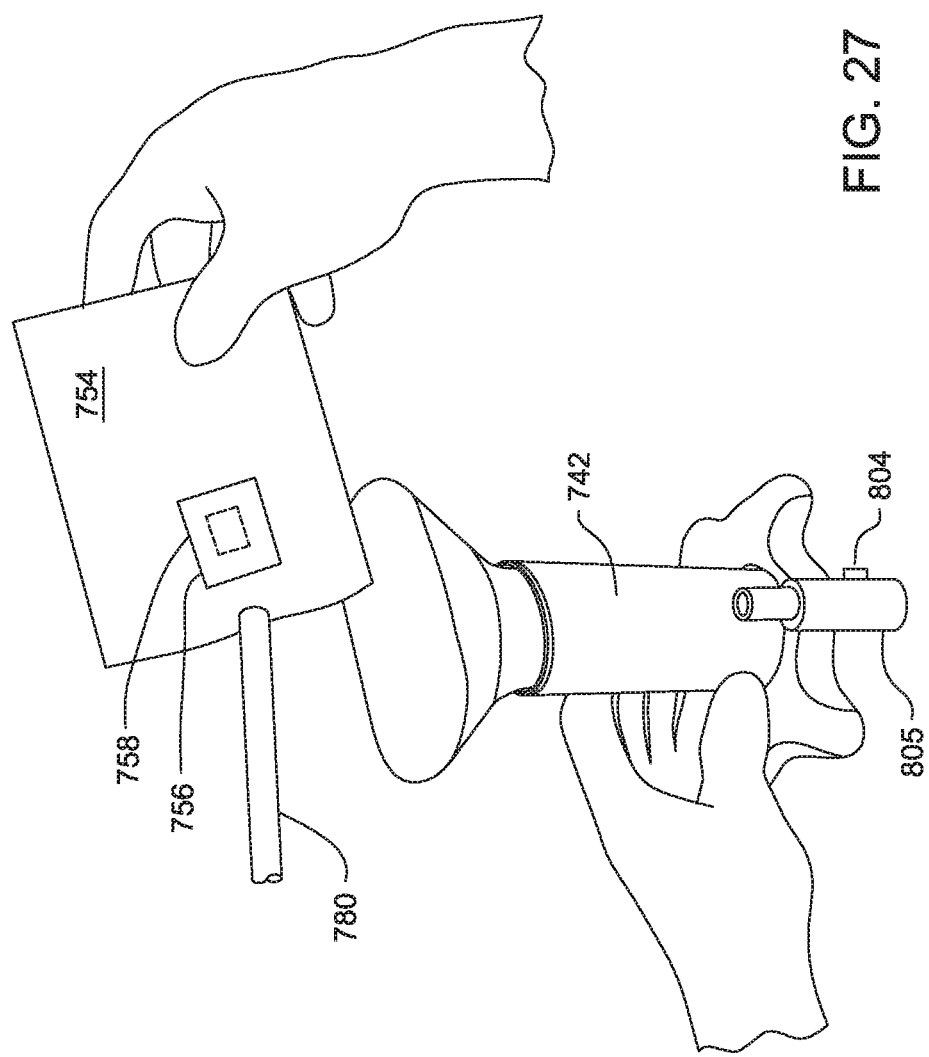
FIG. 27 is a perspective view of how data regarding the characteristics of the components forming the cement to be mixed are supplied to the system.

Alternatively, as represented by FIG. 27, these data may come from the packets 754 in which the cement is held prior to mixture. Here, attached to the packet 754 is a radio frequency identification chip (RFID) 756 such as is available from Philips Semiconductor. RFID 756 is disposed over packet 754. A small piece of RF permeable protective material 758 such as paper or plastic is disposed of the RFID 756 to hold the RFID in place.

Figure 28:
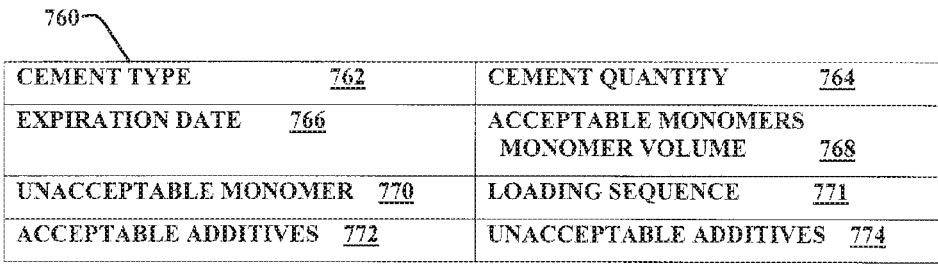
FIG. 28 depicts some of the data types stored in the data storage device integral with the packet containing surgical cement.

Internal to RFID 756 is a memory represented by the table 760 of FIG. 28 in which data describing the characteristics of the cement are stored. These data include an indication of the cement type, represented by field 762. Data representing cement quantity are stored in field 764. An expiration date for when the cement can last be used are stored in field 766. Data indicating the monomers that should be mixed with the cement, or that at least are preferred for mixture with the cement, are stored in field 768. Field 768 also contains data regarding the quantity of monomer that should be mixed with the given packet of cement. Data regarding monomers that should not be used to harden the cement are stored in field 770. Field 772 stores data that describes acceptable additives that can be combined with the cement. Field 774 contains a list of additives that cannot be combined with the cement.

The RFID 756 is scanned by a reader (not illustrated) in a probe 780. Probe 780 and reader are connected to another component of the system such as handpiece control console 542 or computer 544.

Alternatively, in some versions of the invention, cartridge 742 contains a premeasured quantity of the cement powder 740. In these versions of the invention, an RFID 782 is integrally associated with the cartridge. RFID 782 may be housed in the cartridge cap 748. In these versions of the invention, data may be read by the RFID reader in the surgical tool 30 or the reader in the probe 780. In some variations of this version of the invention, RFID 782 is attached to the packaging in which the cartridge 742 is stored. Here, steps 750 and 752 are performed with probe 780.

Once steps 750 and 752, the system, in step 786, determines if the cement 720 is appropriate for the procedure being performed. In step 786 a number of separate evaluations are performed. One evaluation is to determine based on the data in RFID expiration field 766 whether or not the expiration date for the use of the cement has passed.

Also, based on other data, in step 786 determination is made regarding whether or not the cement type and quantity are appropriate for the procedure. The reference data from which these determinations are made may come from data entered by the surgical personnel entered before the procedure. Alternatively, these data may be obtained from another component or instrument used to perform the procedure. For example, the previously mentioned and incorporated-by-reference Applicant's U.S. patent application Ser. No. 10/214,937, SURGICAL TOOL SYSTEMS WITH COMPONENTS THAT PERFORM INDUCTIVE DATA TRANSFER, filed 8 Aug. 2002.

Figure 29:
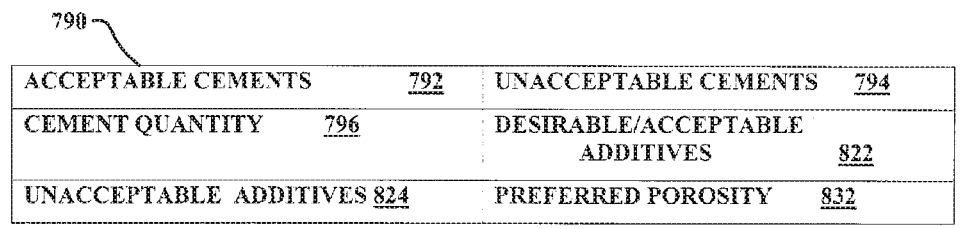
FIG. 29 depicts some of the data types stored in the data storage device integral with the container storing the monomer used to cure the surgical cement.

U.S. Pat. Pub. No. 2003/0093103 describes how surgical implants are provided with RFIDs. FIG. 29 is a partial listing of some of the data stored in a memory 790 of one of these RFIDs. As represented by field 792, these data include an indication of the type of cement that can be used to attach the implant. Data indicating the cements that should not be used are stored in field 794. A field 796 stores data indicating the quantity of cement typically required. If the implant fitted in the procedure is of the type having the data of memory 790, then prior to step 750, the system, for example personal computer 544 displays the preferred cement type and quantity data.

If it is determined that the cement is unacceptable, the system displays a warning as represented by step 797. In step 797, the warning indicates the cause of the warning, for example, wrong cement, out of date cement or recalled lot. Not shown are steps performed by the surgical personnel after the warning is presented. The surgical personnel may decide to mix a new batch of cement, restart the process. Alternatively, the surgical personnel may decide the cause of the warning does not warrant the restart of the mixing process, for example, if the cement expiration date only recently passed. In such a circumstance, the surgical personnel press an acknowledgement button presented with the warning display. The entry of the acknowledgement is then recorded on the log for the surgical procedure. In FIG. 26A, the steps executed after the generation of the warning, step 797 are not shown. Step 798 is the adding of the cement into the mixing unit, for example cartridge 742.

Once it is determined that the cement is satisfactory, the system, in step 799, displays indications of the monomers it is acceptable to mix in with the cement and the sequence in which the cement and monomer should be initially loaded in the mixing unit (cartridge 722). These data may be preprogrammed into the system. Alternatively, as represented by fields 768 and 771 of memory 760, these data may be stored in and retrieved from the RFID 756 integral with the cement.

Figure 30:
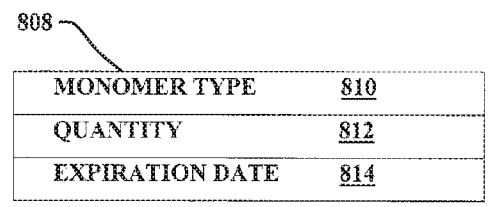
FIG. 30 depicts some the data types stored in the data storage device integral with a surgical implant.

When it is time in the sequence to enter the monomer, data regarding the characteristics of the monomer are input into the system, step 803. This step may be performed manually. Alternatively, an RFID 804 attached to the container 805 in which the monomer is stored is read. This RFID 804 is read by the same component used to read cement packet RFID 756. RFID 804 includes a memory represented by table 808 of FIG. 30. Internal to the monomer RFID memory 808 are: a data field 810 indicating monomer type; a data field 812 indicating monomer quantity; and a data field 814 indicating expiration date. Not illustrated by also understood be in RFID memory 806 as well as memory 760 of cement RFID 756 are data fields in which information regarding manufacturer and manufacturing lot number are stored.

Once step 803 is executed, the system performs a step 818 to determine if the monomer is acceptable. This step is performed based on previously obtained reference data. These reference data may be hard stored in the system, stored prior to the procedure or the data obtained from the cement RFID 756. If in step 818 it is determined the monomer selected for addition is not acceptable, the system displays a warning, step 820. Step 820 is similar to step 797 in that the surgical personnel are given a notice of the cause for the warning. The surgical personnel can then decide to use the monomer or select a new container of monomer. If the surgical personnel elect to use the potentially questionable monomer, an acknowledgement is entered. The steps executed after the execution of step 820 not shown.

If in step 818 it is determined that the monomer is acceptable, it is added to the mixing unit (cartridge 742), step 821.

While the steps are not shown, it should be understood that the system and method of this invention also monitor the volume of monitor added to the cement mixture. The volumetric determination is made by assuming all the monomer, as indicated in quantity field 812 is added to the mixture. If this volume is either too much or great for the quantity of the cement as specified in field 768, an appropriate warning message is displaced. If this evaluation indicates too much monomer has been added to the system, this system thus provides has notice so a decision can be made regarding whether or not the mixture should be discarded. If the evaluation indicates that too little monomer has been added, the notice provides an opportunity to add additional monomer.

After the cement and monomer are placed in the mixing unit, additives may also be placed in the unit as represented by step 822. One additive sometimes including in a cement mixture is therapeutic, for example an antibiotic. Another type of additive that may be included is material designed to improve the ability of a medical imaging unit to capture an image of the cement. Barium sulfate is sometimes added to cement for this purpose.

In FIG. 26A, the addition of the additives is shown as a single step 822. It should be appreciated that in the system and method of this system, an image may be presented indicate the need to include the additive or the process is not at a point where the additives are to be added. Data regarding the characteristics of the additives to be added are entered using manual or electronic means similar to how the data regarding the cement powder and monomer are entered. RFIDs integral with the containers in which the additives are stored are read. Once the system is provided with the additive-describing data, a step similar to step 818 is performed to determine if the additive and/or quantity of the additive(s) are acceptable.

The reference data by which this determination is made may come from fields 772 or 774 of the cement RFID memory 760. Alternatively, these reference data are read from fields 823 and 824 of implant RFID memory 808. Here, field 823 contains data indicating the additives that are acceptable for use or desirable/required for use with the implant. Field 824 contains data describing additives that are not appropriate for use with the implant. It should be appreciated that fields 772 and 823 also contain data indicating the volume or mass of additive that should be added to ensure an effective amount is present. Similar data describing acceptable, desirable, required and unacceptable data are also stored in the some of the RFIDs 804 associated with the monomer containers.

Step 822, it should also be understood, includes the sub step of verifying the additive is appropriate for inclusion into the cement forming mixture and that a sufficient quantity of the additive has been included.

It should also be appreciated that the above process steps may be repeated and/or re-executed in a different sequence. The exact number of times the above steps are re-executed and their execution sequence are a function of the quantity of the cement to be mixed and the sequence in which the cement, monomer and additive are to be added to the mixing unit (cartridge 722). Some cements and monomers are mixed in alternating orders. Other cements and made by first adding all the powder and then all the monomers. Such sequence data (obtained from cement RFID 756) and quantity data, (obtained from implant RFID memory 790) are used by the system to initially determine the sequence in which the initially components adding steps are performed. It should be appreciated instructional data indicating the sequence for performing these steps are presented by the system on one of the displays.

Once the materials that are mixed to form the cement mixture are added to the mixing unit, a surgeon-selected set time is entered into the system as represented by step 828. "Set time" is the amount of time, post-mixing, before the uncured cement has its peak exothermic reaction. The occurrence of this event means that the cement has hardened to a point at which it can no longer easily be molded. The "working time," the time in which the cement can easily be molded into shape, is directly proportional to and less than the set time.

In step 829, data are entered into the system indicating the desired porosity of the cured cement. These data may be entered or based on the data in field 832 of the implant RFID memory 790. In some versions of the invention, step 829 starts with the display of the porosity level retrieved from implant memory field 831. The surgeon then accepts the recommended level or adjusts the level based on the particulars of the present surgical procedure. In versions of the invention wherein the implant does not provide porosity level, the system, in step 829, directs the surgeon to enter a selected porosity level.

The system, in step 831 also determines the characteristics of the tool employed to perform the mixing. These data are entered by pressing the buttons presented on the touch screen display. Alternatively, these data are known by the system based on tool identifying characteristic data provided by the tool control processor (DSP 170) through data transceiver head 530.

In step 832, the ambient temperature and relative humidity are entered into the system. These data are entered manually. Alternatively, an environment monitor 833 is in the operating room and connected to one of the other units, (handpiece control console 542 or personal computer 544). Environmental monitor 833 contains transducers sensitive to temperature and humidity. The output signals generated by these transducers are forwarded to the system unit controlling and monitoring the cement mixing process. In this construction of the system, step 832 is performed without human participation.

In step 834 the particularities of the mixing system are entered into the system. These particularities include: type of mixing unit (bowl or cartridge); blade type; presence of blade oscillating unit; presence of heater.

Based on the above data, the system, in step 836, generates the mixing process variables. These variables include: the speed at which the motor 34 should be actuated; the mix duration, the total time the motor should be actuated; and the blade direction; (unidirectional or cyclic forward/reverse/forward/reverse. If the mixing system is capable of longitudinally oscillating the blade the oscillation rate is determined. If the mixing unit has a heater, the temperature to which the mixing unit should be heated in determined.

In step 836, the above mixing variables are determined based on data stored in look-up tables contained in a component such as personnel computer 544. Alternatively, or in combination with the look-up table data, the mixing variables are determined based on execution of stored algorithms. The data entered in steps 750, 752, 803, 822, 828, 829, 831, 832 and 834 and/or from the look-up tables function as the input variables for the algorithms.

The look-up table and algorithm constants, coefficients and exponents are typically determined by empirical analyses. Table 1 lists general relationships between the above-described variables and the rate at which the motor 34 should be operated and/or mix duration.

TABLE 1

General Relationships Between Input Variable For Cement Mix And Mix Speed (Motor RPM) And Mix Duration

| Type of Cement, i.e., Increased Cement Viscosity | Higher Mix Speed and/or Longer Mix Duration |
|---|---|
| Increased Cement Quantity | Higher Mix Speed and/or Longer Mix Duration |
| Addition of Additives | Higher Mix Speed and/or Longer Mix Duration |
| Decreased Set Time | Higher Mix Speed and/or Longer Mix Duration |
| Reduced Porosity | Higher Mix Speed and/or Longer Mix Duration |
| High Ambient Temperature | Slower Mix Speed and/or Shorter Mix Duration |
| High Ambient Rel. Humidity | Higher Mix Speed and/or Longer Mix Duration |

Motor speed and mix duration is also a function of tool type. For example, if the attached tool is a slow speed reamer the mix duration may be longer than if the tool is drill that is typically run at a higher speed. Variables such as mixing system components such as blade type and type of mixing unit have varying effects of mix speed and/or mix duration.

Generally, if a relatively short set time for the cement is desired, the system determines the mixing unit heater decrease the temperature of the compounds being mixed. The rotational direction of the blade and whether or not it should be longitudinally oscillated are generally functions of cement type, the type(s) of additive(s), and blade type.

Figure 31:
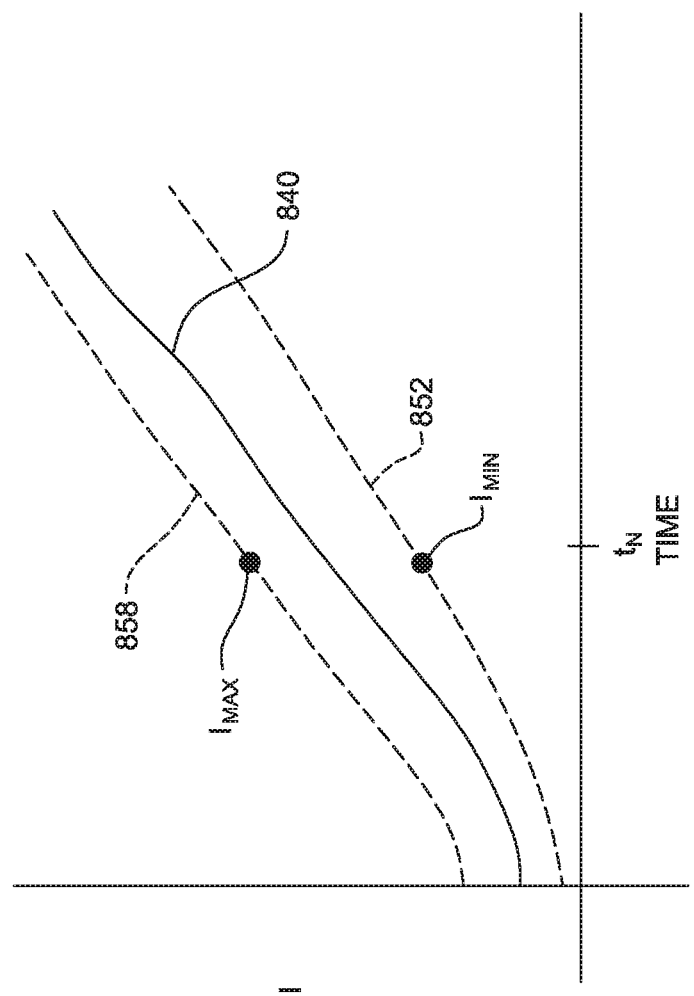
FIG. 31 is a plot of the change of current drawn over time when the system of this invention is employed to mix surgical cement.

Also in step 836, the viscosity of the mixed cement at the end of the mixing process is determined. Again, this is generally determined by empirical process. Look-up data based on the empirical processes are stored in the system, for example personal computer 544 or in a central database in the hospital. Based on these data, a determination of a current that should be drawn by the tool motor 34 is also generated in step 836. In some versions of the invention, only these latter data are generated. In preferred versions of the invention, the system generates data representative of the current the motor should draw over time during the actual mixing process. Plot 840 of FIG. 31 represents one such set of data.

In step 842, the system then forwards the mix settings to the tool control processor (DSP 170). At a minimum, in step 842, the system provides the tool control processor with data indicating the speed at which the motor should be driven as determined in step 836. If the blade to be forward/reverse/forward/reverse cycled, the minimal data also includes preloading into the control processor an indication of how long the motor should be rotate in each direction. In step 842, the system may further provide the tool control processor with data indicating the determined mix duration. Also as part of step 842 is the display by the system that the tool is set to mix the cement.

The next step, step 844, is the actuation of the tool to perform the mixing. It should be appreciated that before the mixing, the blade shaft 746 is coupled to the tool shaft 750 to affect the desired rotation of the blade, (step not shown).

Since the tool speed has already been set, the surgical personnel do not have exert mental or physical effort to precisely depress the trigger switch 46 or 47 to ensure the motor turns at the right speed and/or duration. Based on the preloaded instructions, control processor (DSP 170) asserts the appropriate USER_SPEED and FORWARD and REVERSE signals to power regulator (MCC 172). Thus, the pre-loaded instructions cause the motor 34 to turn at the right speed and in the right direction (or directions).

Once the surgical tool is actuated, the system, as represented by step 846, monitors both for how long the tool is actuated and the current drawn by the handpiece motor. In some versions of the system of the invention, these data are transmitted to the remote unit (handpiece control console 542 or personal computer 544).

Steps 848 and 850 represents that, throughout the mixing process, the system, typically the remote unit, monitors the current drawn by the handpiece motor 34. Specifically, in step 848, the system monitors a determination is made regarding whether or not the current drawn is significantly below the expected current draw at the given time during the mixing process. In FIG. 31, the acceptable minimal current draw is shown by dashed plot 852. Thus at time $t_N$, the acceptable minimal current drawn is $I_{MIN}$. If the current drawn is below the acceptable minimal current drawn level, the cement is most likely less viscous then it should be at that time in the mixing process. If the cement is in this state, the system responds by executing step 856 in which instructions are generated to increase the time of mix duration and/or motor RPM. (Not shown are the steps transmitting these instructions to the tool 30 and their execution by the tool.)

In step 860, the system determines if the drawn current exceeds a maximum level for the time point in the mixing process. In FIG. 31 the maximum current draw at any time is represented by dashed plot 858. At time $t_N$ the acceptable maximum current draw is $I_{MAX}$. If the current drawn is above the acceptable maximum level, the cement mixture is most likely more viscous than it should be at this point in time in the mixing process. If the cement is in this state, the system, in step 861, generates instructions to reduce the time of mix duration and/or motor RPM. (Not shown are the steps transmitting these instructions to the tool 30 and their execution by the tool.)

The system also monitors if the surgical tool performing the mixing has been actuate for a time equal to the mix duration, step 862. Once in step 862 it is determined that the cement is mixed for the select duration, surgical tool 30 is deactivated, step 864. This deactivation may occurred based on the tool control processor (DSP 170) generating a zero speed USER_SPEED signal automatically at the end of the mix time based on the stored instructions. Alternatively, the remote unit generates a specific instruction to the surgical tool 30 instructing the control processor to assert the zero speed USER_SPEED signal.

The current drawn by the tool motor 34 immediately prior to the deactivation of the tool 30 is also again tested, step 866. In step 866, this current drawn is tested to determine if it is above the acceptable level expected at the end of the mixing process. The system interprets a positive determination as indicating the mixed cement has a viscosity higher than expected. This means the mixed cement will be more difficult to work and have a shorting set time. Thus, if the determination of step 866 is positive, the system, in step 868, presents a warning regarding the exception state of the cement. If the surgical personnel elect to use the cement, they enter an acknowledgement into the system, step not shown.

If the evaluation of step 866 tests negative, then the cement has an acceptable viscosity. The system, as represented by step 870, generates a message indicating that the cement mixture is satisfactory.

Once the cement mixing is complete, the system, in step 872 determines the expected set time. One input variable made to make this determination is the last measure of current drawn by the motor 34. As discussed above, these data are proportional to the final viscosity of the cement. The other input variable used to make this determination are previously entered data: cement type; ambient temperature; ambient relative humidity; additives including quantity; and (if present) mixing unit heater temperature.

The determination of set time in step 872 is performed using methodology similar to that employed in step 836 to determine mix duration. Empirically derived reference data are used to generate the look-up tables, constants, coefficients and/or exponents used in step 872 to determine set time. Table 2 lists general relationships between uncured cement post-mix and set time.

TABLE 2

General Relationships Between Cement Post-Mix Input Variables And Set Time

| | |
|---|---|
| Type of Cement, i.e., Increased Cement Viscosity | Shorter Set Time |
| High Motor Current Draw At End Of Mix | Shorter Set Time |
| Addition of Additives | Longer Set Time |
| High Ambient Temperature | Shorter Set Time |
| High Ambient Rel. Humidity | Shorter Set Time |
| Mixing Unit Heater | Shorter Set Time |

Once the set time is determined, step 872 concludes with a display of this time. It should be understood that step 872 may be performed as a substitute for or after the current draw test of 868. In these versions of the invention, if it is determined that the set time is too short, for example only 80% or 90% of the surgeon selected set time, warning display step 870 is then executed.

It should likewise be understood that, based on surgeon preference, in step 872 the system calculates and displays cement working time.

In a step 874 the system, (personal computer 544) clocks down the display indicating the set time. The system also monitors when the time approaches the expected set time, step 876. As the set time approaches, in step 878 a warning is provided. This warning, in addition to being visual, may be the audible. It should also be understood that as the cement is mixed, the current drawn by the motor 34 continually remains below the acceptable minimal level. If this event occurs, the mixing process will increase beyond a set time boundary. In step 882, (FIG. 26E) the system monitors the time of mix duration to determine if it is excessive. If this determination tests positive, a warning is presented. This provides the surgical personnel with notice that there may be something abnormal in the components used to mix the cement.

The above configuration of the system of this invention automates the mixing of surgical cement. Surgical personnel are automatically informed of mixture components that should be used to form the cement such as cement type and quantity, monomer type and quantity, desirable/required additives as a function of the components, the implants, with which the cement is to be used. This reduces the likelihood that potentially improper components or component quantities will be introduced into the cement mixture. Similarly, based on the components used to form the cement, the surgeon preferences and the mixing system components, the time and process by which the components are mixed together is automatically calculated. This reduces the time required to make these calculations and the likelihood human error could result in inaccurate calculations.

During the actual mixing process, the system of this invention regulates the operation of the tool 30 employed to perform the mixing. Surgical personnel are not required to devote appreciable mental or physical effort to ensure the tool properly mixes the components together forming the cement. Again, owing to the automated control of the tool 30, the likelihood human error will result in excess or insufficient mixing is substantially reduced.

Once the mixing process is completed, the system provides an immediate indication of whether or not the cement may be to viscous or set too quickly for use. The system also provides data indicating when the cement will set. Thus, if the surgeon indicated that he/she wanted the cement to have a set time of 10 minutes, the system indicates if the set time may be less, for example 9:30 minutes. This information lets the surgeon know that it may be necessary to perform certain parts of the surgical procedure at a relatively fast rate. Alternatively, if the data generated by the system indicates that the set time will be reached at a slightly longer time, for example 11:00 minutes instead of 10:00 minutes, the surgeon is likewise made aware of this fact so that he/she is aware of this fact and can adjust performance of the procedure as is appropriate.

VI. Auxiliary Unit Communication and Power Sharing

As discussed above, an auxiliary unit such as a transceiver head 530 or tracker 539 (both in FIG. 17), may be fitted to the powered surgical tool 30 of this invention. Other types of auxiliary units that may be so connected are laser pointers and light sources. Still another class of auxiliary unit performs a sensing function. One such auxiliary unit is includes an infra-red transducer. This type of auxiliary unit is used to monitor the temperature of the tissue at the surgical site.

Figure 32:
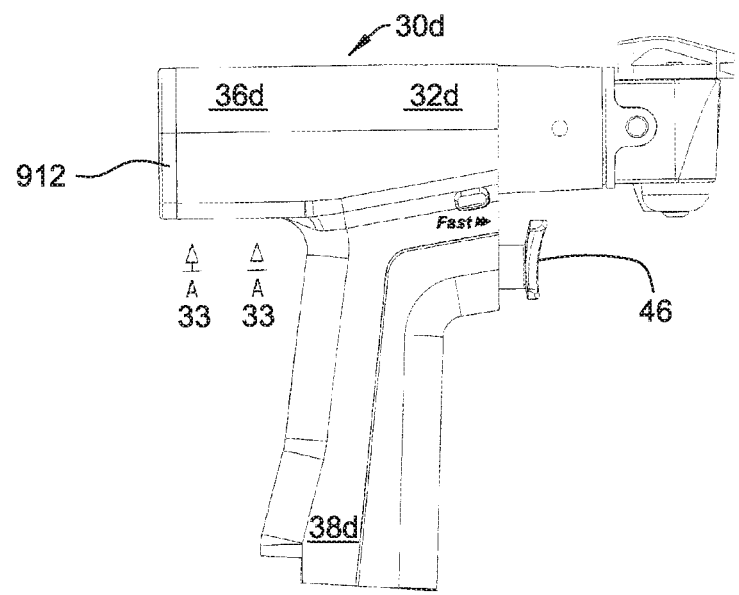
FIG. 32 is a side view of an alternative tool housing of the surgical tool of this invention.
Figure 33:
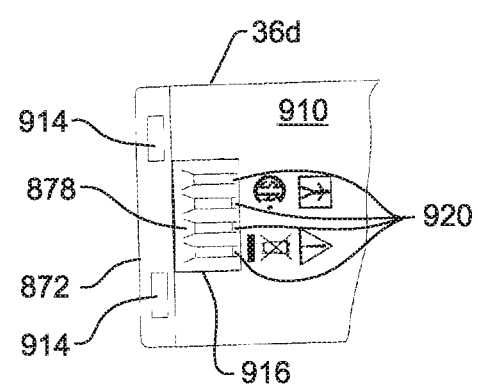
FIG. 33 is a plan view of the bottom surface of the proximal end of the housing head when viewed from line 33-33 of FIG. 32.

FIGS. 32 and 33 illustrate how a surgical tool 30*d* of this invention is provided with contacts 920 over which data signals are exchanged with the auxiliary unit. Contacts 920 also serve as the conductive members over which power from the tool battery 42 (FIG. 6E) is selectively supplied to the auxiliary unit.

Tool 30*d* has a housing 32*d* with a head 36*d* from which handle 38*d* extends. Housing 32*d* is formed so as to have a head bottom surface 910 of head 36*d* that extends proximally from handle 38*d* is planar. A cap 912 closes the open proximal end of housing head 36*d*. The base of cap 912 is coplanar with head bottom surface 870. Two spaced apart rectangular indentations 914 are formed in the bottom flat surface of cap 872. Tool 30*d* is shown with a single switch 46.

Head bottom surface 910 is formed with a rectangular cut-out 916 that opens to where the edge along which cap 912 abuts housing 32*d*. A terminal 918 is seated in cut-out 876. Contacts 920, which extend downwardly towards handle 38*d*, are part of terminal 918. In the illustrated version of the invention four contacts 820 are provided.

Figure 34:
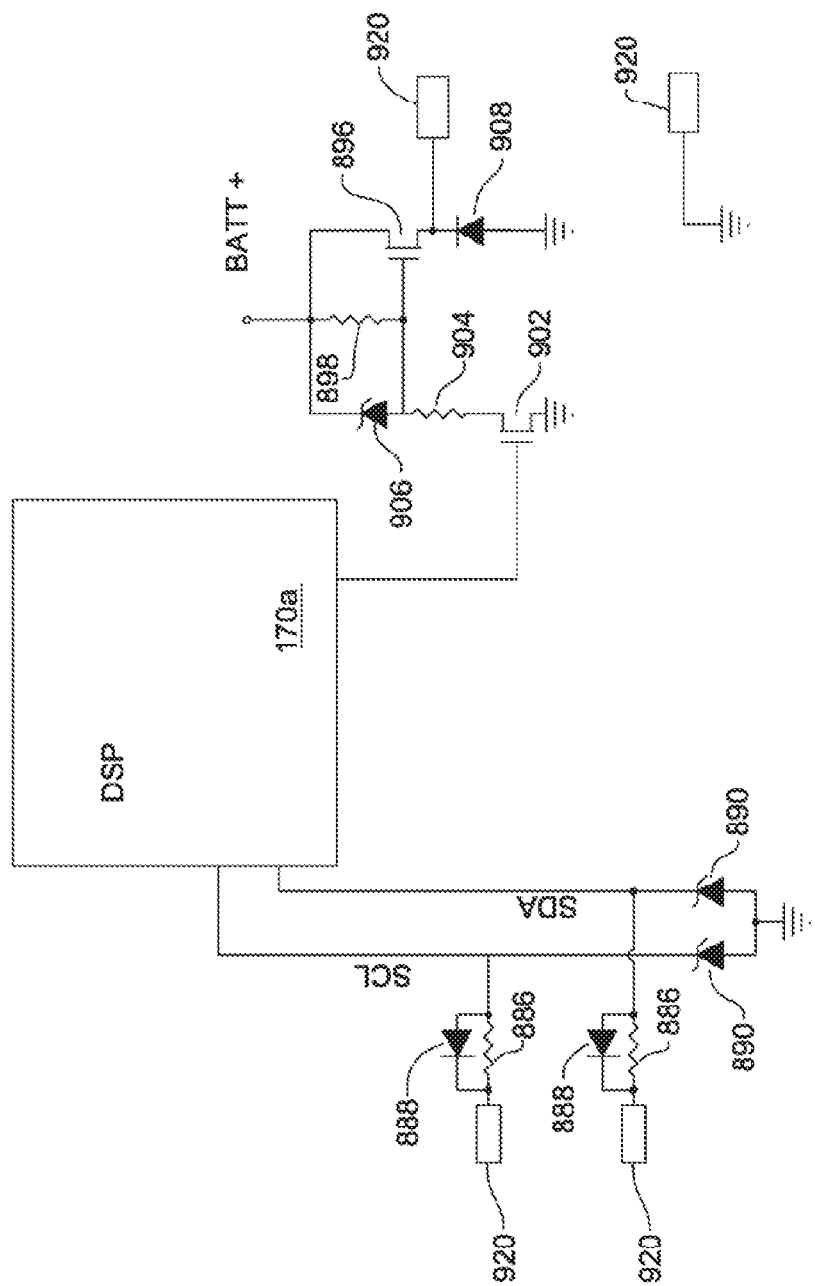
FIG. 34 is a partial schematic view of the electrical components internal to the alternative tool showing how signals are exchanged with between the tool control processor and the auxiliary unit and how the power from the battery connected to the tool is selectively supplied to the auxiliary unit.

FIG. 34 illustrates the components internal to the tool 30*d* to which contacts 920 are connected. Two contacts 920 are communications contacts. In one version of the invention, communication between the tool 30*d* and the auxiliary unit is in accordance with the I²C protocol available from Philips Semiconductor. Accordingly, a first one of the contacts 920 is the contact over which clock signal, SCL signals, are transmitted. A second contact 920 is the contact over which serial data signals, SDL signals, are exchanged. In FIG. 34 each contact 920 that functions as a communications contact is connected to the DSP 170*a*. More particularly, each contact is connected to the DSP 170*a* through a resistor 886. A diode 888 is series connected across each resistor 886. Diodes 888 provide low resistance bypass paths around the resistors 886 for the SCL and SDA signals emitted from the DSP 170*a* to the auxiliary unit.

A reverse bias zener diode 890 is connected between each I²C pin on DSP 170*a* and ground. Diodes 890 thus protect the DSP 170*a* from voltage spikes.

A third one of the contacts 920 functions as the conductive member over which the charge in the tool battery 42 is supplied to the auxiliary unit. Battery 42 is selectively tied to the contact 920 by a normally open p-channel FET 896. The BATT+ signal is applied to the drain of FET 896. The contact 920 is tied to the FET source. The BATT+ is applied through a resistor 898 to the gate of the FET 896 so as to normally hold the FET open.

An n-channel FET 902 drives the voltage at the gate of FET 896 below the source voltage so as to selectively switch FET 896 closed. The source of FET 902 is connected to the gate of FET 896 by a resistor 904. The drain of FET 902 is tied to ground. FET 902 is gated by a single asserted from DSP 170*a*. A zener diode 906 is reverse bias connected between the BATT+ pin and the junctions of resistors 898 and 904. A diode 908 is reverse bias connected between the source of FET 896 and ground.

Normally, the BATT+ signal applied through resistor 898 to the gate of FET 898 holds FET 898 in the off state.

An auxiliary unit (not illustrated) may have open faced shell that allows the unit to be fitted over the proximal end of the housing head 36*d*. When the shell is so positioned, moveable fingers integral with the shell seat in housing indentations 874. A latch mechanism, part of the auxiliary unit, holds the fingers in the indentations so the fingers hold the auxiliary unit to tool 30*d*.

Data from the auxiliary unit received over the I²C communications link may inform the DSP 170*a* that the auxiliary unit is allowed to draw the power stored in the battery 42. In the event the auxiliary unit is so authorized, DSP 170*a* asserts a signal to gate FET 902. FET 902 thus closes so as to tie resistor 904 to ground. This results in the voltage present at the gate of FET 896 dropping below the voltage of the source so as to turn the FET 896 on.

As seen in FIG. 34, the fourth contact 920 establishes a connection between the circuit internal to auxiliary unit and the ground of the circuit of tool 30*d*.

Sealed module 40 of the surgical tool 30 of this invention does more than simply protect the circuit components that regulate actuation of the tool power generating unit (motor 34) and that monitor the user actuated control members (trigger switches 46 and 47). Module 40 also protects the sensors (Hall sensors 74 and 76) that generate output signals representative of the operating state of the power generating unit. Sensors 74 and 76 are not exposed to the harsh moist environment of autoclave sterilization. By so protecting the sensors, the likelihood of their failure is reduced.

Still another feature of versions of the surgical tool 30 of this invention that include motor 34 is that only two sensors, Hall sensors 74 and 76, are required to provide signals representative of the position of motor rotor 78. This reduces by one the number of sensors normally employed to provide the feedback needed to monitor the position of a brushless DC motor. This represents a cost savings over conventional monitoring assemblies.

Also, the use of the two Hall sensors 74 and 76 and the means by which they provide an accurate means to determine rotor position when the motor is at start up, the 0 RPM state, eliminates the need to employ other means that may consume significant amounts of power to start the motor and determine initial rotor position. This is especially useful in versions of this invention wherein the power to energize the motor is from battery 42. The minimization of reduced power draw at startup of this invention serves to increase the overall time any one battery can be used to power the motor 34 before the battery is discharged.

The construction of the power control module 40 has other advantages. In particular, mounting plate 119 serves more functions as just the member to which FETs 82a-82c, 84a-84c and 336a-336c are mounted. Mounting plate 119 serves as a heat sink for drawing heat away from the FETs to the tool housing 32. Mounting plate distal end section 121 functions as a spacer to prevent the module front plate 92 from abutting the proximal ends of the trigger switches 46 or 47. Such contact, if allowed to occur, can adversely affect the pattern of the magnetic fields emitted by magnets 56 and 57.

During assembly of the control module 40, mounting plate functions as a backing for circuit board 64. This eliminates the need to introduce a separate backing plate into the assembly process in order to perform wire bonding between FETs 84a-84c and 336a-336c and the adjacent surface of the circuit board. Once control module 40 is manufactured, mounting plate 64 functions as a support bracket for the circuit board 64.

Still another feature of surgical tool 30 of this invention is that, unless the tool is being actuated or was just actuated, the control circuit components are in the sleep mode. When the control circuit components are in this mode, less power is consumed than when they are in the active mode. This arrangement minimizes the draw on battery 42. When either trigger switch 46 or 47 is initially displaced from the at-rest position, sensor 66 or 70 essentially immediately undergoes a state change. This results in the rest of the control circuit essentially simultaneously transitioning into the awake mode. Thus, while this feature of the invention serves to reduce current draw on the battery 42, it does not noticeably affect operation of the tool.

Surgical tool 30 of this invention is further constructed so that control processor internal to the tool (DSP 170) is selectively programmed to vary the tool control signals generated as a function of the depression of the actuating members (trigger switches 46 and 47). As indicated by the above described processes, this feature of the invention makes it possible for the operation of the tool power generating unit (motor 34) based on the actuation of the member to be custom set based on doctor preference, type of attached surgical attachment 41, procedure being performed or point in the procedure. Thus, a cordless surgical tool 30 of this invention can be custom configured and custom operated in essentially the same ways that, previously, only corded tools could be so configured and operated.

VII. Alternative Embodiments

The above descriptions are directed to specific embodiments of this invention. Other versions of the invention may have features different from what has been described. For example, while the described motor has a rotating shaft, other motorized surgical tools of this invention have drive members that oscillate or reciprocate.

It should likewise be clear that this invention is not limited to surgical tools with motors. Other surgical tools of this invention may have other power generating units such as units designed to emit RF energy, heat, light energy or ultrasonic energy.

The type of sensing transducer internal to the control module that monitors the operation of the power generating unit is a function of the type of power generating unit. For example, if the power generating unit emits RF energy, internal to the unit may be an inductor that generates a magnetic field as a function of the power emitted by the unit. Internal to the module is a sensor similar to the described Hall effect sensors that monitor the strength of the magnetic field. Alternatively, the power generating unit may emit light, in the ultra-violet, visible or infrared spectrum as a function of the operating state of the unit. For example a fraction of the light emitted by a light-generating power generating unit may be diverted towards the control module. Alternatively an RF power generating unit may include a member that emits an infra-red light signal as a function of the extent to which the surgical site to which the associated surgical attachment is heated. In these versions of the invention, the structural component of the module includes a window that is transparent to the type of light emitted by the power generating unit or the surgical site. Internal to the control module, behind the window, is a transducer sensitive to the spectrum of emitted light.

Alternatively, the transducer assembly internal to the control module is sensitive to mechanical energy emitted by the power generating unit. For example, if the power generating unit includes a vibrating transducer, the surgical tool may have a conduit through which a fraction of the generated vibrations are transmitted to the control module. In this version of the invention, the structural wall of the control module is formed from material that does not appreciably attenuate these vibrations. A motion-sensitive transducer internal to the control module generates signals in response to the output vibrations.

It should similarly be appreciated that, even in versions of the invention wherein the power generating unit is some type of motor assembly, the sensor assembly internal to the control module that remotely monitors the operation of the power generating unit need not always be magnetic strength sensor. For example, in some versions of the invention, the control module sensor is photo-sensitive unit responsive to light emitted or reflected by the motor. In these versions of the invention, motor 34 is provided has a moving surface along which material of different reflectivity is applied. A light is emitted towards the moving surface. Internal to the control module is a photosensitive transducer that monitors the light reflected from a fixed area. As the moving surface transits across the fixed area, the amount of reflected light detected by the sensor varies with the reflective of the applied material. Thus, in this version of the invention, a sensor disposed in the control module provide feedback regarding the operating state of a mechanical power generating unit without monitoring magnetic fields. An inductor that may or may not be magnetically biased may also function as the sensor.

Similarly, in some versions of the invention, the sensor internal to the control module is sensitive to mechanical motion, vibrations emitted by the motor and transmitted through the control module.

Figure 35:
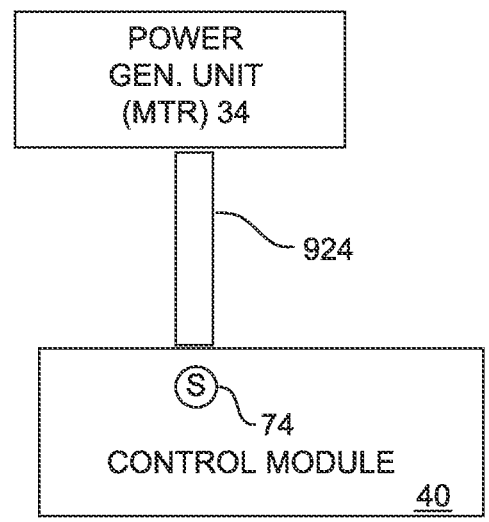
FIG. 35 is a diagrammatic illustration of how a flux pipe serves as the conduit for conducting the energy emitted by the tool power generating unit to the sensor in a remotely located control module.

Further in some versions of the invention, a flux pipe may serve as a conduit for transmitting energy emitted by the tool power generating unit to the control module. Diagrammatically, such an assembly is illustrated by FIG. 35. Here a flux pipe 924 that serves as a good conductor for the emitted energy or is transparent to the energy extends from the power generating unit 34. For example, if the magnetic energy is emitted by the power generating unit 34, flux pipe 924 is formed material with high magnetic permeability. (In this situation, the flux pipe may actually include a center core of highly magnetically permeable material, an inner sleeve of relatively impermeable material and an outer sleeve of highly permeable material.) If the emitted energy is light energy, flux pipe 920 is formed from material relatively transparent to the light emitted by the power generating unit. The free end of the flux pipe terminates adjacent the control module structural member enclosing the module sensor. An advantage of this construction of the invention is that it makes it possible to position the control module at a distance from the power generating unit further away than it may otherwise be possible to locate module.

Similarly, it should be recognized that there is no requirement that in all versions of the invention, control module 40 be hermetically sealed. Manufacturing economics or other factors may make it undesirable to so assemble the control module. Thus, in some versions of the invention where it is still necessary to protect the components internal to the module from the rigors of sterilization, the module may be filled with a potting compound.

Likewise, there is no requirement that all versions of the invention have each of the above-described components. Thus, in some versions of the invention, the control module may not include sensors for monitoring the actuation of the manually actuated control members. Similarly, there is no requirement that tool 30 of this invention always be cordless. Similarly, while in many versions of this invention, Hall sensor 74 and 76 that generate signals representative of the position of the motor rotor be mounted in the control module, that need not always be the case. In some versions of this invention, for example tools of this invention wherein the sensors do not have to be protected from a harsh environment, manufacturing economics or other factors may require that one or both of the sensors 74 and 76 be placed outside the control module. For example, these sensors may be placed in the tool relatively close to the motor rotor 78.

Also, there may be some tools wherein it is desirable to provide the control assembly with the power FETs on mounting plate arrangement of this invention. However, for other reasons, neither the actuating member sensors nor the power generating unit sensors are disposed in the module. In these versions of the invention the control assembly may not even be a sealed module.

It should similarly be appreciated that that the inventive features of this tool may be employed in tools other than surgical tools.

In motorized tools constructed in accordance with this invention wherein a Hall sensor 74 is employed to generate signals representative of the position of the motor rotor 78, there may not be any need to perform the process described that continually update the signal reference levels for determining when the HALLx signals undergo state transitions. This updating may be eliminated if empirical analysis determines that the output signal from Hall sensor 74 remains relatively steady over time of tool operation and with changes in temperature. Eliminating these steps reduces the process steps needed to be performed by the control processor (DSP 170).

Also, the process steps practiced by the system and method of this invention may differ from what has been described. For example, in step 494, the control processor (DSP 170) uses Equation 1, a linear equation, based on trigger displacement, generate the USER_SPEED signal. Equation 1 is an example of just one equation that can be used to generate the USER_SPEED signal. Alternatively the control processor can be set to generate a USER_SPEED signal that varies non-linearly as a function of trigger displacement.

Figure 36:
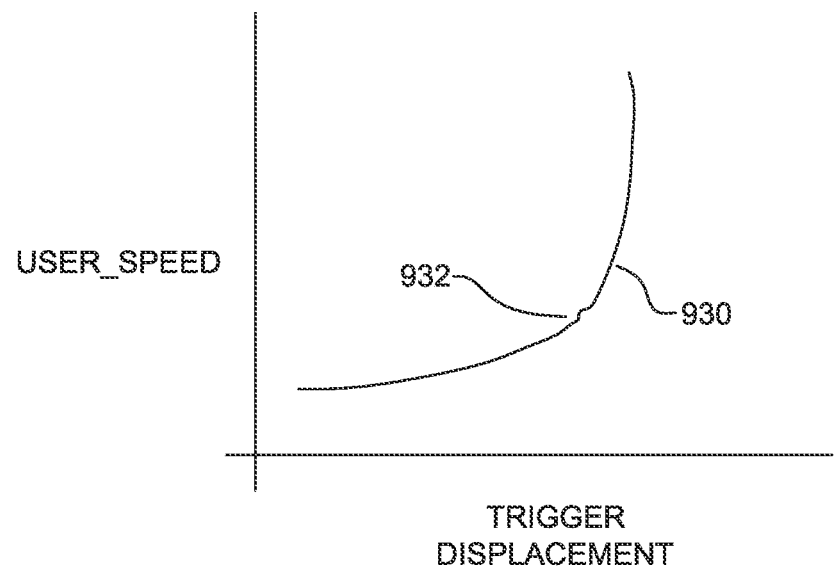
FIG. 36 is a graphic depiction of how the tool control processor can be programmed to vary the USER_SPEED signal non-linearly as a function of the displacement of the tool actuating member.

For example, plot 930 of FIG. 36 illustrates how, if Equation 1 is modified, control processor (DSP 170) outputs a USER_SPEED signal that increases exponentially with the displacement of the trigger switch, Plot 930, while being generally exponential also has a discontinuity 932. Discontinuity 932 represents how it control processor 170 can further be programmed to generates USER_SPEED signals that skip over certain speeds. One reason this discontinuity may be desirable is to prevent the rotation of a surgical accessory 41 such as a bur at a speed equal to the natural resonant frequency of the bur. By avoiding the driving of the bur at the frequency, the extent to which the bur vibrates while being actuated is minimized.

Similarly, the processes employed to operate the tool of this invention may vary owing to the use of different components. For example, the tests of step 378 to determine rotor position at start-up, 0 RPM, are based on the assumption that sensor 76 is electrically within 60° of sensor 74. In an alternative construction of the invention, sensor 76 is electrically between 60 and 120° of sensor 74. In these versions of the invention, sensor 76 may even output a digital signal as a function of rotor position. In FIG. 9, this signal is represented by plot 908.

Here, at start up, in step 378, the determination of the particular (electrical) sextant in which the rotor is located is made according to the following process. If the normalized output signal from sensor 74 indicates the rotor 78 is in either that 0 to 60° sextant or the 120 to 180° sextant, a test is made to determine if:

sensor 76 signal>0

If this determination tests false, then collectively the sensor signals indicate the rotor is in an angular position between 0 and 60°. If this determination tests true, collectively the signals indicate the rotor is in a position between 120 and 180°. If the normalized output signal from sensor 74 indicates the rotor is in either the 180 to 240° sextant or the 300 to 360°, the above test of the output signal from sensor 76 is executed. Here, if this determination tests true, then the sensor signals indicate the rotor is in an angular position between 180 and 240°. If this determination tests false, then the rotor is in a position between 300 and 360°.

An advantage of the above version of the invention is that it eliminates the need to precisely set the amplitude of the output signals for sensors 74 and 76 relative to each other. In the previously described version of the invention, such regulation is required in order to generate the signals on which the described comparisons can be performed. (The degree of signal regulation is inversely related to the electrical phase difference of the sensors 74 and 76 from each other.) Since, in this version of the invention, the signal from sensor 76 is compared to a reference value, no such regulation is required. Also, in this version of the invention, the sensor 76 can be either output an analog or digital signal.

Figure 37:
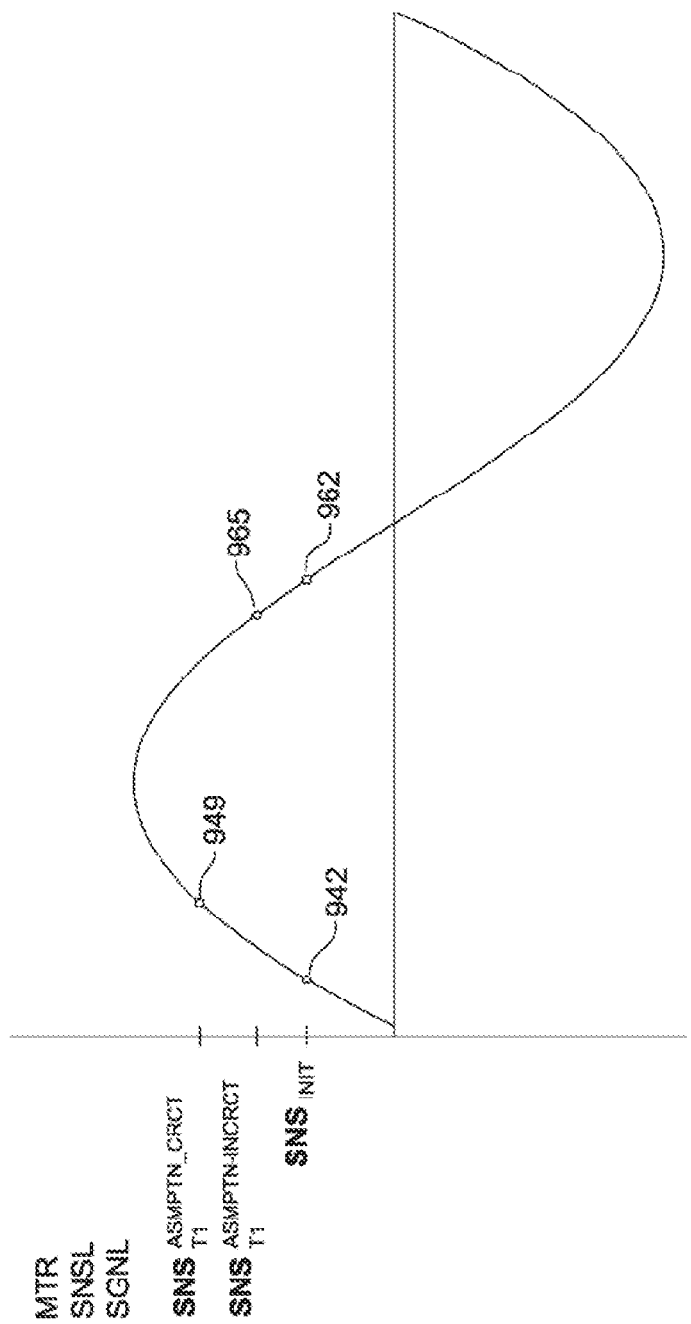
FIG. 37 is a wave form of the signal generated by a sensor monitoring the state of a two pole rotor wherein the plot points are used to illustrate the measurements taken during execution off the base assumption algorithm.
Figure 38:
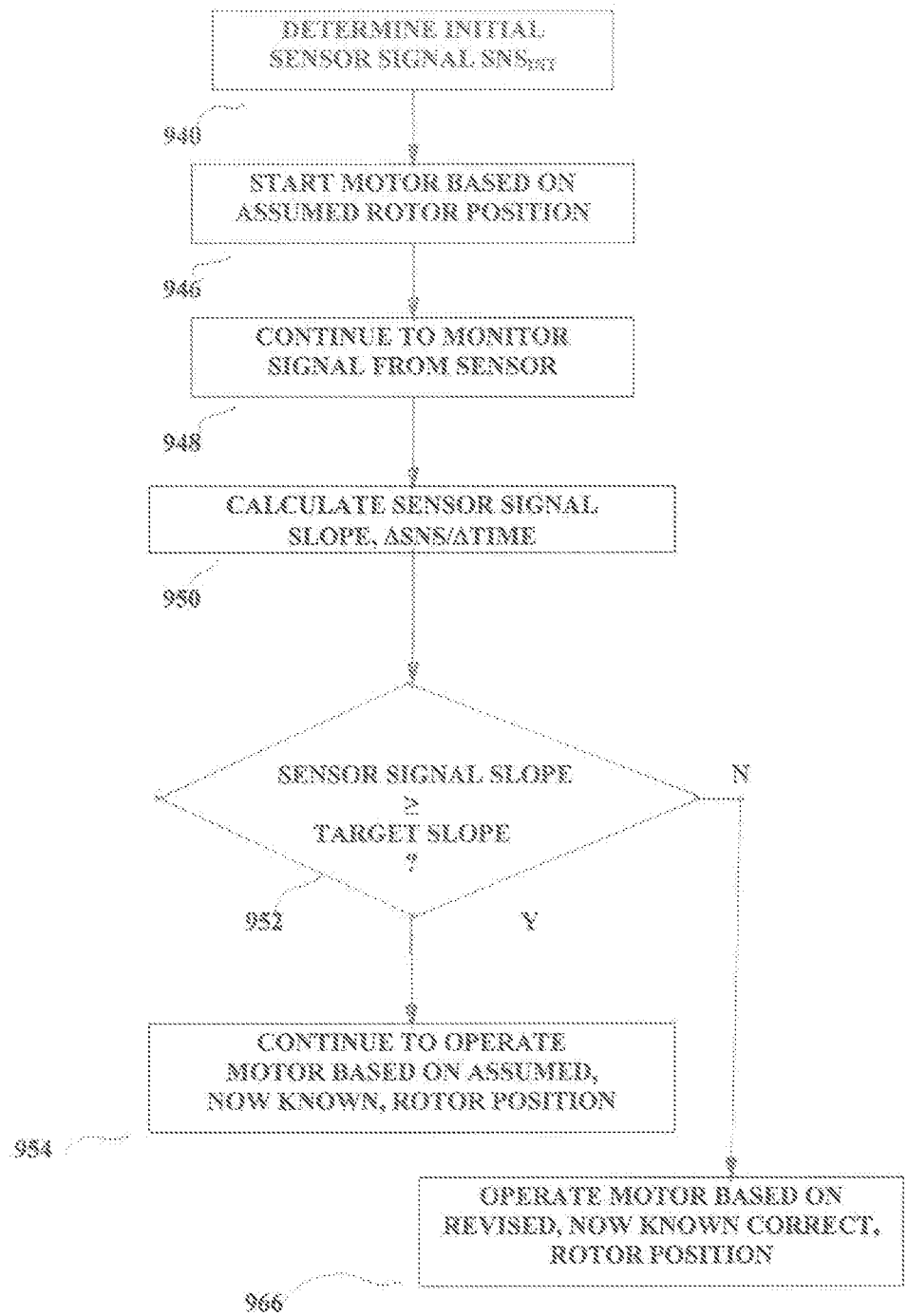
FIG. 38 is a flow chart of the steps executed as part of the base assumption algorithm of the tool of this invention to determine rotor position at start up with a single sensor.

It may even possible to determine the position of the motor rotor at start up, in which portion of the signal cycle the signal is in, without the signal from the supplemental sensor, sensor 76. FIG. 37 illustrates the process steps executed using a base assumption algorithm to perform this process. In this process, in step 940, based on the signal from sensor 74, the DSP determines outputs an initial signal, $SNS_{INIT}$. This means that rotor position is either in the first sextant that includes point 942 or the third sextant that includes point 962 of FIG. 38. For purposes of simplification, FIG. 38 is a plot of the signal out of sensor 74 for a two-pole rotor. Thus the single 0 to 360° signal output by motor rotor sensor 74 corresponds to a single rotation of motor rotor 78. In a step 946, DSP asserts start-up signals to the motor based on the assumption that the $SNS_{INIT}$ signal from sensor 74 indicates that the rotor 78 is in the first sextant. As represented by step 948, the DSP 170 continues to monitor the signal from sensor 74.

If the assumption upon which the execution of step 946 is based is correct, and the rotor will turn in the selected direction. This results in the SNS signal output by sensor 74 undergoing an appreciable change from the $SNS_{INIT}$ level. In other words, the ΔSNS/Δtime slope is appreciable. In FIG. 37, this is represented by the level of the $SNS_{T1}^{ASMPTN\_CRCT}$ signal, represented by point 949, being appreciably different from the level of the $SNS_{INIT}$ signal. Thus, in a step 950, based on the next measured signal, the $SNS_{T1}$ signal from sensor 74, the DSP determines the magnitude of the ΔSNS/Δtime slope. In a step 952 the magnitude of the ΔSNS/Δtime slope is compared to a target slope. If the magnitude of the calculated slope is at least as great as the target slope, DSP 170 interprets this result as indicating the initial assumption was correct; the rotor was in the first sextant of rotation. The DSP 170 therefore continues to assert control signal based on the initial assumption, now proven correct, regarding rotor rotational position, step 954.

However, the $SNS_{INIT}$ signal may actually be indicating that the rotor at start-up was in the third sextant, the sextant associated with the signal at point 962. In this situation, the energization signals applied to the motor coils based on the incorrect assumption of rotor position of step 946 will not cause the rotor to appreciably move. Instead, at least for a short time, the signals applied to the motor coils will only cause a small movement of the rotor until the rotor enters a locked position. Given this relatively small angular displacement of the motor rotor, the level of the $SNS_{T1}^{AMSPTN\_INCRCT}$ signal output from the sensor 74 will likewise only be marginally different from the $SNS_{INIT}$ signal level. In FIG. 37 this is represented by the relatively small difference between the signal levels at points 962 and 965.

Thus, in this situation, in step 950, when the ΔSNS/Δtime slope is calculated, the slope will relatively small. In the test of step 952 the calculated slope will be less than the target slope. The DSP 170 interprets this result as indicating that, in fact the rotor was not in the first sextant of rotation but actually in the third sextant. Therefore, in a subsequent processing step, step 966, the DSP continues to assert control signals to the MCC 172 based on the revised and proven correct interpretation of rotor position.

It should be understood that in the above process step, the test of step 952 is based on the absolute slope. The positive or negative gradient of the slope is irrelevant as this is a function of the direction of rotor movement.

Alternative means may be employed to avoid the need to provide two sensors for determining rotor position at start up. In another alternative scheme, the control circuit, at start up, first applies currents to the coils that cause the motor rotor to turn to a known position that can be determined from the peak or valley signal from the single sensor 74. Once sensor 74 indicates the rotor is in this state, additional start up signals are applied to rotate the rotor from the known state.

It should likewise be understood that communications protocols other than I²C may be used to exchange signals with the tool control processor (DSP 170). One alternative protocol may be the one-wire protocol developed by Dallas Semiconductor.

In alternative versions of the invention, DSP 170 can perform some of the control functions performed by the motor control circuit 172. For example, the DSP 170 can regulate operation of the tool 30 when the tool is to be driven in the oscillate mode. In this version of the invention, the DSP monitors the degrees of rotation the motor rotor 78 turns in each direction of an oscillate cycle. At any given instant the DSP only asserts a single one of the FORWARD or REVERSE signals to the MCC. Once the DSP determines the rotor has turned a set number of degrees in one direction, for example the "reverse" direction, it switches from asserting the REVERSE signal to the FORWARD signal. This switch of instruction signals causes the MCC to stop asserting signal that cause the rotor to turn in the reverse direction and start asserting signals that cause the rotor to turn in the forward direction.

An advantage of the above arrangement is that surgeon can program the DSP 170 so that the DSP causes the motor rotor to oscillate in an unequal rotational sequence. For example, by using the DSP to regulate oscillate, tool 30 can be configured so that the rotor, more particularly after speed reduction, the attachment rotates first 720° in a first direction and then 360° in the second direction before repeating the sequence. Other sequences are also possible, for example 720° in the first direction, 360 in the second direction, 360° in the first direction and 360° in the second direction before repeating are also possible.

Further, by allowing the DSP to regulate oscillation, the DSP can ramp up and ramp down the rotor speed at, respectively the start-up and end periods of the rotation in each directional cycle. This dampening of the acceleration and deceleration (braking) of the rotor can reduce tool vibration.

Also, it should be understood that the control functions of the system of this invention may further vary from what is described. Clearly, a surgeon can reconfigure control function of each trigger switch 46 and 47 during the middle of the procedure. Also, when plural tools 30 are used one may be used as an override of the other. Thus, in a teaching a situation the instructor's tool 30a is configured so that when one trigger switch is depressed, the control processor generates a stop command for execution by the second tool 30b. This stop command is transmitted through the tool data transceiver head 530 to the wireless transceiver head 536. After receipt by the wireless transceiver head 536, head 536 or another component causes the stop command to be transmitted to the student's handpiece 30b. In this configuration of the system the second trigger switch of the instructor's handpiece 30a is configured to actuate the power consuming unit internal to that handpiece to allow the instructor to complete the procedure.

Also, the manually set actuator(s) used to regulate operation of the surgical tool 30 may vary from the disclosed trigger switches. In some versions of the invention, the tool may only have a single trigger switch. In these versions of the invention, the tool may have a bi-state lever arm. The surgeon selectively sets the lever arm based on the operating mode in which he/she wants to operate the tool. Thus if the power generating unit internal to the tool is a motor 34, some of the bistate settings that can be regulated by the setting of the lever arm are: forward/reverse; forward/oscillate; and low speed/high speed. With these versions of the invention, in steps 360 and 262, the bistate operational ranges for the tool are loaded into the control processor (DSP 170).

Likewise, in versions of the invention wherein motor 34 functions as the power generating unit, during start-up the two sensors may be used to determine rotor position as described. Then, post start up, two or more sensors are used to determine the subsequent positions of the spinning motor rotor.

Similarly in other versions of the invention, the manual actuators may not be trigger switches. In these versions of the invention, one or more push buttons mounted to the tool housing 32 regulate the actuation of the power generating unit. Each push button may, for a short period of time, bring a magnet in sufficient proximity to an associated control module sensor that the output signal from the sensor undergoes a state transition. These types of control members are appropriate for regulating the actuating of power generating units that are suited to step level control. RF ablation tools are one such type of tool.

In some versions of the invention, the sensor or sensors used to determine if a switch has been actuated, sensors 66 and 70 in the described embodiment, may not be digital sensors. In alternative versions of the invention, the sensors may be analog sensors. These sensors may even be microswitches or reed switches. In these versions of the invention, the wiper integral with the switch makes or breaks a connection based on displacement of the associated switch.

Alternatively, it may be possible to eliminate sensors 66 and 70 from some versions of the invention. The signal from a sensor used to monitor switch actuation is employed by a first circuit to control the actuation and negation of the AWAKE signal. The signal is then used by a second circuit to produce an output signal representative of the user desired operating rate for the power generating unit internal to the handpiece.

It should likewise be recognized that while, in many versions of the invention, coupling assembly 39 allows the surgical attachment 41 to be removably attached to the tool 30, that is not always the case. In some versions of the invention, coupling assembly 39 is a fastening device or fastening assembly that permanently holds the surgical attachment to housing 32 and the power generating unit. These assemblies are common in disposable versions of this invention.

It should thus be appreciated that the other individual components from which the tool of this invention are formed may vary from what has been described. A conventional microprocessor may function as the tool control processor. Plural components may substitute for the ASIC forming the motor control circuit 172. In some versions of the invention, the signals asserted by sensor 66 or 70 when magnet 56 or 58, respectively, is first asserted may function as the AWAKE signal. This eliminates the processing required by the DSP 170 otherwise required to assert this signal.

Internal to the handpiece housing 32 there may be a nonvolatile memory to which data are written to by the control processor (DSP 170). This memory functions as the tool log in which the data regarding the tool operation, including the particulars regarding the when and what of exceptional events occurred.

Similarly, the processes of this invention may be executed using less steps or in alternative arrangements of the steps than what has been described.

Therefore, it is the object of the appended claims to cover all such variations and modifications as come within the true spirit and scope of this invention.

What is claimed is:

1. A surgical system comprising:
a surgical tool comprising a handpiece housing and a power generating unit disposed in the handpiece housing for actuating a surgical accessory coupled to power generating unit to perform a surgical task;
a surgical navigation system configured to track a position of the surgical tool relative to a defined boundary; and
a wireless transceiver removably connectable to the handpiece housing for receiving wireless signals that control operation of the power generating unit,
wherein, based on the tracked position of the surgical tool relative to the defined boundary, the surgical navigation system is configured to communicate a signal to the wireless transceiver that limits operation of the power generating unit of the surgical tool.

2. The surgical system of claim 1, wherein the surgical tool is a cordless surgical tool, and further comprising a tool battery removably attached to the handpiece housing that is configured to supply power to the power generating unit and the wireless transceiver during operation of the surgical tool.

3. The surgical system of claim 1, wherein the surgical tool further comprises contacts proximate the handpiece housing for engaging corresponding contacts coupled to the wireless transceiver when the wireless transceiver is connected to the handpiece housing, at least one of the contacts of the surgical tool being configured to receive signals from the wireless transceiver that control operation of the power generating unit.

4. The surgical system of claim 3, wherein the surgical tool further comprises a tool control processor disposed in the handpiece housing and coupled to the at least one contact of the surgical tool and the power generating unit, and the wireless transceiver is configured to, responsive to receiving the signal communicated from the surgical navigation system, communicate a corresponding signal to the tool control processor through the at least one contact that causes the tool control processor to limit the operation of the power generating unit of the surgical tool.

5. The surgical system of claim 3, wherein the contacts of the surgical tool are further configured to supply power from a power source for the surgical tool to the wireless transceiver when the wireless transceiver is connected to the handpiece housing.

6. The surgical system of claim 5, wherein the surgical tool is a cordless surgical tool, and further comprising the power source with the power source being a tool battery removably attachable to the handpiece housing.

7. The surgical system of claim 1, further comprising a tracker removably connectable to the handpiece housing, wherein the tracker includes the wireless transceiver and is configured to emit light signals that are detected by the surgical navigation system to determine the position of the surgical tool relative to the defined boundary.

8. The surgical system of claim 7, wherein the surgical tool further comprises contacts proximate to the handpiece housing for engaging corresponding contacts of the tracker when the tracker is connected to the handpiece housing, at least one of the contacts of the surgical tool being configured to receive signals from the wireless transceiver of the tracker for controlling operation of the power generating unit.

9. The surgical system of claim 8, wherein the contacts of the surgical tool are further configured to supply power from a power source for the surgical tool to the wireless transceiver of the tracker when the tracker is connected to the handpiece housing.

10. The surgical system of claim 9, wherein the surgical tool is a cordless surgical tool, and further comprising the power source with the power source being a tool battery removably attachable to the handpiece housing.

11. A surgical system comprising:
a surgical tool comprising a handpiece housing and a power generating unit disposed in the handpiece housing for actuating a surgical accessory coupled to the power generating unit to perform a surgical task; and
a powered auxiliary unit removably connectable to the handpiece housing,
wherein the surgical tool is configured to supply power from a power source for the surgical tool to the power generating unit and to the auxiliary unit during operation of the surgical tool, and
wherein the auxiliary unit is a tracker configured to emit light signals from the power supplied by the surgical tool, the light signals for being detected by a navigation system to track a position of the surgical tool relative to a surgical site.

12. The surgical system of claim 11, wherein the surgical tool is a cordless surgical tool, and the power source is a tool battery removably attachable to the handpiece housing.

13. The surgical system of claim 12, further comprising the tool battery removably attachable to the handpiece housing.

14. The surgical system of claim 11, wherein the surgical tool further comprises contacts proximate the handpiece housing for engaging corresponding contacts of the tracker when the tracker is connected to the handpiece housing, the contacts of the surgical tool being configured to supply power from the power source for the surgical tool to the tracker.

15. The surgical system of claim 14, wherein at least one the contacts of the surgical tool is configured to receive signals from the tracker for controlling actuation of the power generating unit.

16. The surgical system of claim 14, wherein the tracker comprises a wireless transceiver for receiving signals from a remote system for controlling operation of the power generating unit, and at least one of the contacts of the surgical tool is configured to receive signals from the wireless transceiver that control operation of the power generating unit and correspond to the signals received from the remote system.

17. A surgical system comprising:
a surgical tool comprising a handpiece housing and a power generating unit disposed in the handpiece housing for actuating a surgical accessory coupled to the power generating unit to perform a surgical task; and
a powered auxiliary unit removably connectable to the handpiece housing,
wherein the surgical tool is configured to supply power from a power source for the surgical tool to the power generating unit and to the auxiliary unit during operation of the surgical tool, and
wherein the surgical tool is configured to:
determine whether the auxiliary unit is connected to the handpiece housing; and
responsive to determining that the auxiliary unit is connected to the handpiece housing, supply the power from the power source for the surgical tool to the auxiliary unit.

18. An auxiliary unit for use with a surgical tool including a handpiece housing and a power generating unit disposed in the handpiece housing for actuating a surgical accessory coupled to power generating unit to perform a surgical task, the auxiliary unit comprising:
a wireless transceiver configured to receive a signal from a surgical navigation system that includes an instruction to limit operation of the power generating unit of the surgical tool based on a tracked position of the surgical tool relative to a defined boundary, wherein the auxiliary unit is configured to be removably connected to the handpiece housing, and the wireless transceiver is configured to, responsive to receiving the signal communicated from the surgical navigation system when the auxiliary unit is connected to the handpiece housing, communicate a corresponding signal to the surgical tool that causes the surgical tool to limit the operation of the power generating unit of the surgical tool.

19. The auxiliary unit of claim 18, further comprising:
a plurality of light emitting diodes configured to receive power from a power source for the surgical tool when the auxiliary unit is connected to the handpiece housing and emit light signals from the received power for being detected by the surgical navigation system to determine the position of the surgical tool relative to the defined boundary.

* * * * *